United States Patent [19]

Fisher et al.

[11] Patent Number: 5,728,650
[45] Date of Patent: Mar. 17, 1998

[54] HERBICIDAL AZA BISPHOSPHONIC ACIDS AND COMPOSITIONS CONTAINING THE SAME

[75] Inventors: Karl J. Fisher, Petaluma; Frank X. Woolard, Greenbrae; Michael R. Leadbetter, San Leandro, all of Calif.; John M. Gerdes, Pittsburgh, Pa.

[73] Assignee: Zeneca Limited, London, England

[21] Appl. No.: 418,970

[22] Filed: Apr. 7, 1995

Related U.S. Application Data

[63] Continuation-in-part of Ser. No. 133,722, Oct. 7, 1993, abandoned.

[51] Int. Cl.$^6$ .......................... A01N 57/04; A01N 57/08
[52] U.S. Cl. .......................... 504/195; 504/207
[58] Field of Search .......................... 504/195, 207

[56] References Cited

U.S. PATENT DOCUMENTS

| | | | |
|---|---|---|---|
| 3,962,318 | 6/1976 | Kerst | 260/502.4 |
| 4,447,256 | 5/1984 | Suzuki et al. | 504/195 |
| 4,927,814 | 5/1990 | Gall et al. | 514/108 |
| 4,942,157 | 7/1990 | Gall et al. | 514/108 |
| 4,990,503 | 2/1991 | Isomura et al. | 514/80 |
| 5,133,972 | 7/1992 | Ferrini et al. | 424/449 |
| 5,280,022 | 1/1994 | Sohda et al. | 514/114 |

FOREIGN PATENT DOCUMENTS

| | | |
|---|---|---|
| 0 096 931 | 12/1983 | European Pat. Off. |
| 0 096 933 | 12/1983 | European Pat. Off. |
| 0 186 405 | 7/1986 | European Pat. Off. |
| 0 252 504 | 1/1988 | European Pat. Off. |
| 0 274 158 | 7/1988 | European Pat. Off. |
| 0 513 760 | 11/1992 | European Pat. Off. |
| 0 522 576 | 1/1993 | European Pat. Off. |
| 2 354 338 | 1/1978 | France. |
| 27 54 821 | 6/1979 | Germany. |
| 38 04 686 | 8/1989 | Germany. |
| 284 155 | 11/1990 | Germany. |
| 54-37 829 | 3/1979 | Japan. |
| 54-144 383 | 11/1979 | Japan. |
| 54-147925 | 11/1979 | Japan. |
| 55-94308 | 7/1980 | Japan. |
| 55-98105 | 7/1980 | Japan. |
| 55-98193 | 7/1980 | Japan. |
| 739 076 | 6/1980 | U.S.S.R. |
| 1 508 772 | 4/1988 | United Kingdom. |
| 93/24494 | 12/1993 | WIPO. |
| 93/24496 | 12/1993 | WIPO. |
| 94/20508 | 9/1994 | WIPO. |
| 95/10188 | 4/1995 | WIPO. |

OTHER PUBLICATIONS

Bakuniak, E., et al., "Further Studies on Biological Activity of Aminophosphonates Structurally Related to N-(Phosphonomethyl)Glycine", J. Environ. Sci. Health, vol. B18 (4–5), pp. 485–496 (1983).

Okamoto, Y., "Herbicide properties of aminophosphonic acid derivatives", IMPHOS, 1$^{st}$ International Conference on Phosphorous Compounds, Rabat, Oct. 17–21, 1977, pp. 649–652.

Chemical Abstracts, No. 091390, vol. 110, No. 11, Mar. 13, 1989.

Chemical Abstracts, No. 121244z, vol. 100, 1984.

Chemical Abstracts No. 171346a, vol. 101, 1984.

*Primary Examiner*—S. Mark Clardy
*Attorney, Agent, or Firm*—Melissa A. Shaw

[57] ABSTRACT

Herbicidal compositions containing a bisphosphonic acid compound of the formula

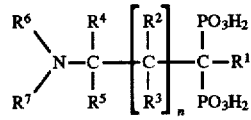

wherein n is 0, 1, 2, 3, 4, 5 or 6, or an agrochemically acceptable salt or hydrolyzable ester thereof and methods of controlling undesirable plant growth using these bisphosphonic acid containing compositions. The herbicidal compositions exhibit desirable efficacy when applied to plants post-emergence, but exhibit little significant activity when applied to plants pre-emergence. Novel aza-bisphosphonic acid compounds are also disclosed.

18 Claims, No Drawings

HERBICIDAL AZA BISPHOSPHONIC ACIDS AND COMPOSITIONS CONTAINING THE SAME

This application is a continuation-in-part of application Ser. No. 08/133,722, filed Oct. 7, 1993, abandoned.

FIELD OF THE INVENTION

This invention relates to herbicidal compositions containing an aza-bisphosphonic acid wherein the nitrogen atom and the carbon atom to which the two phosphonic acid groups are bound are linked by one to seven carbon atoms. In another aspect, this invention is directed to a method of controlling the undesirable growth of plants by applying to the area where control is desired an herbicidally effective amount of such an aza-bisphosphonic acid composition. In yet another aspect, this invention is directed to certain novel aza-bis-phosphonic acid compounds.

BACKGROUND OF THE INVENTION

The need for effective herbicides requires no special emphasis. The control of weeds and undesirable vegetation is of great economic importance since weed competition inhibits the production of foliage, fruit or seed of agricultural crops. The presence of weeds can reduce harvesting efficiency and the quality of the harvested crop. Weeds on noncropped areas may cause a fire hazard, undesirable drifting of sand or snow, and/or irritation to persons with allergies. Thus, suppression of undesirable weed growth is very advantageous.

Moreover, it is highly desirable to possess herbicides which exhibit desirable efficacy against plants when applied post emergently, but which further exhibit little significant activity when applied preemergently. Such herbicides will, for example, permit the control of weeds already present in a field but will not harm crops which have not yet emerged.

Accordingly, it is an object of this invention to provide effective novel herbicidal compositions and a novel method of controlling weeds, as well as certain novel herbicidal compounds. It is a further object of this invention to provide novel compositions, methods and herbicidal compounds which exhibit admirable postemergent control coupled with no significant preemergent control.

Japanese Patent Publication 54-147925 (Nissan Chemical) discloses herbicidal bisphosphonic acid compounds wherein the phosphonic acid groups are bound to a single carbon atom. Such compounds are of the formula:

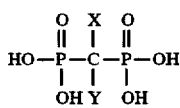

wherein X and Y are each hydrogen, halogen, alkyl or cycloalkyl; or salts thereof.

Herbicidal aza-bisphosphonic acid compounds wherein the carbon to which the two phosphonic acid groups are bound is directly linked to the nitrogen atom of the amino group are disclosed in U.S. Pat. No. 4,447,256 (Suzuki et al.); British Patent 1,508,772 (Devlin); Japanese Patent Publication 54-37829 (Nissan Chemical); Japanese Patent Publication 54-144383 (Nissan Chemical); Japanese Patent Publication 55-98105 (Nissan Chemical); and in "Herbicide Properties of Aminophosphonic Acid Derivatives", Dr. Y. Okamoto, 1st International Congress on Phosphorus Compounds, Rabat, Oct. 17–21, 1977, pp. 649–652.

The phytocidal properties of aminophosphonates structurally related to N-(phosphonomethyl)glycine, including a compound having the molecular formula:

are described in E. Bakuniak et al., "Further Studies on Biological Activity of Aminophosphonates Structurally Related to N-(Phosphonomethyl)glycine," *Journal of Environmental Science and Health*, Vol. B18, Nos. 4 and 5, pp. 485–496 (1983).

Japanese Patent Publication 55-98193 discloses certain herbicidal compounds of the formula

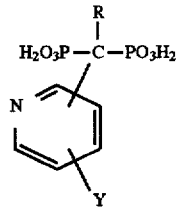

wherein R is H, lower alkyl or halogen X is —$CH_2$—, S or O; Y is H, lower alkyl or halogen; and alkali salts thereof.

Although certain aza-bisphosphonic acid compounds wherein the carbon to which the two phosphonic acid groups are bound is linked to a nitrogen atom via one or more carbon atoms have been disclosed in the art, these particular compounds are not indicated to have herbicidal activity. Thus, U.S. Pat. No. 3,962,318 discloses compounds useful as flame retardants, and German Patent DE 2754821 discloses compounds useful as chelators in water treatment. U.S. Pat. No. 5,133,972, U.S. Pat. No. 4,990,503, U.S. Pat. No. 4,254,114, U.S. Pat. No. 4,666,895, U.S. Pat. No. 4,927,814, U.S. Pat. No. 4,939,130, U.S. Pat. No. 4,942,157, European Patent Publication 96,931, European Patent Publication 96,933, European Patent Publication 186,405, European Patent Publication 274, 158, European Patent Publication 522,576, European Patent Publication 513,760, PCT Patent Publication WO 93/24500, German Patent Publication DE 3,804,686 and German Patent Publication DE 3,626,058 all disclose pharmaceutical uses for the specific compounds disclosed therein.

SUMMARY OF THE INVENTION

In one aspect, this invention is directed to an herbicidal composition comprising:

(A) an herbicidally effective amount of a compound of the Formula (I):

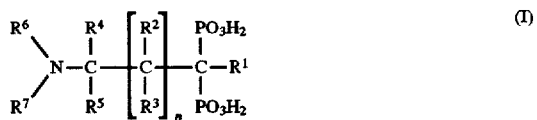

wherein n is 0, 1, 2, 3, 4, 5 or 6;

$R^1$ is hydrogen, hydroxy, $C_1$–$C_4$ alkoxy, halogen, $C_1$–$C_4$ alkyl, $C_1$–$C_4$ haloalkyl, hydroxy-$C_1$–$C_4$-alkyl, hydroxy-$C_1$–$C_4$-alkoxy or $N(R^8)(R^9)$ wherein $R^8$ and $R^9$ are each independently hydrogen or $C_1$–$C_3$ alkyl;

each $R^2$, $R^3$, $R^4$ and $R^5$ is independently hydrogen; hydrocarbyl; substituted hydrocarbyl; hydrocarbyloxy substituted hydrocarbyloxy; hydrocarbyl-$S(O)_m$—; or substituted hydrocarbyl-$S(O)_m$—;

$R^6$ and $R^7$ are each independently hydrogen; hydrocarbyl; substituted hydrocarbyl; hydrocarbyloxy; substituted hydrocarbyloxy; hydrocarbyl-S(O)$_m$—; substituted hydrocarbyl-S(O)$_m$—; pyridyl; substituted pyridyl; or are of the formula N(R$^{12}$)(R$^{13}$) wherein R$^{12}$ and R$^{13}$ are independently hydrogen, hydrocarbyl or substituted hydrocarbyl; or R$^6$ and R$^7$ together with the nitrogen to which they are bound form an aziridine; piperazine; morpholine; thiomorpholine; thiomorpholine sulfinyl; thiomorpholine sulfonyl; hexamethyleneimine; piperidine, tetrahydropyridine; pyrazole; imidazole; pyrrole; triazole; tetrahydropyrimidine; dihydroimidazole; pyrroline; azetidine; perhydroindole; perhydroquinoline; perhydroisoquinoline or pyrrolidine ring; any of which may be optionally substituted with C$_1$–C$_{12}$ alkyl, halo, hydroxy, C$_1$–C$_{10}$ hydroxyalkyl, C$_1$–C$_5$ haloalkyl, C$_6$–C$_{10}$ aryl, C$_6$–C$_{10}$ aryl substituted with halo or C$_1$–C$_6$ alkyl, C$_7$–C$_{16}$ arylalkyl, C$_7$–C$_6$ arylalkyl substituted with halo or C$_1$–C$_6$ alkyl, nitro, halo-C$_1$–C$_{10}$ alkyl, C$_1$–C$_{10}$ alkoxy, C$_1$–C$_{10}$ alkylthio, C$_1$–C$_{10}$ alkylsulfonyl, phenoxy, phenoxy substituted with halo or C$_1$–C$_6$ alkyl, C$_2$–C$_{10}$ alkenyl or cyano; or R$^4$ and R$^6$ or R$^2$ and R$^6$ together with the nitrogen and carbon atoms to which they are bound form an aziridine; piperazine; morpholine, thiomorpholine; thiomorpholine sulfinyl; thiomorpholine sulfonyl; hexamethyleneimine; piperidine, tetrahydropyridine; pyrazole; imidazole; pyrrole; triazole, tetrahydropyrimidine; dihydroimidazole; pyrroline; azetidine; perhydroindole; perhydroquinoline; perhydroisoquinoline; or pyrrolidine ring; any of which may be optionally substituted with C$_1$–C$_{12}$ alkyl, hydroxy, C$_1$–C$_{10}$ hydroxyalkyl, C$_1$–C$_5$ haloalkyl, halo, C$_6$–C$_{10}$ aryl, C$_6$–C$_{10}$ aryl substituted with halo or C$_1$–C$_6$ alkyl, C$_7$–C$_{16}$ arylalkyl, C$_7$–C$_{16}$ arylalkyl substituted with halo or C$_1$–C$_6$, alkyl, nitro, halo-C$_1$–C$_{10}$-alkyl, C$_1$–C$_{10}$ alkoxy, C$_1$–C$_{10}$ alkylthio, C$_1$–C$_{10}$ alkylsulfonyl, phenoxy, phenoxy substituted with halo or C$_1$–C$_6$ alkyl, C$_2$–C$_{10}$ alkenyl or cyano; or R$^2$ and R$^4$ together with the carbon atoms to which they are bound form a C$_5$–C$_6$ cycloalkyl or cycloalkenyl ring; any of which may be optionally substituted with C$_1$–C$_{12}$ alkyl, hydroxy, C$_1$–C$_{10}$ hydroxyalkyl, C$_1$–C$_5$ haloalkyl, halo, C$_6$–C$_{10}$ aryl, C$_6$–C$_{10}$ aryl substituted with halo or C$_1$–C$_6$ alkyl, C$_7$–C$_{16}$ arylalkyl, C$_7$–C$_{16}$ arylalkyl substituted with halo or C$_1$–C$_6$ alkyl, nitro, halo-C$_1$–C$_{10}$ alkyl, C$_1$–C$_{10}$ alkoxy, C$_1$–C$_{10}$ alkylthio, C$_1$–C$_{10}$ alkylsulfonyl, phenoxy, phenoxy substituted with halo or C$_1$–C$_6$ alkyl, C$_2$–C$_{10}$ alkenyl or cyano; or R$^4$ and R$^5$ together form a 3–6 membered carbocyclic ring, optionally substituted with halogen, hydroxy, C$_1$–C$_6$ alkyl, C$_1$–C$_6$ alkoxy, C$_1$–C$_6$ alkylthio or N(R$^{10}$)(R$^{11}$) wherein R$^{10}$ and R$^{11}$ are each independently hydrogen or C$_1$–C$_{12}$ alkyl; and m is 0, 1 or 2;

or an agrochemically acceptable salt or hydrolyzable ester thereof;

with the proviso that when n is 0, R$^4$ and R$^5$ are both hydrogen and R$^6$ and R$^7$ are both —C$_2$H$_5$, R$^1$ is not —NH$_2$; and (B) an agrochemically acceptable carrier therefor.

In another aspect this invention is directed to a method of controlling the growth of plants comprising applying to the locus of such plants an herbicidally effective amount of a compound of the Formula (I):

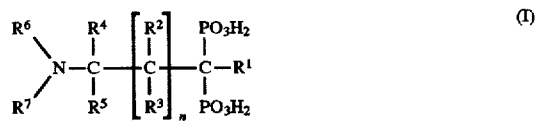

wherein n is 0, 1, 2, 3, 4, 5 or 6;

R$^1$ is hydrogen, hydroxy, C$_1$–C$_4$ alkoxy, halogen, C$_1$–C$_4$ alkyl, C$_1$–C$_4$ haloalkyl, hydroxy-C$_1$–C$_4$-alkyl, hydroxy-C$_1$–C$_4$-alkoxy or N(R$^8$)(R$^9$) wherein R$^8$ and R$^9$ are each independently hydrogen or C$_1$–C$_3$ alkyl;

each R$^2$, R$^3$, R$^4$ and R$^5$ is independently hydrogen; hydrocarbyl; substituted hydrocarbyl; hydrocarbyloxy; substituted hydrocarbyloxy; hydrocarbyl-S(O)$_m$—; or substituted hydrocarbyl-S(O)$_m$—;

R$^6$ and R$^7$ are each independently hydrogen; hydrocarbyl; substituted hydrocarbyl; hydrocarbyloxy; substituted hydrocarbyloxy; hydrocarbyl-S(O)$_m$—; substituted hydrocarbyl-S(O)$_m$—; pyridyl; substituted pyridyl; or are of the formula N(R$^{12}$)(R$^{13}$) wherein R$^{12}$ and R$^{13}$ are independently hydrogen, hydrocarbyl or substituted hydrocarbyl; or R$^6$ and R$^7$ together with the nitrogen to which they are bound form an aziridine; piperazine; morpholine; thiomorpholine; thiomorpholine sulfinyl; thiomorpholine sulfonyl; hexamethyleneimine; piperidine, tetrahydropyridine; pyrazole; imidazole; pyrrole; triazole; tetrahydropyrimidine; dihydroimidazole; pyrroline; azetidine; perhydroindole; perhydroquinoline; perhydroisoquinoline or pyrrolidine ring; any of which may be optionally substituted with C$_1$–C$_{12}$ alkyl, halo, hydroxy, C$_1$–C$_{10}$ hydroxyalkyl, C$_1$–C$_5$ haloalkyl, C$_6$–C$_{10}$ aryl, C$_6$–C$_{10}$ aryl substituted with halo or C$_1$–C$_6$ alkyl, C$_7$–C$_{16}$ arylalkyl sub-stituted with halo or C$_1$–C$_6$ alkyl, nitro, halo-C$_1$–C$_{10}$-alkyl, C$_1$–C$_{10}$ alkoxy, C$_1$–C$_{10}$ alkylthio, C$_1$–C$_{10}$ alkylsulfonyl, phenoxy, phenoxy substituted with halo or C$_1$–C$_6$ alkyl, C$_2$–C$_{10}$ alkenyl or cyano; or R$^4$ and R$^6$ or R$^2$ and R$^6$ together with the nitrogen and carbon atoms to which they are bound form an aziridine; piperazine; morpholine, thiomorpholine; thiomorpholine sulfinyl; thiomorpholine sulfonyl; hexamethyleneimine; piperidine, tetrahydropyridine; pyrazole; imidazole; pyrrole; triazole, tetrahydropyrimidine; dihydroimidazole; pyrroline; azetidine; perhydroindole; perhydroquinoline; perhydroisoquinoline; or pyrrolidine ring; any of which may be optionally substituted with C$_1$–C$_2$ alkyl, hydroxy, C$_1$–C$_{10}$ hydroxyalkyl, C$_1$–C$_5$ haloalkyl, halo, C$_6$–C$_{10}$ aryl, C$_6$–C$_{10}$ aryl substituted with halo or C$_1$–C$_6$ alkyl, C$_7$–C$_{16}$ arylalkyl, C$_7$–C$_{16}$ arylalkyl substituted with halo or C$_1$–C$_6$ alkyl, nitro, halo-C$_1$–C$_{10}$-alkyl, C$_1$–C$_{10}$ alkoxy, C$_1$–C$_{10}$ alkylthio, C$_1$–C$_{10}$ alkylsulfonyl, phenoxy, phenoxy substituted with halo or C$_1$–C$_6$ alkyl, C$_2$–C$_{10}$ alkenyl or cyano; or R$^2$ and R$^4$ together with the carbon atoms to which they are bound form a C$_5$–C$_6$ cycloalkyl or cycloalkenyl ring; any of which may be optionally substituted with C$_1$–C$_{12}$ alkyl, hydroxy, C$_1$–C$_{10}$ hydroxyalkyl, C$_1$–C$_5$ haloalkyl, halo, C$_6$–C$_{10}$ aryl, C$_6$–C$_{10}$ aryl substituted with halo or C$_1$–C$_6$ alkyl, C$_7$–C$_{16}$ arylalkyl, C$_7$–C$_{16}$ arylalkyl substituted with halo or C$_1$–C$_6$ alkyl, nitro, halo-C$_1$–C$_{10}$-alkyl, C$_1$–C$_{10}$ alkoxy, C$_1$–C$_{10}$ alkylthio, C$_1$–C$_{10}$ alkylsulfonyl, phenoxy, phenoxy substituted with halo or C$_1$–C$_6$ alkyl, C$_2$–C$_{10}$ alkenyl or cyano; or R$^4$ and R$^5$ together form a 3–6 membered carbocyclic ring, optionally substituted with halogen, hydroxy, $C_1$–$C_6$ alkyl, $C_1$–$C_6$ alkoxy, $C_1$–$C_6$ alkylthio or $N(R^{10})(R^{11})$ wherein $R^{10}$ and $R^{11}$ are each independently hydrogen or $C_1$–$C_{12}$ alkyl; and m is 0, 1 or 2;

or an agrochemically acceptable salt or hydrolyzable ester thereof;

with the proviso that when n is 0, $R^4$ and $R^5$ are both hydrogen and $R^6$ and $R^7$ are both —$C_2H_5$, $R^1$ is not —$NH_2$.

In yet another aspect, this invention is directed to novel aza-bisphosphonic acid compounds having a structure within the scope of Formula (I) above.

DETAILED DESCRIPTION OF THE PREFERRED EMBODIMENTS

The compounds employed in the herbicidal compositions of this invention are of the Formula (I):

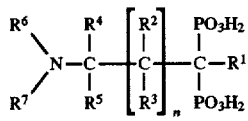

(I)

wherein n is 0, 1, 2, 3, 4, 5 or 6;

$R^1$ is hydrogen, hydroxy, $C_1$–$C_4$ alkoxy, halogen, $C_1$–$C_4$ alkyl, $C_1$–$C_4$ haloalkyl, hydroxy-$C_1$–$C_4$-alkyl, hydroxy-$C_1$–$C_4$-alkoxy or $N(R^8)(R^9)$ wherein $R^8$ and $R^9$ are each independently hydrogen or $C_1$–$C_3$ alkyl;

each $R^2$, $R^3$, $R^4$ and $R^5$ is independently hydrogen; hydrocarbyl; substituted hydrocarbyl; hydrocarbyloxy; substituted hydrocarbyloxy; hydrocarbyl-$S(O)_m$—; or substituted hydrocarbyl-$S(O)_m$—;

$R^6$ and $R^7$ are each independently hydrogen; hydrocarbyl; substituted hydrocarbyl; hydrocarbyloxy; substituted hydrocarbyloxy; hydrocarbyl-$S(O)_m$—; substituted hydrocarbyl-$S(O)_m$—; pyridyl; substituted pyridyl; or are of the formula $N(R^{12})(R^{13})$ wherein $R^{12}$ and $R^{13}$ are independently hydrogen, hydrocarbyl or substituted hydrocarbyl; or $R^6$ and $R^7$ together with the nitrogen to which they are bound form an aziridine; piperazine; morpholine; thiomorpholine; thiomorpholine sulfinyl; thiomorpholine sulfonyl; hexamethyleneimine; piperidine, tetrahydropyridine; pyrazole; imidazole; pyrrole; triazole; tetrahydropyrimidine; dihydroimidazole; pyrroline; azetidine; perhydroindole; perhydroquinoline; perhydroisoquinoline or pyrrolidine ring; any of which may be optionally substituted with $C_1$–$C_{12}$ alkyl, halo, hydroxy, $C_1$–$C_{10}$ hydroxyalkyl, $C_1$–$C_5$ haloalkyl, $C_6$–$C_{10}$ aryl, $C_6$–$C_{10}$ aryl substituted with halo or $C_1$–$C_6$ alkyl, $C_7$–$C_{16}$ arylalkyl, $C_7$–$C_{16}$ arylalkyl substituted with halo or $C_1$–$C_6$ alkyl, nitro, halo-$C_1$–$C_{10}$-alkyl, $C_1$–$C_{10}$ alkoxy, $C_1$–$C_{10}$ alkylthio, $C_1$–$C_{10}$ alkylsulfonyl, phenoxy, phenoxy substituted with halo or $C_1$–$C_6$ alkyl, $C_2$–$C_{10}$ alkenyl or cyano; or $R^4$ and $R^6$ or $R^2$ and $R^6$ together with the nitrogen and carbon atoms to which they are bound form an aziridine; piperazine; morpholine, thiomorpholine; thiomorpholine sulfinyl; thiomorpholine sulfonyl; hexamethyleneimine; piperidine, tetrahydropyridine; pyrazole; imidazole; pyrrole; triazole, tetrahydropyrimidine; dihydroimidazole; pyrroline; azetidine; perhydroindole; perhydroquinoline; perhydroisoquinoline; or pyrrolidine ring; any of which may be optionally substituted with $C_1$–$C_{12}$ alkyl, hydroxy, $C_1$–$C_{10}$ hydroxyalkyl, $C_1$–$C_5$ haloalkyl, halo, $C_6$–$C_{10}$ aryl, $C_6$–$C_{10}$ aryl substituted with halo or $C_1$–$C_6$ alkyl, $C_7$–$C_{16}$ arylalkyl, $C_7$–$C_{16}$ arylalkyl substituted with halo or $C_1$–$C_6$ alkyl, nitro, halo-$C_1$–$C_{10}$-alkyl, $C_1$–$C_{10}$ alkoxy, $C_1$–$C_{10}$ alkylthio, $C_1$–$C_{10}$ alkylsulfonyl, phenoxy, phenoxy substituted with halo or $C_1$–$C_6$ alkyl, $C_2$–$C_{10}$ alkenyl or cyano; or $R^2$ and $R^4$ together with the carbon atoms to which they are bound form a $C_5$–$C_6$ cycloalkyl or cycloalkenyl ring; any of which may be optionally substituted with $C_1$–$C_{12}$ alkyl, hydroxy, $C_1$–$C_{10}$ hydroxyalkyl, $C_1$–$C_5$ haloalkyl, halo, $C_6$–$C_{10}$ aryl, $C_6$–$C_{10}$ aryl substituted with halo or $C_1$–$C_6$ alkyl, $C_7$–$C_{16}$ arylalkyl, $C_7$–$C_{16}$ arylalkyl substituted with halo or $C_1$–$C_6$ alkyl, nitro, halo-$C_1$–$C_{10}$-alkyl, $C_1$–$C_{10}$ alkoxy, $C_1$–$C_{10}$ alkylthio, $C_1$–$C_{10}$ alkylsulfonyl, phenoxy, phenoxy substituted with halo or $C_1$–$C_6$ alkyl, $C_2$–$C_{10}$ alkenyl or cyano; or $R^4$ and $R^5$ together form a 3–6 membered carbocyclic ring, optionally substituted with halogen, hydroxy, $C_1$–$C_6$ alkyl, $C_1$–$C_6$ alkoxy, $C_1$–$C_6$ alkylthio or $N(R^{10})(R^{11})$ wherein $R^{10}$ and $R^{11}$ are each independently hydrogen or $C_1$–$C_{12}$ alkyl; and m is 0, 1 or 2;

or an agrochemically acceptable salt or hydrolyzable ester thereof;

with the proviso that when n is 0, $R^4$ and $R^5$ are both hydrogen and $R^6$ and $R^7$ are both —$C_2H_5$, $R^1$ is not —$NH_2$.

Preferably:

$R^1$ is hydrogen, hydroxy, halogen or $C_1$–$C_4$ alkyl;

$R^2$, $R^3$, $R^4$ and $R^5$ are independently hydrogen; $C_1$–$C_2$ alkyl; $C_2$–$C_{12}$ alkenyl; $C_2$–$C_{12}$ alkynyl; halo-$C_1$–$C_{12}$ alkyl, halo-$C_2$–$C_{12}$ alkenyl; halo-$C_2$–$C_{12}$-alkynyl; $C_6$–$C_{14}$ aralkyl; $C_1$–$C_{12}$ alkoxy; or $C_1$–$C_{12}$ alkylthio;

$R^6$ and $R^7$ are independently hydrogen; $C_1$–$C_{12}$ alkyl; $C_2$–$C_{12}$ alkenyl; $C_2$–$C_{12}$ alkynyl; halo-$C_1$–$C_{12}$ alkyl; halo-$C_2$–$C_{12}$ alkenyl; halo-$C_2$–$C_{12}$ alkynyl; pyridyl; substituted pyridyl; phenyl; substituted phenyl; $C_6$–$C_{14}$ aralkyl; substituted $C_6$–$C_{14}$ aralkyl; $C_1$–$C_{12}$ alkoxy or $C_1$–$C_{12}$ alkylthio; or $R^2$ and $R^4$ together with the carbon atoms to which they are bound form an optionally substituted $C_5$–$C_6$ cycloalkyl or cycloalkenyl ring; or $R^4$ and $R^6$ together with the nitrogen and carbon atoms to which they are bound form a 3- to 7-membered ring optionally substituted with halogen, hydroxy, $C_1$–$C_6$ alkyl, $C_1$–$C_6$ alkylthio or $C_7$–$C_{16}$ aralkyl; or $R^6$ and $R^7$ together with the nitrogen to which they are bound form a 3- to 7-membered ring, optionally substituted with halogen, hydroxy, $C_1$–$C_6$ alkoxy, nitro, $C_1$–$C_6$ alkyl, $C_7$–$C_{16}$ aralkyl or $C_1$–$C_6$ alkylthio groups; and n is 0, 1, 2 or 3.

More preferably, $R^1$ is hydrogen or hydroxy;

$R^2$ and $R^3$ are hydrogen;

$R^4$ and $R^5$ are each independently hydrogen, $C_1$–$C_8$ alkyl, $C_2$–$C_8$ alkenyl or $C_6$–$C_{10}$ aralkyl optionally substituted with halogen or hydroxy; and $R^6$ and $R^7$ are each independently hydrogen, $C_1$–$C_8$ alkyl, $C_2$–$C_8$ alkenyl, or $C_6$–$C_{10}$ aralkyl optionally substituted with halogen or hydroxy; or $R^4$ and $R^6$ together with the nitrogen and carbon atoms to which they are bound form a pyrrolidine or piperidine ring, either of which may be optionally substituted with halogen, hydroxy, $C_1-C_6$ alkoxy or $C_1-C_6$ alkyl; or $R^6$ and $R^7$ together with the nitrogen to which they are bound form a pyrrolidine or piperidine ring, either of which may be optionally substituted with halogen, hydroxy, $C_1-C_6$ alkoxy or $C_1-C_6$ alkyl; and n is 0 or 1.

Particularly preferred compounds for use in the herbicidal compositions and method of this invention include:

2-(R-alpha-methylbenzylamino)ethane-1,1-bisphosphonic acid;

2-(2-methylpropylamino)ethane-1,1-bisphosphonic acid;

2-[1-(4-methyl-1,3-imidazolyl)]ethane-1,1-bisphosphonic acid;

2-(1-pyrrolidinyl)ethane-1,1-bisphosphonic acid;

2-(piperidinyl)ethane-1,1-bisphosphonic acid;

2-(propylamino)ethane-1,1-bisphosphonic acid;

2-(N-methyl-N-ethylamino)ethane-1,1-bisphosphonic acid;

2-(n-butylamino)ethane-1,1-bisphosphonic acid;

2-(2-propenylamino)ethane-1,1-bisphosphonic acid;

2-[1-(1,2,3,6-tetrahydropyridinyl)]ethane-1,1-bisphosphonic acid; and 2-(N,N-dipropylamino)ethane-1,1-bisphosphonic acid;

3-(benzylamino)propane-1,1-bisphosphonic acid;

3-(1-pyrrolidino)propane-1,1-bisphosphonic acid;

3-(N-methyl-N-propylamino)propane-1,1-bisphosphonic acid;

3-(N-methyl-N-isobutylamino)propane-1,1-bisphosphonic acid;

3-(alpha-methylbenzylamino)propane-1,1-bisphosphonic acid;

3-(1-cyclohexylethylamino)propane-1,1-bisphosphonic acid;

(4-methyl-3-amino)pentane-1,1-bisphosphonic acid;

(4-methyl-3-benzylamino)pentane-1,1-bisphosphonic acid;

3-aminooctane-1,1-bisphosphonic acid;

4-(benzylamino)hexane-1,1-bisphosphonic acid;

2-(2-pyrrolidino)ethane-1,1-bisphosphonic acid;

2-(2-piperidino)ethane-1,1-bisphosphonic acid;

2-[2-(4-methyl)piperidino]ethane-1,1-bisphosphonic acid; and 2-(2-pyrrolidino)-1-hydroxyethane-1,1-bisphosphonic acid.

In another aspect, this invention is directed to certain classes of novel azabisphosphonic acid compounds within the scope of Formula 1.

One of such classes of novel aza-bisphosphonic acid compounds within the scope of this invention include those of the structural Formula II:

wherein $R^{14}$ and $R^{15}$ are each independently hydrogen, $C_1-C_6$ straight chain or branched alkyl, hydroxy, $C_3-C_6$ alkenyl, $C_1-C_6$ alkoxy or $C_1-C_6$ alkoxy-$C_1-C_6$ alkyl; and agriculturally acceptable salts thereof. Specific compounds within the scope of this genus include:

2-(N,N-di-n-butylamino)ethane-1,1-bisphosphonic acid;

2-(N,N-diethylamino)ethane-1,1-bisphosphonic acid;

2-(N,N-di-n-propylamino)ethane-1,1-bisphosphonic acid;

2-(propylamino)ethane-1,1-bisphosphonic acid;

2-(isopropylamino)ethane-1,1-bisphosphonic acid;

2-(propylamino)ethane-1,1-bisphosphonic acid, tetrabutylammonium salt;

2-(propylamino)ethane-1,1-bisphosphonic acid, tributylamine salt;

2-(t-butylamino)ethane-1,1-bisphosphonic acid;

2-(n-butylamino)ethane-1,1-bisphosphonic acid;

2-(n-hexylamino)ethane-1,1-bisphosphonic acid, tetrabutylammonium salt;

2-(but-3-enylamino)ethane-1,1-bisphosphonic acid;

2-(n-hexylamino)ethane-1,1-bisphosphonic acid;

2-(isobutylamino)ethane-1,1-bisphosphonic acid;

2-(n-ethylamino)ethane-1,1-bisphosphonic acid;

2-(prop-2-enylamino)ethane-1,1-bisphosphonic acid;

2-(methoxyamino)ethane-1. 1-bisphosphonic acid;

2-(N-methoxy-N-methylamino)ethane-1,1-bisphosphonic acid;

2-(N-hydroxy-N-methylamino)ethane-1,1-bisphosphonic acid; and 2-(2-ethoxyethylamino)ethane-1,1-bisphosphonic acid;

Novel aza-bisphosphonic acids within the scope of this invention also include those of Formula III:

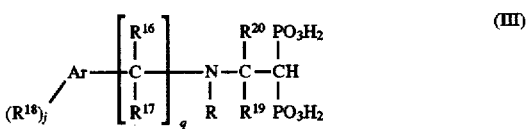

wherein q is 0–10; j is 0–3; $R^{16}$ and $R^{17}$ are each independently hydrogen or $C_1-C_6$ alkyl; Ar is benzene, pyridine, pyrimidine, pyridazine, naphthalene, pyrazole, imidazole, triazole, thiazole, furan, thiophene, pyrrole, oxazole or thiadiazole; $R^{18}$ is halo, $C_1-C_{10}$ alkyl, aryl, substituted aryl, benzyl, substituted benzyl, nitro, halo-$C_1-C_{10}$-alkyl, $C_1-C_{10}$ alkoxy, $C_1-C_{10}$ alkylthio, $C_1-C_{10}$ alkylsulfenyl, phenoxy, substituted phenoxy, $C_2-C_{10}$ alkenyl or cyano; and $R^{19}$, $R^{10}$ and $R^{21}$ are each independently hydrogen, $C_1-C_{10}$ alkyl, $C_1-C_{10}$ substituted alkyl, $C_7-C_{10}$ aralkyl or $C_2-C_{10}$ alkenyl; and agriculturally acceptable salts thereof.

When q is 2 or more, each $R^{16}$ and $R^{17}$ may themselves independently be hydrogen or $C_1-C_3$ alkyl. Similarly, when j is 2 or more, each $R^{18}$ may be the same or different.

Specific compounds within the scope of this genus include:

2-(alpha-methylbenzylamino)ethane-1,1-bisphosphonic acid:

2-(2-methylbenzylamino)ethane-1,1-bisphosphonic acid;

2-(3-methylbenzylamino)ethane-1,1-bisphosphonic acid;

2-(2-phenylethylamino)ethane-1,1-bisphosphonic acid;

2-(benzylamino)ethane-1,1-bisphosphonic acid;

2-(S-alpha-methylbenzylamino)ethane-1,1-bisphosphonic acid; and 2-(R-alpha-methylbenzylamino)ethane-1,1-bisphosphonic acid, tetrabutyl ammonium salt.

Yet another novel genus of compounds within the scope of this invention are compounds of Formula (IV):

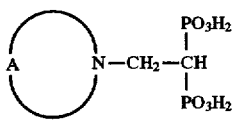

wherein A is an alkylenidene radical of 3–6 carbon atoms optionally substituted with $C_1$–$C_6$ alkyl, and agriculturally acceptable salts thereof. Specific compounds within the scope of this genus include:

2-(1-pyrrolidinyl)ethane-1,1-bisphosphonic acid;

2-(2,5-dimethyl-1-pyrrolidinyl)ethane-1,1-bisphosphonic acid;

2-(1-pyrrolidinyl)ethane-1,1-bisphosphonic acid, tetramethylammonium salt;

2-(1-pyrrolidinyl)ethane-1,1-bisphosphonic acid tributylamino salt;

2-(1-pyrrolidinyl)ethane-1,1-bisphosphonic acid trimethylsulfonium salt;

2-(1-hexamethyleneiminyl)ethane-1,1-bisphosphonic acid;

2-(4-methyl-1-piperidinyl)ethane-1,1-bisphosphonic acid;

2-(2-methyl-1-piperidinyl)ethane-1,1-bisphosphonic acid; and 2-(3-methyl-1-piperidinyl)ethane-1,1-bisphosphonic acid.

Another novel genus of compounds within the scope of this invention are those of Formula (V):

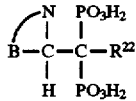

wherein $R^{22}$ is hydrogen or hydroxyl; and B is a $C_2$–$C_4$ alkylidene linking group, optionally substituted with $C_1$–$C_6$ alkyl; and agriculturally acceptable salts thereof.

Specific compounds within the scope of this genus include:

1-(2-piperidinyl)-1-hydroxymethane-1,1-bisphosphonic acid;

1-(2-pyrrolidinyl)-1-hydroxymethane-1,1-bisphosphonic acid; and 1-(2-pyrrolidinyl)-1-hydroxymethane-1,1-bisphosphonic acid.

Another class of compounds within the scope of this invention are those of Formula VI:

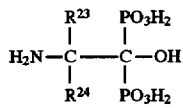

wherein $R^{23}$ and $R^{24}$ are each independently C1–C6 alkyl or together constitute a $C_3$–$C_5$ alkylidene group optionally substituted with $C_1$–$C_6$ alkyl; and agrochemically acceptable salts thereof.

Illustrative compounds within the scope of this invention include:

2-amino-1-hydroxy-2-methylpropane-1,1-bisphosphonic acid, hydrochloride salt; and 1-(1-aminocyclopentyl)-1-hydroxymethane-1,1-bisphosphonic acid.

Yet another novel genus of compounds within the scope of this invention are compounds of Formula (VII):

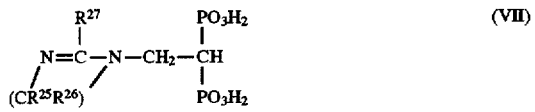

wherein t is 2, 3 or 4; $R^{25}$ and $R^{26}$ are each independently hydrogen, $C_1$–$C_{10}$ alkyl, halo, nitro, $C_1$–$C_9$ alkoxy, $C_1$–$C_{10}$ aralkyl, cyano, trifluoromethyl or represent a unit of unsaturation; and $R^{27}$ is hydrogen, $C_1$–$C_6$ alkyl, $C_7$–$C_{10}$ aralkyl, halo, nitro, trifluoromethyl or cyano. Each $R^{25}$ and $R^{26}$ may themselves be different members of the group listed above.

Illustrative compounds within the scope of this invention include:

2-[1-(2-methyl-1,4,5,6 tetrahydro-1,3-pyrimidinyl)]ethane-1,1,bisphosphonic acid; and 2-[1-(4-methyl-1,3-imidazolyl)]ethane-1,1-bisphosphonic acid.

In still another aspect, this invention is directed to novel aza-bisphosphonic acid compounds of the Formula (VIII):

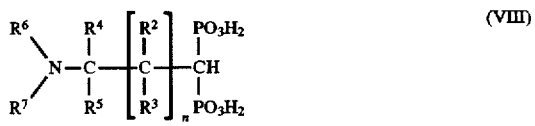

wherein n is 1, 2, 3, 4, 5 or 6;

each $R^2$, $R^3$, $R^4$ and $R^5$ is independently hydrogen; hydrocarbyl; substituted hydrocarbyl; hydrocarbyloxy,; substituted hydrocarbyloxy; hydrocarbyl-S(O)$_m$—; or substituted hydrocarbyl-S(O)$_m$—;

$R^6$ and $R^7$ are each independently hydrogen; hydrocarbyl; substituted hydrocarbyl; hydrocarbyloxy; substituted hydrocarbyloxy; hydrocarbyl-S(O)$_m$—; substituted hydrocarbyl-S(O)$_m$—; pyridyl; substituted pyridyl; or are of the formula N($R^{10}$)($R^{11}$) wherein $R^{10}$ and $R^{11}$ are independently hydrogen, hydrocarbyl or substituted hydrocarbyl; or $R^2$ and $R^4$ or $R^4$ and $R^6$ or $R^6$ and $R^7$ or $R^4$ and $R^5$ form an optionally substituted 3- to 7-membered ring as defined above;

m is 0, 1 or 2; and agrochemically acceptable salts thereof;

with the proviso that when n is 1, at least one of $R^2$, $R^3$, $R^4$, $R^5$, $R^6$ and $R^7$ is not H.

Preferred novel compounds of Formula VIII are those in which n is 1, 2 or 3;

$R^2$, $R^3$, $R^4$ and $R^5$ are each independently hydrogen; $C_1$–$C_{12}$ alkyl; $C_2$–$C_{12}$ alkenyl; $C_2$–$C_{12}$ alkynyl; halo-$C_1$–$C_{12}$-alkyl; halo-$C_2$–$C_{12}$-alkenyl; halo-$C_2$–$C_{12}$-alkynyl; $C_6$–C14 aralkyl; $C_1$–$C_{12}$ alkoxy; or $C_1$–$C_{12}$ alkylthio;

$R^6$ and $R^7$ are each independently hydrogen; $C_1$–$C_{12}$ alkyl; $C_2$–$C_{12}$ alkenyl; $C_2$–$C_{12}$ alkynyl; halo-$C_1$–$C_{12}$-alkyl; halo-$C_2$–$C_{12}$-alkenyl; halo-$C_2$–$C_{12}$-alkynyl; $C_6$–$C_{14}$ aralkyl; $C_1$–$C_{12}$ alkoxy; or $C_1$–$C_{12}$ alkylthio; or $R^2$ and $R^4$ together with the carbon atoms to which they are bound form an optionally substituted $C_5$–$C_6$ cycloalkyl or cycloalkenyl ring; or $R^6$ and $R^7$ together with the nitrogen to which they are bound form a 3- to 7-membered ring, optionally substituted with halogen, hydroxy, $C_1$–$C_6$ alkyl; $C_1$–$C_6$ alkylthio or $C_6$–$C_{10}$ aralkyl;

and agrochemically acceptable salts and hydrolyzable esters thereof.

More preferred novel compounds of Formula (VIII) are those wherein:

n is 1;

$R^2$ and $R^3$ are each hydrogen;

$R^4$ and $R^5$ are each independently hydrogen; $C_1$–$C_8$ alkyl; $C_2$–$C_8$ alkenyl; or $C_6$–$C_{10}$ aralkyl optionally substituted with halogen or hydroxy;

$R^6$ and $R^7$ are each independently hydrogen; $C_1$–$C_8$ alkyl; $C_2$–$C_8$ alkenyl; or $C_6$–$C_{10}$ aralkyl optionally substituted with halogen or hydroxy; or $R^6$ and $R^7$ together with the nitrogen to which they are bound form a piperidine or pyrrolidine ring optionally substituted with halogen, hydroxy, $C_1$–$C_6$ alkyl, $C_1$–$C_6$ alkylthio or $C_6$–$C_{10}$ aralkyl.

Specific compounds within the scope of this genus include:

3-(benzylamino)propane-1,1-bisphosphonic acid;

3-(1-pyrrolidino)propane-1,1-bisphosphonic acid;

3-(N-methyl-N-propylamino)propane-1,1-bisphosphonic acid;

3-(N-methyl-N-isobutylamino)propane-1,1-bisphosphonic acid;

3-(alphamethylbenzylamino)propane-1,1-bisphosphonic acid;

3-(1-cyclohexylethylamino)propane-1,1-bisphosphonic acid;

(4-methyl-3-amino)pentane-1,1-bisphosphonic acid;

(4-methyl-3-benzylamino)pentane-1,1-bisphosphonic acid;

3-aminooctane-1,1-bisphosphonic acid;

4-(benzylamino)hexane-1,1-bisphosphonic acid; and 2-(2-pyrrolidino)ethane-1,1-bisphosphonic acid.

The formulae given above are intended to include tautomeric forms of the structures drawn therein, as well as physically distinguishable modifications of the compounds which may arise, for example, from different ways in which the molecules are arranged in a crystal lattice, or from the inability of parts of the molecule to rotate freely in relation to other parts, or from geometrical isomerism, or form intra-molecular or inter-molecular hydrogen bonding, or otherwise.

The compounds of such formulae can exist in enantiomeric forms. The invention includes both individual enantiomers and mixtures of the two in all proportions.

As is employed herein, the term "hydrocarbyl", whether representing a substituent on its own or whether it is part of the definition of a larger group (e.g., as in hydrocarbyloxy, hydrocarbyl-S(O)$_m$—, etc.) is intended to include hydrocarbon groups having from 1 to 16 carbon atoms. The term hydrocarbyl therefore includes, for example, $C_1$ to $C_6$ alkyl including both straight and branched chain isomers (e.g., methyl, ethyl, propyl, isopropyl, sec-hexyl and hexyl); cycloalkyl of 3 to 16 carbon atoms (e.g., cyclopropyl, cyclobutyl and cyclohexyl); $C_2$ to $C_{16}$ alkenyl including for example allyl and crotyl; $C_2$ to $C_{16}$ alkynyl (e.g. propynyl); phenyl; phenylalkyl; alkylphenyl, alkenylphenyl, alkynylphenyl, alkylbenzyl, alkenylbenzyl, alkynyl benzyl, naphthyl and the like.

The term "substituted" when applied to the term "hydrocarbyl" (or to a similar term unless specifically defined otherwise) is intended to include hydrocarbyl groups, as defined above, having one or more substituents selected from the group consisting of halogen (i.e., fluorine, chlorine, bromine, and iodine); $C_1$–$C_{10}$ alkyl, $C_1$–$C_{10}$ alkoxy, $C_1$–$C_{10}$ alkyl-S(O)$_m$—, nitro, cyano, or $CF_3$ groups. In the above definitions, m is 0, 1 or 2.

Further, when the hydrocarbyl radical is a substituted aryl radical (e.g., phenyl, benzyl or naphthyl), the substituents may include one or more of the substituents listed in the last foregoing paragraph. The term "substituted pyridyl" is intended to include those substituents detailed above for substituted aryl radicals.

In addition, unless specified otherwise, the term "alkyl" is intended to include straight chain, branched and cycloalkyl compounds. The above definitions the term "halogen" includes fluoro, chloro, bromo and iodo groups. In polyhalogenated groups the halogens may be the same or different.

The compounds of the present invention have been found to be active herbicides, possessing utility as postemergence herbicides and useful against a wide range of plant species including broadleaf and grassy species.

This invention therefore also relates to a method for controlling undesirable vegetation comprising applying to a locus where control of such vegetation is desired subsequent to the emergence of such vegetation a herbicidally effective amount of a compound as described herein, together with an inert diluent or carrier suitable for use with herbicides. The terms "herbicide" and "herbicidal" are used herein to denote the inhibitive control or modification of undesired plant growth. Inhibitive control and modification include all deviations from natural development such as, for example, total killing, growth retardation, defoliation, desiccation, regulation, stunting, tillering, stimulation, leaf burn and dwarfing. The term "herbicidally effective amount" is used to denote any amount which achieves such control or modification when applied to the undesired plants themselves or to the area in which these plants are growing. The term "plants" is intended to include germinated seeds, emerging seedlings and established vegetation, including both roots and above-ground portions.

The term "agriculturally acceptable salt" is easily determined by one of ordinary skill in the art and includes alkali metal, ammonium, phosphonium, sulfonium salts, organic derivatives thereof, and the like.

The compounds of this invention wherein $R^1$ is hydrogen and n is 0 may generally be prepared by reacting tetraethyl vinylidene bisphosphonate with an appropriate amine. Such reaction is typically carried out at between about 0° and about 100° C. in the presence of a suitable nonreactive solvent, such as acetonitrile, diethyl ether, toluene, tetrahydrofuran, and the like. The ester groups may then be removed using bromotrimethylsilane or aqueous hydrochloric acid.

Tetraethyl vinylidene bisphosphonate may be prepared in accordance with the method disclosed by C. Degenhardt et al., J. Org. Chem., Vol 51, pp 3488–3490 (1986). The amines employed are either commercially available or may be prepared by means well known to one of skill in the art, e.g., preparation from the corresponding bromides by a Gabriel Synthesis (see Vogel, "A Textbook of Practical Organic Chemistry", 3d Ed., pp 569).

The compounds of this invention wherein $R^1$ is hydrogen and n is not 0 may be generally prepared by alkylation of tetraethyl methylene bisphosphonate with a substituted alkyl halide, such as allyl bromide, ethyl bromoacetate or N,N-dimethyl chloroacetamide and subsequent conversion of the olefin, ester or amide to an amine and hydrolysis of the phosphonate esters to phosphonic acids.

Alternatively, for compounds where $R^1$=H and n=1, the compounds may be prepared by adding a nitroalkane to vinylidine bisphosphonate. This intermediate nitro compound may be reduced to the primary amine from which various substituted amines can be produced by reductive alkylation. On the other hand, the nitro group may be hydrolyzed to give a ketone which can be reductively aminated to give various amines.

For the production of compounds wherein the amine contains sensitive groups, the phosphonate ester groups may first be transesterified by the use of a compound such as bromotrimethylsilane. Such groups can be subsequently unblocked by hydrolysis with water.

Alternatively, for producing compounds wherein $R^1$ is other than H, the appropriate carboxylic acid, amide or nitrile can be converted employing $PCl_3$ and phosphorous acid or $P_2O_3$ utilizing means well known to those of skill in the art.

The compositions of this invention comprise a compound of Formula (I) above and a suitable carrier, which carriers are well known to one of ordinary skill in the art.

The compounds of the present invention are useful as herbicides and can be applied in a variety of ways known to those skilled in the art, at various concentrations. The compounds are useful in controlling the growth of undesirable vegetation by post-emergent application to the locus where control is desired. In practice, the compounds are applied as formulations containing the various adjuvants and carriers known to or used in the industry for facilitating dispersion. The choice of formulation and mode of application for any given compound may affect its activity, and selection will be made accordingly. The compounds of the invention may thus be formulated as wettable powders, as emulsifiable concentrates, as powders or dusts, as flowables, as solutions, suspensions or emulsions, or in controlled-release forms such as microcapsules. These formulations may contain as little as about 0.5% to as much as about 95% or more by weight of active ingredient. The optimum amount for any given compound will depend upon the nature of plants to be controlled. The rate of application will generally vary from about 0.01 to about 10 pounds per acre, preferably from about 0.02 to about 4 pounds per acre.

Wettable powders are in the form of finely divided particles which disperse readily in water or other liquid carriers. The particles contain the active ingredient retained in a solid matrix. Typical solid matrices include fuller's earth, kaolin clays, silicas and other readily wettable organic or inorganic solids. Wettable powders normally contain about 5% to about 95% of the active ingredient plus a small amount of wetting, dispersing, or emulsifying agent.

Emulsifiable concentrates are homogeneous liquid compositions dispersible in water or other liquid, and may consist entirely of the active compound with a liquid or solid emulsifying agent, or may also contain a liquid carrier, such as xylene, heavy aromatic naphthas, isophorone and other nonvolatile organic solvents. In use, these concentrates are dispersed in water or other liquid and normally applied as a spray to the area to be treated. The amount of active ingredient may range from about 0.5% to about 95% of the concentrate.

Dusts are free-flowing admixtures of the active ingredient with finely divided solids such as talc, clays, flours and other organic and inorganic solids which act as dispersants and carriers.

Microcapsules are typically droplets or solutions of the active material enclosed in an inert porous shell which allows escape of the enclosed material to the surrounds at controlled rates. Encapsulated droplets are typically about 1 to 50 microns in diameter. The enclosed material typically constitutes about 50 to 95% of the weight of the capsule, and may include solvent in addition to the active compound. Shell of membrane materials include natural and synthetic rubbers, cellulosic materials, styrene-butadiene copolymers, polyacrylonitriles, polyacrylates, polyesters, polyamides, polyureas, polyurethanes and starch xanthates.

Other useful formulations for herbicidal applications include simple solutions of the active ingredient in a solvent in which it is completely soluble at the desired concentration, such as water, acetone, alkylated naphthalenes, xylene and other organic solvents. Pressurized sprayers, wherein the active ingredient is dispersed in finely-divided form as a result of vaporization of a low boiling dispersant solvent carrier may also be used.

Many of these formulations include wetting, dispersing or emulsifying agents. Examples are alkyl and alkylaryl sulfonates and sulfates and their salts; polyhydric alcohols; polyethoxylated alcohols; esters and fatty amines. These agents when used normally comprise from 0.1% to 15% by weight of the formulation.

Each of the above formulations can be prepared as a package containing the herbicide together with other ingredients of the formulation (diluents, emulsifiers, surfactants, etc.). The formulations can also be prepared by a tank mix method, in which the ingredients are obtained separately and combined at the grower site.

The compounds of the present invention are also useful when combined with other herbicides and/or defoliants, desiccants, growth inhibitors, and the like. These other materials can comprise from about 5% to about 95% of the active ingredients in the formulations. These combinations frequently provide a higher level of effectiveness in controlling weeds and often provide results unattainable with separate formulations of the individual herbicides.

Examples of other herbicides, defoliants, desiccants and plant growth inhibitors with which the compounds of this invention can be combined are:

A. Benzo-2,1,3-thiadiazin-4-one-2,2-dioxides such as bentazone;

B. hormone herbicides, particularly the phenoxyalkanoic acids such as MCPA, MCPA-thioethyl, dichlorprop, 2,4,5-T, MCPB, 2,4-D,2,4-DB, mecoprop, trichlopyr, fluroxypyr, clopyralid, and their derivatives (e.g. salts, esters and amides);

C. 1,3-dimethylpyrazole derivatives such as pyrazoxyfen, pyrazolate and benzofenap;

D. Dinitrophenols and their derivatives (e.g. acetates such as DNOC, dinoterb, dinoseb and its ester, dinoseb acetate;

E. dinitroaniline herbicides such as dinitramine, trifluralin, ethalfluralin, pendimethalin; and oryzalin;

F. arylurea herbicides such as diuron, flumeturon, metoxuron, neburon, isoproturon, chlorotoluron, chloroxuron, linuron, monolinuron, chlorobromuron, daimuron, and methabenzthiazuron;

G. phenylcarbamoyloxyphenylcarbamates such as phenmedipham and desmedipham;

H. 2-phenylpyridazin-3-ones such as chloridazon, and norflurazon;

I. uracil herbicides such as lenacil, bromacil and termacil;

J. triazine herbicides such as atrazine, simazine, aziprotryne, cyanazine, prometryn, dimethametryn, simetryne, and terbutryn;

K. phosphorothioate herbicides such as piperophos, bensulide, and butamifos;

L. thiolcarbamate herbicides such as cycloate, vernolate, molinate, thiobencarb, butylate*, EPTC*, triallate, diallate, ethyl esprocarb, tiocarbazil, pyridate, and dimepiperate;

M. 1,2,4-triazin-5-one herbicides such as metamitron and metribuzin;

N. benzoic acid herbicides such as 2,3,6-TBA, dicamba and chloramben;

O. anilide herbicides such as pretilachlor, butachlor, the corresponding alachlor, the corresponding compound propachlor, propanil, metazachlor, metolachlor, acetochlor, and dimethachlor;

P. dihalobenzonitrile herbicides such as dichlobenil, bromoxynil and ioxynil;

Q. haloalkanoic herbicides such as dalapon, TCA and salts thereof;

R. Diphenylether herbicides such as lactofen, flurogly-cofen or salts or esters thereof, nitrofen, bifenox, acifluorfen and salts and esters thereof, oxyfluorfen and fomesafen; chlornitrofen and chlomethoxyfen;

S. phenoxyphenoxypropionate herbicides such as diclofop and esters thereof such the methyl ester, fluazifop and esters thereof, haloxyfop and esters thereof, quizalofop and esters thereof and fenoxaprop and esters thereof such as the ethyl ester;

T. triketone and cyclohexanedione herbicides such as alloxydim and salts thereof, sethoxydim, cycloxydim, sulcotrione, tralkoxydim, and clethodim;

U. Sulfonyl urea herbicides such as chlorosulfuron, sulfometuron, metsulfuron and esters thereof; benzsulfuron and esters thereof such as the ester thereof methyl, DPX-M6313, chlorimuron and esters such as the ethyl ester thereof, pirimisulfuron and esters such as the methyl ester thereof, DPX-LS300 and pyrazosulfuron;

V. Imidazolidinone herbicides such as imazaquin, imazamethabenz, imazapyr and isopropylammonium salts thereof, imazathapyr;

W. arylanilide herbicides such as flamprop and esters thereof, benzoylpropethyl, diflufenican;

X. amino acid herbicides such as glyphosate and gluyfosinate and their salts and esters, sulphosate, and bilanafos;

Y. organoarsenical herbicides such as MSMA;

Z. herbicidal amide derivative such as napropamide, propyzamide, carbetamide, tebutam, bromobutide, isoxaben, naproanilide, diphenamid, and naptalam;

AA. miscellaneous herbicides including ethofumesate, cinmethylin, difenzoquat and salts thereof such as the methyl sulfate salt, clomazone, oxadiazon, bromofenoxim, barban, tridiphane, (in the ratio 3:1) flurochloridone, quinchlorac and mefanacet;

BB. examples of useful contact herbicides include bipyridylium herbicides such as those in which the active entity is paraquat and those in which the active entity is diquat. * These compounds are preferably employed in combination with a safener such as 2,2-dichloro-N, N-di-2-propenylacdtamide (dichlormid).

These formulations can be applied to the areas where control is desired by conventional methods. Dust and liquid compositions, for example, can be applied by the use of powerdusters, boom and hand sprayers and spray dusters.

The formulations can also be applied from airplanes as a dust or a spray or by rope wick applications.

The following are examples of typical formulations:

| 5% dust: | 5 parts active compound |
| --- | --- |
| | 95 parts talc |
| 2% dust: | 2 parts active compound |
| | 1 part highly dispersed silicic acid |
| | 97 parts talc |

These dusts are formed by mixing the components then grinding the mixture to the desired particle size.

| Wettable powders: | |
| --- | --- |
| 70%: | 70 parts active compound |
| | 5 parts sodium dibutylnaphthylsulfonate |
| | 3 parts naphthalenesulfonic acid/phenolsulfonic acid/phenol-sulfonic acid/formaldehyde condensate (3:2: 1) |
| | 10 parts kaolin |
| | 12 parts Champagne chalk |
| 40%: | 40 parts active compound |
| | 5 parts sodium lignin sulfonate |
| | 1 part sodium dibutylnaphthalene sulfonic acid |
| | 54 parts silicic acid |
| 25% | 25 parts active compound |
| | 4.5 parts calcium lignin sulfate |
| | 1.9 parts Champagne chalk/-hydroxyethyl cellulose (1:1) |
| | 8.3 parts sodium aluminum silicate |
| | 16.5 parts kieselguhr |
| | 46 parts kaolin |
| 10% | 10 parts active compound |
| | 3 parts of a mixture of sodium salts of saturated fatty alcohol sulfates |
| | 5 parts naphthalenesulfonic acid/formaldehyde condensate |
| | 82 parts kaolin |

These wettable powders are prepared by intimately mixing the active compounds with the additives in suitable mixers, and grinding the resulting mixture in mills or rollers.

| Emulsifiable concentrate: | |
| --- | --- |
| 25% | 25 parts active substance |
| | 2.5 parts epoxidized vegetable oil |
| | 10 parts of an akylarylsulfonate/fatty alcohol polyglycol ether mixture |
| | 57.5 parts xylene |

The amount of the present compositions which constitute a herbicidally effective amount depends upon the nature of the seeds or plants to be controlled. The rate of application of active ingredients varies from about 0.01 to about 25 pounds per acre, preferably about 0.10 to about 10 pounds per acre with the actual amount depending on the overall costs and the desired results. It will be readily apparent to one skilled in the art that compositions exhibiting lower herbicidal activity will require a higher dosage than more active compounds for the same degree of control.

EXAMPLES

The following examples are intended to further illustrate the present invention and are not intended to limit the scope of this invention in any manner whatsoever.

Example 1

Preparation of 2-[1-(1,2,4-triazole)]ethane-1,1-bisphosphonic acid (Compound No. 3)

One gram of 1,2,4-triazole was dissolved in 40 ml of THF and cooled to $-78°$ C. in a nitrogen atmosphere. n-Butyllithium (974 mg) was then added dropwise and the resultant white suspension stirred at −78° C. for five minutes. After warming to room temperature, the mixture was stirred for 45 minutes and then cooled again to −78° C. Tetraethyl vinylidinebiphosphonate (4.78 gm) was then added dropwise over a 20 minute period. When the addition was complete, the mixture was stirred for 15 minutes at −78° C., then warmed to 0° C. and stirring continued for one hour. The reaction was quenched with 10 ml of water and the THF removed under reduced pressure to give the crude product which was then combined with 35 ml of aqueous $K_2CO_3$ solution. The resulting mixture was extracted with 3×100 ml portions of dichloromethane. The extracts were combined, dried ($MgSO_4$), and the solvent removed under reduced pressure to afford a mobile oil. Column chromatography on silica gel with 10% methanol/dichloromethane provided 1.3 gm of tetraethyl 2-[1-(1,2,4-triazole)ethane-1,1-bisphosphonate. Hydrolysis of this material to form Compound No. 3 was achieved by heating a dichloromethane solution of the tetraethyl ester and 500 mol% of bromotrimethylsilane at 45° C. for four hours and then removing the volatiles in vacuo. Refluxing the residual oil with water for 30 minutes followed by cooling to room temperature and removal of the water under high vacuum resulted in the isolation of Compound No. 3 in quantitative yield.

Example 2

Preparation of 1-hydroxy-(2-amino-2-methyl) propane-1,1-bisphosphonic acid (Compound No. 8)

To a three-necked 250 ml round-bottomed flask equipped with a condenser, mechanical stirrer, oil bath and thermometer were added 2.37 gm of 2-aminoisobutyric acid, 85 ml of chlorobenzene and 3.2 gm of phosphorous acid. The mixture was heated at reflux for one hour and then cooled to 50° C. Phosphorus trichloride (9.62 gm) was then added and the mixture again heated to refluxing with stirring for five hours. At the end of this time, the mixture was allowed to cool to room temperature and the chlorobenzene carefully decanted. Fresh chlorobenzene (85 ml) and 80 ml of 6N HCl were then added and the mixture heated to refluxing with stirring. After six hours, the yellowish suspension was cooled to room temperature, vacuum filtered through dicalite, and the volatiles removed under high vacuum to afford a colorless syrup. Trituration with ethanol under steam heating provided 3.09 gm of Compound No. 8 as a white solid after isolation by vacuum filtration.

Example 3

Preparation of 1-hydroxy-1-(2-pyrrolidino)-1,1-bisphosphonic acid (Compound No. 9)

To a 200 ml three-necked flask equipped with a mechanical stirrer and reflux condenser carrying a nitrogen bubbler were added 4 gm of proline; 5.7 gm. of phosphorous acid and 25 ml of dioxane. Phosphorus trichloride (9.6 gm) was then added dropwise at 80° C. and the mixture stirred at 80° C. for two hours. After cooling the reaction mixture to room temperature, water (150 ml) was added and the resulting mixture was filtered through activated carbon. The filtrate was evaporated under reduced pressure and the residual clear oil placed in a vacuum oven (60° C.) overnight. At the end of this time the residue was triturated with EtOH and the resulting white solid isolated by vacuum filtration. Drying the solid in a vacuum oven at 60° C. afforded 5.9 gm. of Compound No. 9.

Example 4

Preparation of 2-(but-3-enylamino)ethane-1,1-bisphosphonic acid (Compound No. 29)

A solution of 1.08 gm of 1-aminobut-3-ene in five ml of methanol was added to 3.8 gm of tetraethyl vinylidinebisphosphonate at room temperature. After the resulting mixture had stirred overnight, an additional 0.12 gm. of 1-aminobut-3-ene was added and the stirring continued for an additional four hours. The reaction mixture was then concentrated under reduced pressure to yield 4.56 gm of tetraethyl 2-(but-3-enylamino)ethane-1,1-bisphosphonate. A 4.4 gm sample of this material was combined with five ml of acetonitrile and 7.2 ml of bromotrimethylsilane. After stirring at room temperature for 48 hours, the solution was heated to refluxing for four hours and then concentrated under reduced pressure. The resulting tetra(trimethylsilyl) ester was hydrolyzed by refluxing with 25 ml of water for 30 minutes. Removal of the volatile materials by lyophylization afforded 3.2 gm of Compound No. 29 as a stiff, colorless, hygroscopic foam.

Example 5

Preparation of 2-(3-methyl-1-piperidinyl)ethane-1,1-bisphosphonic acid (Compound No. 37)

A solution of one ml of 3-methylpiperidine in five ml of methanol was added dropwise to 2.43 gm of tetraethyl vinylidinebisphosphonate at room temperature. The reaction was stirred overnight and the mixture then concentrated under reduced pressure to yield 3.4 grams of tetraethyl 2-(3-methyl-1-piperidinyl)ethane-1,1-bisphosphonate. A portion of this material (3.37 gm) was dissolved in five ml of acetonitrile followed by the addition of five ml of bromotrimethylsilane. The resulting mixture was refluxed overnight, then allowed to cool to room temperature, and then concentrated under reduced pressure. Water (25 ml) was added to the residual oil and the mixture stirred for three hours. Removal of the water and other volatile components under high vacuum afforded 2.84 gm of Compound No. 37 as a stiff, hygroscopic, colorless foam.

Example 6

Preparation of 2-(4 methylbenzylamino)ethane-1,1-bisphosphonic acid (Compound No. 66)

To a 100 ml boiling flask were added 3.5 gm of tetraethyl vinylidine-1,1-bisphosphonate, 20 ml of acetonitrile, and 1.5 gm of 4-methylbenzylamine. The resulting mixture was magnetically stirred overnight at room temperature. At the end of this time, the solvent was removed under reduced pressure to give 4.66 gm of tetraethyl 2-(4-methylbenzylamino)ethane-1,1-bisphosphonate. A portion of this material (3.87 gm) was placed in a 100 ml boiling flask equipped with a magnetic stirrer and refluxed for four hours with 25 ml of concentrated HCl. Removal of the volatile materials under high vacuum afforded 3.21 gm of Compound No. 67 as a colorless, hygroscopic glass.

Example 7

Preparation of 3-(dipropylamino)propane-1,1-bisphosphonic acid (Compound No. 155)

A. Preparation of 3,3-bis(diethoxylphosphinyl)-propanoic acid

A solution of NaOH (4.00 g, 100 mmol) in water (50 ml) was added to a solution of ethyl 3,3-bis(diethoxyphosphinyl) propionate (32.6 g, 87 mmol) in EtOH (100 ml), and heated at 80° C. for 1 hour. After cooling, the EtOH was evaporated, and the residue was acidified to methyl orange with 12N HCl. The product was extracted into dichloromethane (5×50 ml). The organic layer was dried ($Na_2SO_4$) and concentrated to give the title compound (28.8 g, 96%) as a viscous oil.

B. Preparation of N,N-dipropyl-3,3-bis(diethoxyphosphinyl)propionamide

To a solution of 3,3-bis(diethoxyphosphinyl)-propanoic acid (1.5 g, 4.34 mmol) and dimethylformamide (2 drops) in dichloromethane (10 ml) was added oxalyl chloride (0.61 g., 4.77 mmol). The solution was stirred at ambient temperature until gas evolution ceased (~1 hour). The solution was evaporated and pumped under vacuum to give the acid chloride as an orange oil, which was used directly.

The acid chloride from above was dissolved in dichloromethane (20 ml) and cooled to 0° C. A solution of dipropylamine (0.89 g, 8.8 mmol) in dichloromethane (5 ml) was added dropwise, allowed to warm to room temperature, and stirred for 18 hours. Dichloromethane (25 ml) was added and the reaction mixture washed with 1N HCl (25 ml) and NaHCO$_3$ (25 ml). The organic layer was dried (Na$_2$SO$_4$) and concentrated to give the title compound (1.3 g, 70%) as an oil.

C. Preparation of tetraethyl-3-(dipropylamino)-propane-1,1-bisphosphonate

A solution of N,N-dipropyl-3,3-bis(diethoxyphosphinyl) propionamide (1.25 g, 2.9 mmol) in THF (7.1 ml) was cooled to 0° C., and borane-methylsulfide (0.71 ml, 7.1 mmol) was added via syringe. The reaction was stirred at 0° C. for 20 minutes, then warmed at 65 C. for 3 hours. The reaction mixture was cooled to 0° C. and 6N HCl (6 ml) was added carefully. The solvent was removed in vacuo, and the residue was treated with methanol (5 ml) and concentrated. The residue was dissolved in water (10 ml) and extracted with Et$_2$O (3×10 ml). The aqueous layer was made basic to phenolphthalein with solid KOH and saturated with NaCl. The product was extracted into dichloromethane (5×20 ml), dried (Na$_2$SO$_4$) and concentrated to give the title compound (0.71 g, 60%).

D. Preparation of 3-(dipropylaminopropane-1,1-bisphosphonic acid

Tetraethyl 3-(dipropylamino)propane-1,1-bisphosphonate (0.55 g, 1.3 mmol) and 12NHCl (6 ml) were heated at reflux for 20 hours. After cooling, the volatile materials were removed under vacuum to give 0.47 g of Compound No. 155 as a hygroscopic glass.

Example 8

Preparation of 3-(benzylamino)pentane-1,1-bisphosphonic acid (Compound No. 159)

A. Preparation of N-methoxy-N-methyl-3,3-bis-(diethoxyphosphinyl)propionamide.

To a solution of 3,3-bis(diethoxyphosphinyl)propanoic acid (4.00 g, 11.5 mmol) and dimethylformamide (2 drops) in dichloromethane (25 ml) was added oxalyl chloride (1.65 g, 13.0 mmol). The solution was stirred at ambient temperature until gas evolution ceased (~1 hour). The solution was evaporated and benzene (20 ml) was added. The solvent was removed under vacuum to give the acid chloride as an orange oil, which was used directly. The acid chloride from above was dissolved in dichloromethane (100 ml) and N-methyl-O-methylhydroxylamine hydrochloride (1.25 g, 13.0 mmol) was added. The reaction mixture was cooled in an ice bath and pyridine (2.05 g, 26.0 mmol) was added dropwise. After the addition, the reaction mixture was allowed to warm to room temperature for 1 hour. This mixture was washed with 1N HCl (50 ml) and saturated NaHCO$_3$ (50 ml), dried (Na$_2$SO$_4$) and concentrated to give the crude product as an oil. Flash chromatography on silica gel eluting with 20% i-propanol in EtOAc gave the title compound (3.50 g, 78%) as a light yellow oil.

B. Preparation of tetraethyl 3-oxopentane-1,1-bisphosphonate

A solution of N-methoxy-N-methyl-3,3-bis (diethoxyphosphinyl)propionamide (1.00 g, 2.6 mmol) in THF (5 ml) was slowly added to a slurry of 80% sodium hydride (80 mg, 2.7 mmol) in THF (10 ml) at 0° C. Stirring was continued until all of the hydride was consumed (~20 minutes). The solution was cooled to −78° C. and ethylmagnesium bromide (1.0 ml of a 3.0M solution in diethyl ether, 3.0 mmol) was added. After the addition, the reaction mixture was warmed to 0° C. and stirred for one hour. The reaction was quenched by pouring slowly into a well-stirred ice-cold mixture of ethanol (40 ml) and concentrated HCl (5 ml). The solvents were removed in vacuo, the residue was taken up in brine (20 ml) and extracted with dichloromethane (4×20 ml). The combined extracts were dried (Na$_2$SO$_4$), concentrated in vacuo, and the resulting oil was purified by flash chromatography on silica gel eluting with 10% i-propanol in ethyl acetate to give the title compound (0.50 g, 54%) as a pale yellow oil.

C. Preparation of 3-(benzylamino)pentane-1,1-bisphosphonic acid

To a stirred solution of tetraethyl 3-oxopentane-1,1-bisphosphonate (0.50 g, 1.4 mmol) in methanol (5 ml) was added a small amount of bromothymol blue and benzylamine (0.75 g, 7.0 mmol). Acetic acid was added dropwise until the solution turned yellow (pH=6), and NaCNBH$_3$ (57 mg, 0.9 mmol) was added. The resulting yellow solution was stirred at room temperature for 2 days, at which time more NaCNBH$_3$ (20 mg) was added. After stirring a total of 4 days, the reaction was quenched by adding concentrated HCl until the pH was less than 1, and the solvents were removed in vacuo. The residue was taken up in water (10 ml) and washed with diethyl ether (2×20 ml). The aqueous layer was made basic (pH greater than 10) by the addition of solid KOH, saturated with NaCl, and extracted with dichloromethane (5×25 ml). The combined extracts were dried (Na$_2$SO$_4$) and concentrated to give tetraethyl 3-benzylaminopentane-1,1-bisphosphonate. This material was hydrolyzed by heating at reflux in concentrated HCl (6 ml) for 20 hours. The volatiles were removed under vacuum, the residue dissolved in water (10 ml) and concentrated under vacuum to give 0.49 g of Compound No. 159 as a hygroscopic foam.

Example 9

Preparation of 3-(butylamino)propane-1,1-bisphosphonic acid (Compound No. 158)

A. Preparation of N-butyl-3,3-bis(diethoxyphosphinyl) propionamide

Tetraethyl methylenebisphosphonate (1.44 g, 5.0 mmol) in THF (1 mL) was added to a slurry of 80% sodium hydride (150 mg, 5.0 mmol) in THF (4 mL) at 0° C. The reaction was warmed to room temperature and stirred until all of the hydride was consumed. A solution of N-butyl-2-chloroacetamide (0.75 g, 5.0 mmol) in THF (1 ml) and potassium iodide (100 mg) were then added. The reaction mixture was then heated at 50° C. for 18 hours, during which time sodium chloride precipitated. Additional sodium hydride (20 mg) was added, and the reaction mixture was heated an additional 4 hours. After cooling, the mixture was poured into 1N HCl (10 mL) and diethyl ether (50 mL) was added. The diethyl ether layer was further extracted with water (3×10 mL). The combined aqueous fractions were extracted with dichloromethane (4×25 mL). The combined extracts were dried (Na$_2$SO$_4$) and concentrated to give the title compound (1.40 g, 70%) as an oil.

B. Preparation of 3-(butylamino)propane-1,1-bisphosphonic acid

A solution of N-butyl-3,3-bis(diethoxyphosphinyl) propionamide (1.40 g, 3.5 mmol) in THF (9 mL) was cooled to 0° C., and borane-methyl sulfide (0.90 ml, 9.0 mmol) was added via syringe. The reaction was stirred at 0° C. for 5 minutes, then warmed to 65° C. for 3 hours. The reaction mixture was cooled to 0° C. and 6N HCl (6 ml) was added carefully. The solvent was removed in vacuo, and the residue was repeatedly concentrated from methanol (3×10 mL). The product was dissolved in 12N HCl and heated at reflux for 20 hours. After cooling, the volatile materials were removed under vacuum, the residue was dissolved in water (10 mL) and then concentrated to give 1.05 g of Compound No. 158 as a hygroscopic glass.

Example 10

Preparation of 2-(2-pyrrolidino)ethane-1,1-bisphosphonic acid, triammonium salt (Compound No. 245)

A. Preparation of tetraethyl 2[2-(1-pyrrolino)]ethane-1,1-bisphosphonate

A solution of N-methoxy-N-methyl-3,3-bis (diethoxyphosphinyl)propionamide (1.82 g, 4.7 mmol) in THF (5 ml) was slowly added to a slurry of 80% sodium hydride (160 mg, 5.3 mmol) in THF (15 ml) at 0° C. Stirring was continued until all of the hydride was consumed (~20 minutes). The solution was cooled to 0° C. and 3-[1-(2,2,5,5-tetramethyl-1-aza-2,5-disilacyclopentyl)] propylmagnesium bromide (15 ml of a 1.0M solution in diethyl ether, 15 mmol) was added. After the addition, the reaction mixture was allowed to warm to room temperature and stirred for 15 hours. At that time, the mixture was cooled to 0° C. and quenched by the slow addition of 10% HCl, and stirred at room temperature for 2 hours. Ether (30 mL) was added and the product was extracted with 1N HCl (3×10 mL). The combined aqueous extracts were washed with ether (10 mL) and then solid KOH was added to bring the pH to 10. The solvent was evaporated and the residue extracted with dichloromethane (4×50 mL). Evaporation of the solvent gave the crude product which was purified by flash chromatography on silica gel eluting with 5% methanol in chloroform to give the title compound (0.40 g).

B. Preparation of tetraethyl 2-(2-pyrrolidino)ethane-1,1-bisphosphonate

Tetraethyl 2-[2-(1-pyrrolino)]ethane-1,1-bisphosphonate (0.40 g, 1.15 mmol) was dissolved in ethanol (4 mL) and NaCNBH$_3$ (80 mg, 1.25 mmol) was added. 6N HCl was added to keep the solution acidic to bromocresol green (pH~4). After 30 minutes, 6N HCl was added (2 mL) and the solvent was removed in vacuo. Methanol (10 ml) was added and evaporated. The residue was added to dichloromethane (20 mL) and extracted into 1N HCl (2×10 mL). The solution was made basic (pH~10) with solid KOH and the product was extracted into dichloromethane (3×20 ml). The combined organic extracts were dried (K$_2$CO$_3$) and concentrated to give 0.26 g of tetraethyl 2-(2-pyrrolidino)ethane-1,1-bisphosphonate.

C. Preparation of 2-(2-pyrrolidino)ethane-1,1-bisphosphonic acid, triammonium salt To a stirred solution of tetraethyl 2-(2-pyrrolidino)ethane-1,1-bisphosphonate (0.26 g, 0.75 mmol) in dry dichloromethane (0.5 mL) at 0° C. was added bromotrimethylsilane (1.00 mL, 8.0 mmol), and the solution was allowed to warm to room temperature. After stirring for 16 hours, the solvent was removed in vacuo, the residue was dissolved in benzene (7 mL) and concentrated in vacuo. To the residue was added NH$_4$OH (4 mL of a 3.5M solution) which was stirred for 30 minutes at room temperature. The solvent was removed in vacuo, and the residue concentrated repeatedly from methanol (2×5 mL) to give 0.24 g of 2-(2-pyrrolidino) ethane-1,1-bisphosphonic acid as a white powder.

Example 11

Preparation of 5-aminopentane-1,1-bisphosphonic acid, triammonium salt (Compound No. 249)

A. Preparation of tetraethyl 5-aminopentane-1,1-bisphosphonate

Tetraethyl vinylidine bisphosphonate (1.20 g, 4.0 mmol) was dissolved in dry THF (10 mL) and cooled to 0° C. A solution of 3-[1-(2,2,5,5-tetramethyl-1-aza-2,5-disilacyclopentyl)]propylmagnesium bromide in ether (4.5 mL of 1.0M solution, 4.5 mmol) was added slowly and the reaction mixture was then allowed to warm to room temperature for 15 hours. The reaction was quenched with 1N HCl (25 mL) and stirred for 2 hours. This was washed with ether (10 mL). The ether layer was extracted with 1N HCl and the combined aqueous extracts were made basic (pH=10) with solid KOH. Volatiles were removed in vacuo, and the residue was extracted with dichloromethane (3×50 mL). The solution was concentrated to 20 mL and extracted with 1N HCl (2×10 mL). Solid KOH was added to pH=10, and the product was extracted into dichloromethane (3×15 mL). The solution was dried (K$_2$CO$_3$) and concentrated to give the title compound (0.54 g) as an oil.

B. Preparation of 5-aminopentane-1,1-bisphosphonic acid, triammonium salt

To a stirred solution of tetraethyl 5-aminopentane-1,1-bisphosphonate (0.51 g, 1.5 mmol) in dry dichloromethane (0.5 mL) at 0° C. was added bromotrimethylsilane (1.3 mL, 10 mmol), and the solution was allowed to warm to room temperature. After stirring for 16 hours, the solvent was removed in vacuo, the residue was dissolved in benzene (5 mL) and concentrated in vacuo. To the residue was added NH$_4$OH (7 mL of a 3.0M solution) which was stirred for 30 minutes at room temperature. The solvent was removed in vacuo, and the residue concentrated repeatedly from methanol (2×5 mL) to give 0.52 g of 5-amino-1,1-pentylbisphosphonic acid, triammonium salt as a white powder.

Example 12

Preparation of N-benzyl-5-aminopentane-1,1-bisphosphonic acid, triammonium salt (Compound No. 250)

A. Preparation of tetraethyl N-benzoyl-5-aminopentane-1,1-bisphosphonate

A solution of benzoyl chloride (0.73 g, 5.0 mmol) in dichloromethane was added slowly to a solution of tetraethyl 5-aminopentane-1,1-bisphosphonate (1.50 g, 4.5 mmol) from Example 11, part A, and triethylamine (0.76 mL, 5.5 mmol) in dichloromethane at 0° C. After warming to room temperature for 30 minutes, the reaction was quenched by addition of 1N HCl (30 mL). The product was extracted into dichloromethane (2×20 mL) and the combined organic layers were washed with saturated NaHCO$_3$ (2×15 mL), dried (Na$_2$SO$_4$), and concentrated in vacuo. Flash chromatography on silica gel eluting with 15% i-propanol in ethylacetate in EtOAc gave the title compound (0.64 g) as an oil.

B. Preparation of tetraethyl N-benzyl-5-aminopentane-1,1-bisphosphonate

A solution of tetraethyl N-benzoyl-5-aminopentane-1,1-bisphosphonate (0.63 g, 1.36 mmol) in THF (3.4 mL) was cooled to 0° C., and borane methylsulfide (0.34 ml, 3.4 mmol) was added via syringe. The reaction was stirred at 0° C. for 20 minutes, then warmed to 65° C. for 2.5 hours. The reaction mixture was cooled to 0° C. and 6N HCl (4.0 ml) was added carefully. The solvent was removed in vacuo, and the residue was concentrated repeatedly from methanol (2×5 mL). The residue was dissolved in water (10 ml) and extracted with diethyl ether (3×5 ml). The aqueous layer was made basic to phenolphthalein with solid KOH and saturated with NaCl. The product was extracted into dichloromethane (5×20 ml), dried ($Na_2SO_4$) and concentrated to give the title compound (0.28 g).

C. Preparation of N-benzyl-5-aminopentane-1,1-bisphosphonic acid, triammonium salt Bromotrimethylsilane (0.54 mL, 4.1 mmol) was added to a stirred solution of the compound of part B (0.26 g, 0.58 mmol) in dry dichloromethane (0.5 mL) at 0° C., and the solution was allowed to warm to room temperature. After stirring for 18 hours, the solvent was removed in vacuo. To the residue was added $NH_4OH$ (7 mL of a 3.0M solution) which was stirred for 30 minutes at room temperature. The solvent was removed in vacuo, and the residue concentrated repeatedly from methanol (2×5 mL) to give 0.32 g N-benzyl-5-aminopentane-1,1-bisphosphonic acid, triammonium salt as a white powder.

Example 13

Preparation of 3-aminooctane-1,1-bisphosphonic acid (Compound No. 258)

A. Preparation of tetraethyl 3-nitrooctane-1,1-bisphosphonate

A solution of tetraethyl vinvylidinebisphosphonate (2.0 g, 6.67 mmol) in THF (3 ml) was added dropwise to a stirred solution of 1-nitrohexane (0.87 g, 6.67 mmol) and diisopropylamine (0.76 g, 7.50 mmol) in THF (4 mL) at room temperature. The reaction mixture was stirred at ambient temperature for 18 hours, and then heated at 50° C. for 3 hours. After cooling, the solvent was removed in vacuo. The residue was dissolved in dichloromethane (30 mL) and washed with 1N HCl (10 mL) and water (10 mL). The combined aqueous layers were extracted with dichloromethane (10 mL). The organic layers were pooled, dried ($Na_2SO_4$) and concentrated. Flash chromatography on silica gel eluting with 5% methanol in chloroform gave the title compound (2.3 g, 80%) as an oil.

B. Preparation of tetraethyl 3-aminooctane-1,1-bisphosphonate

To a stirred solution of tetraethyl 3-nitrooctane-1,1-bisphosphonate (0.70 g, 1.62 mmol) in methanol (4 mL) was added ammonium formate (0.45 g, 6.9 mmol) and 10% palladium on carbon (0.070 g). After 24 hours, more 10% palladium on carbon (0.035 g) and ammonium formate (0.45 g, 6.9 mmol) were added. After stirring for a total of 4 days, the reaction mixture was filtered, rinsing the residue with methanol, and concentrated. The residue was taken up in brine (5 mL) and extracted with dichloromethane (4×15 mL), dried ($Na_2SO_4$) and concentrated to give the title compound (0.60 g, 95%) as an oil.

C. Preparation of 3-aminooctyl-1,1-bisphosphonic acid, triammonium salt

To a solution of tetraethyl 3-aminooctane-1,1-bisphosphonate (0.45 g, 1.12 mmol) in dry dichloromethane (1.1 mL) was added bromotrimethylsilane (1.05 mL, 7.85 mmol) via syringe. After 18 hours, the mixture was concentrated under vacuum. To the residue was added 3N $NH_4OH$ (8 mL) which was stirred for 30 minutes at room temperature. The solvent was removed in vacuo and the residue concentrated from methanol (2 mL) to give 0.40 g of 3-aminooctane-1,1-bisphosphonic acid, triammonium salt as a white powder.

Employing a process similar to those described above, the following compounds, listed in Tables I–V, were prepared:

TABLE I $$\begin{array}{c} R^6 \quad\quad R^4 \;\; PO_3H_2 \\ \phantom{xx}\backslash \quad\quad | \quad\quad | \\ \phantom{xxx} N-C-C-R^1 \\ \phantom{xx}/ \quad\quad | \quad\quad | \\ R^7 \quad\quad R^5 \;\; PO_3H_2 \end{array}$$

| Comp. No. | $R^1$ | $R^4$ | $R^5$ | $R^6$ | $R^7$ |
|---|---|---|---|---|---|
| 1 | H | H | H | H | Phenyl[Ph] |
| 2 | H | H | H | H | 2-pyridyl |
| 8* | —OH | —$CH_3$ | —$CH_3$ | H | H |
| 12 | H | H | H | H | -n$C_3H_7$ |
| 14 | H | H | H | H | cyclohexyl |
| 15 | H | H | H | H | -i$C_3H_7$ |
| 16 | H | H | H | H | -t$C_4H_9$ |
| 18 | H | H | H | —$CH_3$ | —$CH_3$ |
| 22 | H | H | H | H | -i$C_4H_9$ |
| 23 | H | H | H | —$C_2H_5$ | —$C_2H_5$ |
| 24** | H | H | H | H | -n$C_3H_7$ |
| 25*** | H | H | H | H | -n$C_3H_7$ |
| 27 | H | H | H | H | -n$C_4H_9$ |
| 28 | H | H | H | H | —$OCH_3$ |
| 29 | H | H | H | H | —$CH_2CH_2CH=CH_2$ |
| 30 | H | H | H | H | -n$C_6H_{13}$ |
| 31 | H | H | H | H | benzyl |
| 32 | H | H | H | H | —$CH_2CH=CH_2$ |
| 33 | H | H | H | -n$C_3H_7$ | -n$C_3H_7$ |
| 34 | H | H | H | —$CH_3$ | —$OCH_3$ |
| 35 | H | H | H | —$CH_3$ | —OH |
| 36 | H | H | H | H | —$C_2H_5$ |
| 38 | H | H | H | H | —$CH_2CH_2$—O—$C_2H_5$ |
| 39 | —OH | H | H | H | —$CH_3$ |
| 40 | H | H | H | -n$C_4H_9$ | -n$C_4H_9$ |

TABLE I-continued $$\begin{array}{c} R^6 \quad R^4 \quad PO_3H_2 \\ \phantom{R^6}\backslash \phantom{R^4} | \phantom{PO_3H_2} | \\ N-C-C-R^1 \\ \phantom{R^7}/ \phantom{R^5} | \phantom{PO_3H_2} | \\ R^7 \quad R^5 \quad PO_3H_2 \end{array}$$

| Comp. No. | $R^1$ | $R^4$ | $R^5$ | $R^6$ | $R^7$ |
|---|---|---|---|---|---|
| 41*** | H | H | H | H | $-nC_6H_{13}$ |
| 42 | H | H | H | H | (S)-1-phenylethyl (CH₃, phenyl) |
| 43 | H | H | H | H | (R)-1-phenylethyl (CH₃, phenyl) |
| 44 | H | H | H | H | isopropylphenyl group (CH₃, phenyl) |
| 45 | H | H | H | H | 2-methylbenzyl |
| 46 | H | H | H | H | 3-methylbenzyl |
| 47 | H | H | H | H | $-CH_2CH_2-Ph$ |
| 50 | H | H | H | H | 3-methylpyrid-2-yl |
| 51 | H | H | H | $-CH_3$ | $-nC_3H_7$ |
| 52 | H | H | H | $-CH_3$ | $-iC_3H_7$ |
| 54 | H | H | H | H | $-H_2C-C(CH_3)=CH_2$ |
| 56 | H | H | H | H | 2,6-dichloro-4-trifluoromethylanilino |
| 57 | H | H | H | $-CH_2CH=CH_2$ | $-CH_2CH=CH_2$ |
| 58 | H | H | H | H | $-CH_2CH_2-CH(CH_3)_2$ |
| 60 | H | H | H | H | $-nC_3H_7$ |
| 61 | H | H | H | H | $-CH_2CF_3$ |
| 62 | H | H | H | $-C_2H_5$ | $-CH_2CH=CH_2$ |
| 63 | H | H | H | $-CH_3$ | $-CH_2CH=CH_2$ |
| 64 | H | H | H | H | cyclopropyl |
| 66 | H | H | H | H | 4-methylbenzyl |
| 67 | H | H | H | H | 4-chlorobenzyl |
| 68 | H | H | H | H | 3-chlorobenzyl |
| 69 | H | H | H | H | 2-chlorobenzyl |
| 70 | H | H | H | H | $-CH(CH_3)-$(4-fluorophenyl) |
| 72 | H | H | H | H | indan-2-yl |
| 74 | H | H | H | H | $-CH(CH_3)-CH_2CH_3$ |
| 75 | H | H | H | H | indan-1-yl |

TABLE I-continued $$\begin{array}{c} R^6 \quad R^4 \quad PO_3H_2 \\ | \quad | \quad | \\ N—C—C—R^1 \\ | \quad | \quad | \\ R^7 \quad R^5 \quad PO_3H_2 \end{array}$$

| Comp. No. | $R^1$ | $R^4$ | $R^5$ | $R^6$ | $R^7$ |
|---|---|---|---|---|---|
| 76 | H | H | H | H | 2,3-dimethylbenzyl |
| 77 | H | H | H | H | 2,5-dimethylbenzyl |
| 78 | H | H | H | H | 2,4-dimethylbenzyl |
| 79 | H | H | H | H | 3,4-dimethylbenzyl |
| 80 | H | H | H | H | 2-methylcyclopentyl |
| 81 | H | H | H | H | —CH$_2$—CH=CH—CH$_3$ |
| 82 | H | H | H | H | —CH(C$_2$H$_5$)$_2$ |
| 83 | H | H | H | H | —CH$_2$—CH$_2$—CH$_2$—Cl |
| 85 | H | H | H | -nC$_3$H$_7$ | —CH$_2$CH(CH$_3$)$_2$ |
| 86 | H | H | H | -nC$_3$H$_7$ | -nC$_4$H$_9$ |
| 88 | H | H | H | -nC$_3$H$_7$ | —CH$_2$CH$_2$COOH |
| 89 | H | H | H | H | —CH$_2$CH$_2$CH-Ph |
| 90 | H | H | H | H | 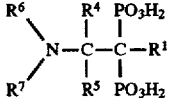 |
| 93 | H | H | H | -nC$_3$H$_7$ | —CH$_2$COOH |
| 95 | H | H | H | -nC$_3$H$_7$ | -nC$_6$H$_{13}$ |
| 98 | H | H | H | H | 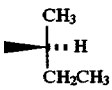 |
| 99 | H | H | H | -nC$_3$H$_7$ | —CH$_2$CH$_2$CH(CH$_3$)$_2$ |
| 102 | H | H | H | -nC$_3$H$_7$ | -nC$_5$H$_{11}$ |
| 103 | H | H | H | H | 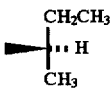 |
| 104 | H | H | H | H | 4-fluorobenzyl |
| 105 | H | H | H | H | 3,4-difluorobenzyl |
| 106 | H | H | H | H | 2,6-difluorobenzyl |
| 107 | H | H | H | H | 2-fluoro-6-chlorobenzyl |
| 108 | H | H | H | H | 2,6-dichlorobenzyl |
| 111 | H | H | H | H | -nC$_{10}$H$_{21}$ |
| 118 | H | H | H | H | —CH(CH$_3$)—CH$_2$CH$_3$ |
| 120 | H | H | H | H | 2-pyridylmethyl |
| 121 | H | H | H | H | 3-pyridylmethyl |
| 122 | H | H | H | H | 4-pyridylmethyl |
| 123 | H | H | H | H | 2-methoxybenzyl |
| 124 | H | H | H | —CH$_3$ | —C$_2$H$_5$ |
| 125 | H | H | H | H | 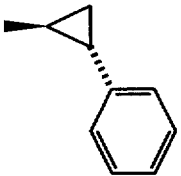 |
| 131* | H | H | H | H | —CH$_2$—CH(OH)—CH$_3$ |
| 132**** | H | H | H | H | —CH$_2$—CH(OH)—CH$_3$ |
| 133*** | H | H | H | H | —CH$_2$—CH(OH)—CH$_3$ |
| 134* | H | H | H | H | 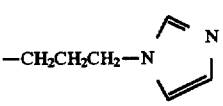 |

TABLE I-continued $$\begin{array}{c} R^6 \\ \phantom{X} \diagdown \\ N-\underset{\underset{R^5}{|}}{\overset{\overset{R^4}{|}}{C}}-\underset{\underset{PO_3H_2}{|}}{\overset{\overset{PO_3H_2}{|}}{C}}-R^1 \\ R^7 \end{array}$$

| Comp. No. | $R^1$ | $R^4$ | $R^5$ | $R^6$ | $R^7$ |
|---|---|---|---|---|---|
| 135 | H | H | H | H | (S)-1-phenylethyl (CH$_3$ wedge) |
| 136* | H | H | H | H | 1-phenylethyl |
| 137*** | H | H | H | H | 1-phenylethyl |
| 138**** | H | H | H | H | 1-phenylethyl |
| 267 | H | H | H | H | —CH$_2$CH$_2$CH$_2$CH$_2$-Ph |
| 269 | H | H | H | H | —CH(Ph)—CH(CH$_3$)$_2$ |
| 270 | H | H | H | —CH$_3$ | benzyl |
| 271 | H | H | H | —C$_2$H$_5$ | benzyl |
| 272 | H | H | H | iC$_3$H$_7$ | benzyl |
| 273 | H | H | H | -nC$_4$H$_9$ | benzyl |
| 274 | H | H | H | -nC$_3$H$_7$ | benzyl |
| 276 | H | H | H | -iC$_4$H$_9$ | -sC$_4$H$_9$ |
| 277 | H | H | H | H | —CH$_2$CH$_2$CH$_2$CH$_2$—S-Ph |
| 279 | H | H | H | H | —CH$_2$CH(CH$_3$)-Ph |
| 280 | H | H | H | H | 4-methoxybenzyl |
| 281 | H | H | H | H | —CH$_2$-(1-naphthyl) |
| 282 | H | H | H | H | —CH$_2$CH$_2$CH$_2$—N(piperidinyl) |
| 284 | H | H | H | H | —CH(CH$_3$)CH$_2$CH$_2$-Ph |
| 286 | H | H | H | H | —CH$_2$-(2-furyl) |
| 287 | H | H | H | H | —CH$_2$-cyclohexyl |

TABLE I-continued $$\begin{array}{c} R^6 \\ \diagdown \\ N-C-C-R^1 \\ \diagup \\ R^7 \end{array} \begin{array}{c} R^4 \quad PO_3H_2 \\ | \quad | \\ | \quad | \\ R^5 \quad PO_3H_2 \end{array}$$

| Comp. No. | $R^1$ | $R^4$ | $R^5$ | $R^6$ | $R^7$ |
|---|---|---|---|---|---|
| 289 | H | H | H | -nC$_3$H$_7$ | —CH$_2$CH$_2$-Ph |
| 290 | H | H | H | -nC$_3$H$_7$ | 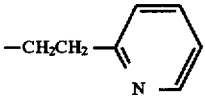 |
| 292 | H | H | H | H |  |
| 294 | H | H | H | H | —CH$_2$CH$_2$CH$_2$OH |
| 295 | H | H | H | H | —CH$_2$CH$_2$CH$_2$CH$_2$OH |
| 296 | H | H | H | H | 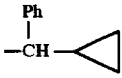 |
| 297 | H | H | H | H | 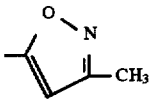 |
| 298 | H | H | H | H | 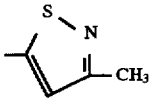 |
| 299 | H | H | H | H | —N(CH$_3$)-Ph |
| 303 | H | H | H | H | —CH(CH$_3$)CH$_2$CH$_2$CH$_2$-Ph |
| 304 | H | H | H | -nC$_3$H$_7$ | —CH$_2$CH$_2$CH$_2$CH$_2$CH$_2$-Ph |
| 308 | H | H | H | -nC$_3$H$_7$ | -iC$_4$H$_9$ |
| 309 | H | H | H | H | —CH$_3$ |
| 311 | H | H | H | H | —CH$_2$CH$_2$OH |
| 312 | H | H | H | H | 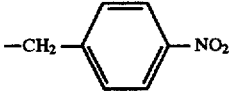 |
| 313 | H | H | H | —CH$_3$ | -iC$_4$H$_9$ |
| 314 | H | H | H | H | —CH$_2$—CH=CH-Ph |
| 315 | H | H | H | H | —N(CH$_3$)$_2$ |
| 317 | H | H | H | H | —CH$_2$CH$_2$—S—CH$_2$CH$_3$ |
| 318 | H | H | H | H |  |
| 319 | H | H | H | H | —CH$_2$CH$_2$—O—CH$_3$ |
| 320 | H | H | H | H | —CH$_2$CH$_2$CH$_2$—O—CH$_3$ |
| 323 | H | H | H | H | —CH$_2$CH$_2$—S—CH$_3$ |
| 324 | H | H | H | H | —CH$_2$CH$_2$CH(CH$_3$)-Ph |
| 326 | H | H | H | H | —CH$_2$CH$_2$CH$_2$—S—CH$_3$ |
| 327 | H | H | H | H | -nC$_5$H$_{11}$ |
| 329 | H | H | H | H | —CH$_2$CH(CH$_3$)CH$_2$-Ph |
| 330 | H | H | H | H | 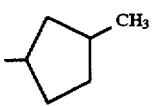 |

TABLE I-continued $$\begin{array}{c} R^6 \\ \phantom{R^6}\diagdown \\ N-C-C-R^1 \\ \phantom{R^7}\diagup \phantom{R^5} \phantom{PO_3H_2} \\ R^7 \phantom{N-}R^5 \phantom{PO_3H_2} \end{array} \quad \begin{array}{c} R^4 \phantom{C} PO_3H_2 \\ \end{array}$$

| Comp. No. | R¹ | R⁴ | R⁵ | R⁶ | R⁷ |
|---|---|---|---|---|---|
| 331 | H | H | H | H | -CH(CH₃)-(cyclohexenyl) |
| 332 | H | H | H | H | -CH₂-(4-chlorocyclohexyl) |
| 333 | H | H | H | H | -CH(CH₃)-(4-chlorocyclohexyl) |
| 334 | H | H | H | H | —CH₂CH₂CH₂CH(CH₃)-Ph |
| 335 | H | H | H | cyclopropyl | -nC₃H₇ |
| 336 | H | H | H | H | —CH₂CH₂CH₂CH₂CH₂CH₂-Ph |
| 337 | H | H | H | —CH₃ | —CH₂CH₂CH₂-Ph |
| 338 | H | H | H | H | —CH₂CH₂CH₂CH₂CH₂CH₂-Ph |
| 341 | H | H | H | H | —CH₂CH₂CH₂CH₂CH₂—O-Ph |
| 343 | H | H | H | H | —CH₂CH₂N(CH₃)₂ |
| 344 | H | H | H | —C₂H₅ | —CH₂CH₂CH₂CH₂-Ph |
| 345 | H | H | H | H | —CH₂CH₂CH₂N(CH₃)₂ |
| 346 | H | H | H | H | —CH₂CH₂CH₂CH₂CH₂-Ph |
| 347 | H | H | H | —C₂H₅ | —CH₂CH₂CH₂-Ph |
| 348 | H | H | H | H | —CH₂CH₂CH₂CH₂N(CH₃)₂ |
| 349 | H | H | H | —CH₃ | —CH₂CH₂CH₂NHCH₃ |
| 350 | H | H | H | H | -CH₂-(tetrahydrofuran-2-yl) |
| 351 | H | H | H | H | —CH₂CH₂CH₂CH(CH₃)—Cl |
| 352 | H | H | H | H | —(CH₂)₁₁-Ph |
| 353 | H | H | H | H | -CH₂CH₂CH₂-(2-oxopyrrolidin-1-yl) |
| 356 | H | H | H | H | —CH(CH₃)CH₂CH₂CH₂N(C₂H₅)₂ |
| 357 | H | H | H | H | —(CH₂)₉-Ph |
| 358 | H | H | H | H | —CH₂CH₂CH₂CH₂CH₂OH |
| 361 | H | H | H | H | —CH₂CH₂CH₂—Si(OH)₃ |
| 362 | H | H | H | H | 4-hydroxymethylbenzyl |
| 363 | H | H | H | H | —CH₂-cyclopropyl |
| 364 | H | H | H | H | —CH=CH-Ph |
| 365 | H | H | H | H | -(1-ethylpiperidin-4-yl)methyl |
| 367 | H | H | H | H | —CH₂CH₂CH₂COOH |
| 368 | H | H | H | H | —CH₂CH₂COOH |
| 370 | H | H | H | H | —CH₂CH₂CH₂S(O)₂-Ph |
| 371 | H | H | H | H | —CH₂CH₂S(O)₂—CH₃ |
| 372 | H | H | H | H | —CH₂CH₂CH₂CH₂—O-Ph |

TABLE I-continued $$\begin{array}{c} R^6 \\ \diagdown \\ R^7 \end{array} N - \underset{\underset{R^5}{|}}{\overset{\overset{R^4}{|}}{C}} - \underset{\underset{PO_3H_2}{|}}{\overset{\overset{PO_3H_2}{|}}{C}} - R^1$$

| Comp. No. | R¹ | R⁴ | R⁵ | R⁶ | R⁷ |
|---|---|---|---|---|---|
| 373 | H | H | H | H | —CH₂—CH(CH₃)—C₆H₄—Cl (4-Cl) |
| 374 | H | H | H | H | —CH₂—(4-biphenyl) |
| 375 | H | H | H | —CH₃ | —CH₂—C≡CH |
| 376 | H | H | H | H | —CH₂CH₂NH₂ |
| 377 | H | H | H | H | —CH₂CH₂CH₂—O-Ph |
| 378 | H | H | H | H | —CH₂CH₂CH₂—NH—CH₂-Ph |
| 382 | H | H | H | H | —CH(CH₂CH₂CH₃)(Ph) |
| 383 | H | H | H | H | —CH(CH₂CH₂CH₃)(Ph) |
| 384 | H | H | H | H | —CH₂CH₂—S-Ph |
| 385 | H | H | H | H | —CH₂CH₂CH₂—C₆H₄—NO₂ (4-NO₂) |
| 387 | H | H | H | H | —CH(CH₂OH)(Ph) |
| 388 | H | H | H | H | —CH(CH₂OH)(Ph) |
| 389 | H | H | H | H | —CH₂CH₂CH₂C(CH₃)₂—OH |
| 390 | H | H | H | H | pyrazolyl-(2,6-dichloro-4-trifluoromethylphenyl) |
| 391 | H | H | H | -nC₃H₇ | —CH₂CH₂CH₂-Ph |
| 392 | H | H | H | H | —CH₂CH₂—O-Ph |
| 393 | H | H | H | H | —CH₂CH₂CH₂—O—C₆H₄—Cl (4-Cl) |
| 394 | H | H | H | H | —CH₂CH₂—O—C₆H₄—Cl (4-Cl) |

TABLE I-continued $$\begin{array}{c} R^6 \\ \diagdown \\ R^7 \end{array} N - \underset{\underset{R^5}{\overset{R^4}{|}}}{C} - \underset{\underset{PO_3H_2}{\overset{PO_3H_2}{|}}}{C} - R^1$$

| Comp. No. | $R^1$ | $R^4$ | $R^5$ | $R^6$ | $R^7$ |
|---|---|---|---|---|---|
| 395 | H | H | H | H | $-CH_2CH_2-NH-C(O)-CH_3$ |
| 396 | H | H | H | H | $-CH_2CH_2CH_2-O-\text{C}_6\text{H}_4-OCH_3$ (para) |
| 398 | H | H | H | H | $-CH_2CH_2-O-\text{C}_6\text{H}_4-OCH_3$ (para) |
| 399 | H | H | H | H | $-CH_2CH_2-C\equiv N$ |
| 400 | H | H | H | $-CH_3$ | $-CH_2CH_2CH_2CH_2-Ph$ |
| 401 | H | H | H | H | $-CH_2CH_2-O-\text{C}_6\text{H}_4-I$ (ortho) |
| 403 | H | H | H | H | $-CH_2CH_2-O-\text{C}_6\text{H}_4-Cl$ (ortho) |
| 404 | H | H | H | H | $-CH_2CH_2-S-CH_2-Ph$ |
| 405 | H | H | H | H | $-CH_2CH_2CH_2CH_2-O-\text{C}_6\text{H}_4-SCH_3$ (para) |
| 406 | H | H | H | H | $-CH_2CH_2CH_2CH_2CH_2-O-\text{C}_6\text{H}_4-NO_2$ (para) |
| 408 | H | H | H | H | $-CH_2CH_2CH_2CH_2-O-\text{C}_6\text{H}_4-OCH_3$ (para) |
| 409 | H | H | H | H | $-CH_2CH_2CH_2CH_2-O-\text{C}_6\text{H}_4-COOH$ (para) |
| 410 | H | H | H | H | $-CH_2CH_2CH_2CH_2CH_2-O-\text{C}_6\text{H}_4-Cl$ (para) |
| 412 | H | H | H | H | $-CH_2CH_2CH_2CH_2-O-\text{C}_6\text{H}_4-NO_2$ (para) |

TABLE I-continued $$\begin{array}{c} R^6 \\ \phantom{R^6}\diagdown \\ \phantom{RRR}N-\underset{\underset{R^5}{|}}{\overset{\overset{R^4}{|}}{C}}-\underset{\underset{PO_3H_2}{|}}{\overset{\overset{PO_3H_2}{|}}{C}}-R^1 \\ \phantom{R^7}\diagup \\ R^7 \end{array}$$

| Comp. No. | $R^1$ | $R^4$ | $R^5$ | $R^6$ | $R^7$ |
|---|---|---|---|---|---|
| 413 | H | H | H | H | —CH$_2$CH$_2$—O—(3-chlorophenyl) |
| 414 | H | H | H | H | —CH$_2$CH$_2$CH$_2$CH$_2$—S—(4-nitrophenyl) |
| 415 | H | H | H | H | 3-chloro-5-(trifluoromethyl)pyridin-2-ylmethyl |
| 416 | H | H | H | H | —CH(Ph)—CH$_2$CH$_2$CH$_2$CH$_3$ |
| 417 | H | H | H | H | —CH(Ph)—CH$_2$CH$_2$CH$_3$ |
| 418 | H | H | H | H | —CH$_2$CH$_2$—O—(4-chlorophenyl) |
| 420 | H | H | H | H | —CH$_2$CH$_2$CH$_2$CH$_2$CH$_2$Cl |
| 421 | H | H | H | -nC$_3$H$_7$ | —CH$_2$CH$_2$CH(PO$_3$H$_2$)$_2$ |
| 422 | H | H | H | H | —CH(CH$_3$)-(1-naphthyl) |
| 423 | H | H | H | H | —C(CH$_3$)$_2$-Ph |
| 424 | H | H | H | H | 5-(trifluoromethyl)pyridin-2-ylmethyl |
| 425 | H | H | H | H | —CH$_2$CH$_2$CH$_2$CH$_2$CH$_2$CH$_2$—O-Ph |
| 426 | H | H | H | H | —CH$_2$CH$_2$CH$_2$—O—(2,4-dichlorophenyl) |
| 427 | H | H | H | H | —CH$_2$CH$_2$CH$_2$—O—(4-cyanophenyl) |

TABLE I-continued $$\begin{array}{c} R^6 \quad R^4 \quad PO_3H_2 \\ \diagdown N-C-C-R^1 \\ \diagup \quad | \quad | \\ R^7 \quad R^5 \quad PO_3H_2 \end{array}$$

| Comp. No. | R¹ | R⁴ | R⁵ | R⁶ | R⁷ |
|---|---|---|---|---|---|
| 428 | H | H | H | H | —(CH₂)₅—O—(2,4-dichlorophenyl) |
| 430 | H | H | H | H | 5-(1,3,4-thiadiazol-2-yl) |
| 432 | H | H | H | H | —CH₂CH₂—CH(Ph)₂ |
| 433 | H | H | H | H | —CH(CH₃)—(4-bromophenyl) |
| 434 | H | H | H | H | —CH(CH₃)—(4-chlorophenyl) |
| 435 | H | H | H | H | —CH₂CH₂—(4-methoxyphenyl) |
| 436 | H | H | H | H | —CH(CH₃)—(4-nitrophenyl) |
| 437 | H | H | H | H | —CH₂—(3-phenoxyphenyl) |
| 438 | H | H | H | -nC₃H₇ | —CH₂CH₂—O-Ph |
| 439 | H | H | H | H | —(CH₂)₅—O—(3-methylphenyl) |
| 440 | H | H | H | —CH₂-Ph | —CH(CH₃)CH₂CH₂-Ph |

TABLE I-continued $$\begin{array}{c} R^6 \\ \phantom{R^6}\diagdown \\ \phantom{R^6}N \\ \phantom{R^6}\diagup \\ R^7 \end{array} \begin{array}{c} R^4 \\ | \\ -C- \\ | \\ R^5 \end{array} \begin{array}{c} PO_3H_2 \\ | \\ -C-R^1 \\ | \\ PO_3H_2 \end{array}$$

| Comp. No. | R¹ | R⁴ | R⁵ | R⁶ | R⁷ |
|---|---|---|---|---|---|
| 441 | H | H | H | H | —CH₂CH₂—O—(2-pyridyl-5-CF₃) |
| 442 | H | H | H | —CH₂CH₂CH₂-Ph | —CH₂CH₂CH₂-Ph |
| 443 | H | H | H | H | —(CH₂)₄—O—(4-biphenyl) |
| 444 | H | H | H | —CH₂-Ph | —CH₂CH₂CH₂-Ph |
| 445 | H | H | H | -nC₄H₉ | —CH₂CH₂CH₂-Ph |
| 446 | H | H | H | H | —(CH₂)₅—O—(3-phenoxyphenyl) |
| 447 | H | H | H | H | —CH(CH₃)-cyclopentyl |
| 448 | H | H | H | H | —CH(CH₃)-cycloheptyl |
| 449 | H | H | H | H | —CH₂CH(CH₃)—O-Ph |
| 450 | H | H | H | H | —CH₂CH(OH)CH₂OH |
| 451 | H | H | H | H | tetrazolyl |
| 452 | H | H | H | H | (4-methylthiazol-2-yl) |
| 453 | H | H | H | H | (5-methylthiazol-2-yl) |
| 454 | H | H | H | H | (pyrimidin-2-yl) |
| 455 | H | H | H | -iC₃H₇ | —CH₂CH₂CH₂-Ph |
| 456 | H | H | H | H | (5-methylisoxazol-3-yl) |

TABLE I-continued $$\begin{array}{c} R^6 \quad R^4 \quad PO_3H_2 \\ \phantom{R^6}\diagdown \phantom{|} | \phantom{|} | \\ N-C-C-R^1 \\ \phantom{R^7}\diagup \phantom{|} | \phantom{|} | \\ R^7 \quad R^5 \quad PO_3H_2 \end{array}$$

| Comp. No. | R¹ | R⁴ | R⁵ | R⁶ | R⁷ |
|---|---|---|---|---|---|
| 457 | H | H | H | H | —CH₂CH₂CH₂—(4-Cl-C₆H₄) |
| 458 | H | H | H | H | H |
| 459 | H | H | H | H | —(CH₂)₈—OH |
| 460 | H | H | H | -nC₃H₇ | —CH₂CH₂CH₂—(4-Cl-C₆H₄) |
| 461 | H | H | H | H | —CH₂CH₂CH₂CH₂CH₂NHCH₂-Ph |
| 462 | H | H | H | H | —(2-pyridyl) |
| 463 | H | H | H | H | —CH₂CH₂—N(imidazolidin-2-one) |
| 465 | H | H | H | H | —(1-hydroxy-2-indanyl) |
| 466 | H | H | H | H | —CH(Ph)₂ |
| 467 | H | H | H | H | —(CH₂)₇—O-Ph |
| 468 | H | H | H | H | —CH(CH₃)CH₂—O-Ph |
| 469 | H | H | H | H | —CH(CH₃)—CH₂-Ph |
| 470 | H | H | H | H | —CH₂CH₂CH₂CH₂—S(O)₂-Ph |
| 471 | H | H | H | H | —CH₂CH₂CH₂CH₂CH₂—S-Ph |

\*Hydrochloride salt
\*\*Tributylamine salt
\*\*\*Tetrabutylammonium salt
\*\*\*\*Trimethyl sulfonium salt

TABLE II $$R^6R^7N-C(R^4)(R^5)-CH_2-C(R^1)(PO_3H_2)(PO_3H_2)$$

| Comp. No. | R¹ | R⁴ | R⁵ | R⁶ | R⁷ |
|---|---|---|---|---|---|
| 140 | H | H | H | H | Phenyl[Ph] |
| 145 | H | H | H | H | H |
| 152* | H | H | H | H | —C₂H₅ |
| 153 | H | H | H | H | -nC₃H₇ |
| 155 | H | H | H | -nC₃H₇ | -nC₃H₇ |
| 156 | H | H | H | H | —CH(CH₃)₂ |
| 157 | H | H | H | H | benzyl |
| 158 | H | H | H | H | -nC₄H₉ |
| 159 | H | —C₂H₅ | H | H | benzyl |
| 161 | H | H | H | H | —CH₂CH(CH₃)₂ |
| 162 | H | H | H | —CH₃ | benzyl |
| 163 | H | H | H | H | cyclopropyl |
| 164 | H | H | H | —C₂H₅ | —C₂H₅ |
| 165 | H | H | H | H | 2-methylbenzyl |
| 166 | H | H | H | H | cyclohexyl |
| 167 | H | H | H | —CH₃ | -nC₃H₇ |
| 169 | —OH | H | H | H | H |
| 174 | —OH | H | H | —CH₃ | benzyl |
| 175 | —OH | H | H | —C₂H₅ | —C₂H₅ |
| 176 | —OH | H | H | H | —CH₂CH₂OCH₂CH₃ |
| 177 | —OH | H | H | H | -iC₃H₇ |
| 178 | —OH | H | H | —CH₂CH₂OCH₂CH₃ | —CH₂CH₂OCH₂CH₃ |
| 179 | —OH | H | H | H | -nC₃H₇ |
| 180 | —OH | H | H | —CH₃ | -nC₅H₁₁ |
| 181 | —OH | H | H | H | —C₂H₅ |
| 182 | —OH | H | H | —CH₃ | —CH₃ |
| 183 | —OH | H | H | —CH₃ | -nC₃H₇ |
| 184 | —OH | H | -iC₃H₇ | H | —CH₃ |
| 185 | —OH | H | -iC₃H₇ | H | benzyl |
| 190 | —OH | H | H | H | -iC₃H₇ |
| 191 | —OH | H | H | —CH₃ | cyclohexyl |
| 192 | —OH | H | -iC₃H₇ | H | 2,4-dichlorobenzyl |
| 193 | —OH | H | H | H | —CH(CH₃)CH₂CH₃ |
| 194 | —OH | H | H | —CH₃ | —CH(CH₃)CH₂CH₃ |
| 195 | —OH | H | H | —C₂H₅ | -nC₃H₇ |
| 196 | —OH | H | H | -nC₃H₇ | -nC₃H₇ |
| 198 | —OH | H | H | H | 1-phenylethyl |
| 199 | —OH | H | H | H | (S)-1-phenylethyl |
| 200 | —OH | H | H | H | (R)-1-phenylethyl |
| 201 | —OH | H | -nC₃H₇ | H | benzyl |
| 202 | —OH | H | -iC₃H₇ | H | 4-methoxybenzyl |
| 203 | —OH | H | -nC₃H₇ | H | 3-trifluoromethylbenzyl |
| 204 | —OH | H | -iC₃H₇ | H | 3-trifluoromethylbenzyl |
| 206 | —OH | H | -nC₃H₇ | H | 3-methoxybenzyl |
| 207 | —OH | H | -nC₃H₇ | H | -nC₃H₇ |
| 208 | —OH | H | -iC₄H₉ | H | benzyl |
| 209 | —OH | H | H | H | benzyl |
| 210 | —OH | H | -iC₃H₇ | H | 2-chlorobenzyl |
| 211 | —OH | H | —CH₃ | H | benzyl |
| 212 | —OH | H | —C₂H₅ | H | benzyl |
| 213 | —OH | H | -iC₃H₇ | H | 4-chlorobenzyl |
| 214 | H | H | H | H | —CH(CH₃)CH₂CH₃ |

TABLE II-continued $$\begin{array}{c} R^6 \\ \diagdown \\ R^7 \end{array} N - \overset{R^4}{\underset{R^5}{C}} - CH_2 - \overset{PO_3H_2}{\underset{PO_3H_2}{C}} - R^1$$

| Comp. No. | $R^1$ | $R^4$ | $R^5$ | $R^6$ | $R^7$ |
|---|---|---|---|---|---|
| 216 | H | H | H | H | –CH(CH₃)–Ph |
| 217 | H | H | H | H | –CH(CH₃)–Ph (stereo) |
| 219 | H | H | H | H | –C₆H₁₃ |
| 220 | H | H | H | H | –CH₂CH₂CH₂CH₂-Ph |
| 221 | H | H | –C₂H₅ | H | H |
| 222 | H | H | H | H | –CH(cyclopropyl)–CH₃ |
| 223 | H | H | H | H | –CH₂CH₂CH₂-Ph |
| 224 | H | H | H | H | –CH(CH₃)-Ph |
| 225 | H | H | H | H | 4-methylbenzyl |
| 226 | H | H | H | H | 4-chlorobenzyl |
| 227 | H | H | H | H | –CH₃ |
| 228 | H | H | H | H | –CH₂CH₂CH(CH₃)₂ |
| 229 | H | H | H | H | 2-chlorobenzyl |
| 230 | H | H | H | H | 4-phenylbenzyl |
| 231 | H | H | H | H | –CH₂–(cyclopropyl) |
| 232 | H | H | H | H | –CH(CH₃)CH(CH₃)₂ |
| 233 | H | H | H | H | –CH₂CH(CH₃)₂ |
| 234 | H | H | H | -nC₃H₇ | benzyl |
| 235 | H | H | H | -nC₃H₇ | –CH₂CH(CH₃)₂ |
| 236 | H | H | H | –C₂H₅ | -nC₃H₇ |
| 237 | H | H | H | H | –CH(CH₃)-cyclohexyl (stereo) |
| 238 | H | H | H | H | –CH(CH₃)-cyclohexyl (stereo) |
| 239 | H | H | –CH₃ | H | -nC₄H₉ |
| 240 | H | H | H | H | –CH(CH₃)(CH₂CH₃) (stereo) |
| 241 | H | H | H | H | –CH(CH₃)(CH₂CH₃) (stereo) |
| 242 | H | H | H | H | -nC₅H₉ |

TABLE II-continued

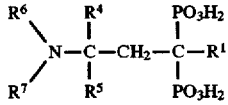

| Comp. No. | R¹ | R⁴ | R⁵ | R⁶ | R⁷ |
|---|---|---|---|---|---|
| 243 | H | H | H | H |  |
| 244 | H | H | —C₂H₅ | H | 2-chlorobenzyl |
| 247 | H | H | —C₂H₅ | H | 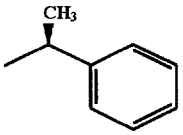 |
| 248 | H | H | —C₂H₅ | H | -nC₄H₉ |
| 257 | H | nC₃H₇ | H | H | benzyl |
| 258 | H | H | -nC₅H₁₁ | H | H |
| 259 | H | H | -iC₃H₇ | H | H |
| 260 | H | H | H | H | —CH₂CH₂CH₂OH |
| 261 | H | -iC₃H₇ | H | H | benzyl |
| 262 | H | H | -nC₃H₇ | H | H |
| 263 | H | H | benzyl | H | H |
| 472 | H | —CH₃ | H | H | H |
| 473 | H | —CH₃ | —CH₃ | H | H |
| 474 | H | H | -nC₃H₇ | H | H |
| 475 | H | H | -nC₄H₉ | H | H |
| 476 | H | H | —CH₂CH₂CH₂CH₂CH₂— | | H |
| 477 | H | H | —(CH₂)₂CH=CH₂ | H | H |
| 478 | H | H | -iC₄H₉ | H | H |
| 479 | H | H | -sC₄H₉ | H | H |
| 480 | H | H | —CH₂CH₂-Ph | H | H |

*Diammonium salt

TABLE III

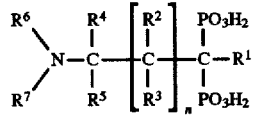

| Comp. No. | n | R¹ | R² | R³ | R⁴ | R⁵ | R⁶ | R⁷ |
|---|---|---|---|---|---|---|---|---|
| 249* | 3 | H | H | H | H | H | H | H |
| 250* | 3 | H | H | H | H | H | H | benzyl |
| 253 | 2 | —OH | H | H | H | H | H | —CH₃ |
| 254 | 2 | —OH | H | H | H | H | H | —C₂H₅ |
| 481 | 3 | H | H | H | H | H | H | —C₂H₅ |

*Triammonium salt

TABLE IV

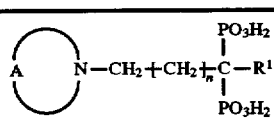

| Comp. No. | n | R¹ | A |
|---|---|---|---|
| 3 | 0 | H | —N=CH—N=CH— |
| 4 | 0 | H | —CH₂CH₂CH₂CH₂— |
| 5* | 0 | H | —CH₂CH₂CH₂CH₂— |
| 6 | 0 | H | —CH₂CH₂CH₂CH₂CH₂— |
| 7 | 0 | —OH | —CH=N—CH=CH— |

TABLE IV-continued $$\text{A} \bigcirc \text{N}-\text{CH}_2+\text{CH}_2\frac{1}{n}\overset{\overset{\displaystyle PO_3H_2}{|}}{\underset{\underset{\displaystyle PO_3H_2}{|}}{C}}-R^1$$

| Comp. No. | n | R¹ | A |
|---|---|---|---|
| 11** | 0 | H | —CH₂CH₂CH₂CH₂— |
| 13*** | 0 | H | —CH₂CH₂CH₂CH₂— |
| 20 | 0 | H | —CH(CH₃)—CH₂—CH₂—CH₂—CH₂— |
| 21 | 0 | H | —CH(CH₃)—CH₂—CH₂—CH(CH₃)— |
| 37 | 0 | H | —CH₂—CH(CH₃)—CH₂—CH₂—CH₂— |
| 48 | 0 | H | —CH₂CH₂CH₂CH₂CH₂CH₂— |
| 49 | 0 | H | CH₂—CH₂—CH(CH₃)—CH₂—CH₂— |
| 53 | 0 | H | —CH₂—CH(CH₃)—O—CH(CH₃)—CH₂— |
| 55 | 0 | H | —CH₂—CH(CH₃)—CH₂—CH(CH₃)—CH₂— |
| 59 | 0 | H | —CH₂CH₂—O—CH₂CH₂— |
| 65 | 0 | H | —CH(CH₃)—CH₂—CH₂—CH₂— |
| 71 | 0 | H | —CH₂—CH=CH—CH₂—CH₂— |
| 73 | 0 | H | —CH₂—C(CH₃)₂—CH₂—CH₂—CH₂— |
| 84 | 0 | H | —C(CH₃)=N—CH₂—CH₂—CH₂— |
| 87 | 0 | H | —CH(C₂H₅)—CH₂—CH₂—CH₂—CH₂— |
| 91 | 0 | H | —CH(CH₃)—CH(CH₃)—CH₂—CH₂—CH₂— |
| 92 | 0 | H | —CH=N—C(CH₃)=CH— |
| 94 | 0 | H | —CH(CH₃)—CH₂—CH(CH₃)—CH₂—CH₂— |
| 96 | 0 | H | —N=CH—C(CH₃)=CH— |
| 97 | 0 | H | —C(CH₃)=N—CH=CH— |
| 100 | 0 | H | —CH(CH₃)—CH₂—CH₂—CH(CH₃)—CH₂— |
| 101 | 0 | H | —CH₂CH₂CH₂— |

TABLE IV-continued $$\underset{A}{\bigcirc}N-CH_2+CH_2\underset{n}{\overset{PO_3H_2}{\underset{PO_3H_2}{|}}}C-R^1$$

| Comp. No. | n | R¹ | A |
|---|---|---|---|
| 109 | 0 | H | $-\underset{\underset{CH_3}{|}}{C}=N-\underset{\underset{CH_3}{|}}{C}=CH-$ |
| 110 | 0 | H | $-CH=N-CH=CH-$ |
| 112 | 0 | H | $-CH_2CH_2CH_2-$ (o-phenylene) |
| 113 | 0 | H | $-CH=N-\underset{\underset{Ph}{|}}{C}=CH-$ |
| 114 | 0 | H | $-CH_2CH_2-$ (cyclohexylene) |
| 115 | 0 | H | $-\underset{\underset{CH_3}{|}}{CH}-CH_2-CH_2-\underset{\underset{C_2H_5}{|}}{CH}-CH_2-$ |
| 116 | 0 | H | $-\underset{\underset{Ph}{|}}{C}=N-CH=CH-$ |
| 117 | 0 | H | $-\underset{\underset{nC_3H_7}{|}}{CH}-CH_2-CH_2-CH_2-CH_2-$ |
| 119 | 0 | H | $-\underset{\underset{C_2H_5}{|}}{C}=N-CH=CH-$ |
| 126 | 0 | H | $-CH_2-CH_2-\underset{\underset{CH_2CH_2CH_2-Ph}{|}}{CH}-CH_2-CH_2-$ |
| 127 | 0 | H | $-CH_2CH_2-$ (cyclohexylene) |
| 128 | 0 | H | $-CH_2-CH_2-\underset{\underset{CH_2-Ph}{|}}{CH}-CH_2-CH_2-$ |
| 129 | 0 | H | $-CH_2-CH_2-\underset{\underset{C_2H_5}{|}}{CH}-CH_2-CH_2-$ |
| 130**** | 0 | H | $-CH=N-CH_2CH_2CH_2-$ |
| 160 | 1 | H | $-CH_2CH_2CH_2CH_2-$ |
| 168 | 1 | H | $-CH_2CH_2CH_2CH_2CH_2-$ |
| 172 | 1 | -OH | $-CH_2CH_2CH_2CH_2CH_2-$ |
| 173 | 1 | -OH | $-CH_2-CH_2-\underset{\underset{CH_3}{|}}{CH}-CH_2-CH_2-$ |
| 186 | 1 | -OH | $-CH=N-CH=CH-$ |
| 187 | 1 | -OH | $-CH_2CH_2-O-CH_2CH_2-$ |
| 197 | 1 | -OH | $-CH_2CH_2CH_2-$ |
| 215 | 1 | H | $-CH_2CH_2-O-CH_2CH_2-$ |
| 255 | 2 | -OH | $-CH=N-CH=CH-$ |

TABLE IV-continued $$\underset{A}{\bigcirc}N-CH_2+CH_2+_n \underset{PO_3H_2}{\overset{PO_3H_2}{\underset{|}{C}}}-R^1$$

| Comp. No. | n | R¹ | A |
|---|---|---|---|
| 264 | 0 | H | $-CH_2CH(OH)CH_2CH_2CH_2-$ |
| 265 | 0 | H | $-CH_2CH=CH-CH_2-$ |
| 266 | 0 | H | $-\underset{\underset{Ph}{\|}}{CH}-CH_2-CH_2-CH_2-CH_2-$ |
| 268 | 0 | H | $-\underset{\underset{CH_2\text{-}Ph}{\|}}{CH}-CH_2-CH_2-CH_2-CH_2-$ |
| 275 | 0 | H | $-\underset{\underset{CH(CH_3)_2}{\|}}{CH}-CH_2-CH_2-CH_2-CH_2-$ |
| 278 | 0 | H | $-\underset{\underset{C_2H_5}{\|}}{CH}-CH_2-CH_2-\underset{\underset{C_2H_5}{\|}}{CH}-CH_2-$ |
| 283 | 0 | H | $-\underset{\underset{CH_2CH_2CH_3}{\|}}{CH}-CH_2-CH_2-CH_2-CH_2-$ |
| 285 | 0 | H | $-CH=N-\underset{\underset{Br}{\|}}{C}=CH-$ |
| 288 | 0 | H | $-CH=N-\underset{\underset{Cl}{\|}}{C}=\underset{\underset{Cl}{\|}}{C}-$ |
| 291 | 0 | H | $-CH_2CH_2-\text{C}_6\text{H}_4-CH_2-$ (ortho) |
| 293 | 0 | H | $-N=CH-\text{C}_6\text{H}_4(NO_2)-$ |
| 300 | 0 | H | $-CH_2-CH_2-\underset{\underset{OH}{\|}}{CH}-CH_2-CH_2-$ |
| 301 | 0 | H | $-CH_2-\underset{\underset{CH_2CH_2\text{-}Ph}{\|}}{CH}-CH_2-CH_2-CH_2-$ |
| 301 | 0 | H | $-CH_2-\underset{\underset{CH_2CH_2\text{-cyclohexyl}}{\|}}{CH}-CH_2-CH_2-CH_2-$ |
| 302 | 0 | H | $-\underset{\underset{CH_2CH_2CH_2CH_2CH_2CH_3}{\|}}{CH}-CH_2-CH_2-CH_2-CH_2-$ |
| 305 | 0 | H | $-CH_2-CH_2-CH_2-CH_2-\underset{\underset{CH_2CH_2CH_2\text{-cyclohexyl}}{\|}}{CH}-$ |
| 306 | 0 | H | $-CH_2-CH_2-CH_2-\underset{\underset{CH_2\text{-Ph}}{\|}}{CH}-CH_2-$ |
| 307 | 0 | H | $-CH_2-CH_2-CH_2-CH_2-\underset{\underset{CH_2CH_2CH_2\text{-Ph}}{\|}}{CH}-$ |

TABLE IV-continued $$\underset{A}{\bigcirc}N-CH_2 + CH_2 \underset{n}{)} \overset{PO_3H_2}{\underset{PO_3H_2}{\overset{|}{C}}} -R^1$$

| Comp. No. | n | R¹ | A |
|---|---|---|---|
| 310 | 0 | H | cyclohexane-1,2-diyl-bis(CH₂CH₂—, —CH₂—) |
| 316 | 0 | H | —CH₂—CH₂—CH(CH₂CH₂-Ph)—CH₂—CH₂— |
| 321 | 0 | H | —CH₂—CH₂—CH₂—CH₂—CH(CH₂CH₂-Ph)— |
| 322 | 0 | H | —CH₂—CH₂—CH(CH(CH₃)₂)—CH₂—CH₂— |
| 325 | 0 | H | —CH₂—CH(C₂H₅)—CH₂—CH₂—CH₂— |
| 328 | 0 | H | —CH₂—CH=CH—CH₂—CH(CH₃)— |
| 339 | 0 | H | —CH(CH₂OH)—CH₂—CH₂—CH₂—CH₂— |
| 340 | 0 | H | —CH₂—CH₂—CH(CH₂OH)—CH₂—CH₂— |
| 342 | 0 | H | —CH₂—CH(CH₂OH)—CH₂—CH₂—CH₂— |
| 354 | 0 | H | —CH₂CH₂CH₂CH₂CH₂CH₂CH₂CH₂— |
| 355 | 0 | H | —CH₂—CH(CH₂CH₂CH₂CH₃)—CH₂—CH₂—CH₂— |
| 359 | 0 | H | —CH₂—CH₂—CH₂—CH(CH₂OH)— |
| 360 | 0 | H | —CH₂—CH₂—C(CH₃)(Cl)—CH₂—CH₂— |
|  | 0 | H | —CH₂—CH₂—C(CH₃)(OH)—CH₂—CH₂— |
| 366 | 0 | H | —CH₂—CH=CH—CH₂—CH(CH₂CH₃)— |
| 369 | 0 | H | —CH₂—CH₂—CH(CH₂NH₂)—CH₂—CH₂— |
|  | 0 | H | —CH₂CH₂—NH—CH₂CH₂— |
| 379 | 0 | H | —CH(CH₂CH₂OH)—CH₂—CH₂—CH₂—CH₂— |

TABLE IV-continued $$\underset{A}{\bigcirc}N-CH_2+CH_2\underset{n}{]}\underset{\underset{PO_3H_2}{|}}{\overset{\overset{PO_3H_2}{|}}{C}}-R^1$$

| Comp. No. | n | R¹ | A |
|---|---|---|---|
| 380 | 0 | H | -CH₂-CH(COOH)-CH₂-CH₂-CH₂- |
| 381 | 0 | H | -CH₂-CH₂-CH(COOH)-CH₂-CH₂- |
| 386 | 0 | H | -CH(C(O)-O-CH₂CH₃)-CH₂-CH₂-CH₂-CH₂- |
| 397 | 0 | H | -CH₂-CH₂-CH(CH₂CH₂CH₃)-CH₂-CH₂- |
| 402 | 0 | H | -CH₂-CH(CH₂COOH)-CH₂-CH₂-CH₂- |
| 407 | 0 | H | -CH₂-CH(CH₂PO₃H₂)-CH₂-CH₂-CH₂- |
| 411 | 0 | H | -CH₂-CH(C(O)-NH₂)-CH₂-CH₂-CH₂- |
| 419 | 0 | H | -CH₂-CH(CH₂CH₂CH₂OH)-CH₂-CH₂-CH₂- |
| 429 | 0 | H | -CH₂-CH(CH₂NH-C(O)-NHCH₃)-CH₂-CH₂-CH₂- |
| 431 | 0 | H | -CH₂-CH(CH₂-O-CH₂CH₂CH₃)-CH₂-CH₂-CH₂- |
| 464 | 0 | H | -CH₂-CH₂-CH₂-CH(CH₂CH₂CH₂CH₂CH₂CH₂CH₂CH₃)-CH₂- |
| 481 | 1 | -NH₂ | -CH₂CH₂CH₂CH₂CH₂- |

*Tetramethylammonium salt
**Tributylamine salt
***Trimethylsulfonium salt
****Diammonium salt

TABLE V $$X-\left[\underset{R^3}{\overset{R^2}{\underset{|}{\overset{|}{C}}}}\right]_n-\underset{\underset{PO_3H_2}{|}}{\overset{\overset{PO_3H_2}{|}}{C}}-R^1$$

| Comp. No. | n | R¹ | R² | R³ | X |
|---|---|---|---|---|---|
| 9 | 0 | -OH | — | — | 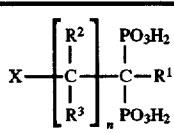 |
| 10* | 0 | -OH | — | — | 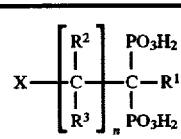 |

TABLE V-continued $$X-\left[\underset{R^3}{\overset{R^2}{\underset{|}{\overset{|}{C}}}}\right]_n-\underset{\underset{PO_3H_2}{|}}{\overset{\overset{PO_3H_2}{|}}{C}}-R^1$$

| Comp. No. | n | R¹ | R² | R³ | X |
|---|---|---|---|---|---|
| 17 | 0 | H | — | — | 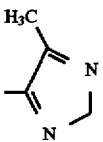 |

TABLE V-continued $$X-\left[\begin{array}{c}R^2\\|\\C\\|\\R^3\end{array}\right]_n\begin{array}{c}PO_3H_2\\|\\C-R^1\\|\\PO_3H_2\end{array}$$

| Comp. No. | n | $R^1$ | $R^2$ | $R^3$ | X |
|---|---|---|---|---|---|
| 19 | 0 | —OH | — | — | 2-piperidinyl |
| 139 | 1 | H | H | H | 2-methylquinolinyl |
| 141 | 1 | H | H | H | 2-piperidinyl |
| 142** | 1 | H | H | H | 2-piperidinyl |
| 143 | 1 | H | H | H | 1-acetyl-2-piperidinyl |
| 144*** | 1 | H | H | H | 2-piperidinyl |
| 146* | 1 | H | H | H | 2-piperidinyl |
| 147 | 1 | H | H | H | 3-methyl-2-piperidinyl |
| 148 | 1 | H | H | H | 5-methyl-2-piperidinyl |
| 149 | 1 | H | H | H | 2,6-dimethyl-piperidinyl |
| 150** | 1 | H | H | H | 4-methyl-2-piperidinyl |
| 151** | 1 | H | H | H | 3-methyl-2-piperidinyl (H₃C substituent) |
| 154 | 1 | H | H | H | 5-ethyl-2-piperidinyl |
| 170 | 1 | —OH | H | H | imidazolyl |
| 171 | 1 | —OH | H | H | 2-pyrrolidinyl |
| 188 | 1 | —OH | H | H | 1-(N-methylamino)-2-piperidinyl |
| 189 | 1 | —OH | H | H | 2-piperidinyl |
| 205 | 1 | —OH | H | H | 3-piperidinyl |
| 218 | 1 | H | H | —CH₃ | 2-piperidinyl |
| 245**** | 1 | H | H | H | 2-pyrrolidinyl |
| 251 | 1 | H | H | H | 8-quinolinyl |
| 252 | 1 | H | H | H | 3-piperidinylmethyl |

TABLE V-continued

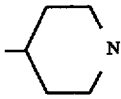

| Comp. No. | n | R¹ | R² | R³ | X |
|---|---|---|---|---|---|
| 256 | 1 | —OH | H | H | (piperidinyl) |

*Tributylammonium salt  
**Tetramethylammonium salt  
***Sodium salt  
****Triammonium salt

HERBICIDAL SCREENING TESTS

The compounds listed in the foregoing tables were tested for herbicidal activity by various methods and at various rates of application. The results of some of these tests are given below. Results obtained in herbicidal screening are affected by a number of factors including: the amount of sunlight, soil type, soil pH, temperature, humidity, depth of planting, plant growth stage, application rate as well as many other factors. All testing procedures are administered with the least amount of variability possible. State of the art equipment and techniques are employed to enable the screening process to remain consistent and reliable.

PRE-EMERGENCE HERBICIDAL SCREENING TEST

On the day preceding treatment, seeds of several different weed species were planted in sandy loam soil containing only trace organic matter. Propagules were sown in individual rows using one species per row across the width of an aluminum flat (19.5×9.5×6 cm). The grass weeds planted were green foxtail (*Setaria viridis*) ("SETVI"), wild oat (*Avena fatua*) ("AVEFA"), barnyardgrass (*Echinochloa crusgalli*) ("ECHCG"). Broadleaf weeds utilized were wild mustard (*Sinapis arvensis*) ("SINAR"), velvetleaf (*Abutilon theophrasti*) ("ABUTH") and morningglory (Ipomoea spp.) ("IPOSS"). Additionally, yellow nutsedge (*Cyperus esculentus*) ("CYPES"), nutlets were sown. Seeding depths ranged from 1.0 to 1.5 cm and plant densities ranged from 3 to 25 plants per row depending on individual plant species.

Solutions of the test compounds were prepared by weighing out 18.8 and 74.7 mg for 1.0 and 4.0 kilograms (acid equivalent) per hectare (kg/ha) applications, respectively, of the test compound into a 60 ml wide-mouth bottle, then dissolving the compound in 14.0 ml of deionized water containing 0.5% v/v Tween 20®(polyoxyethylene sorbitan monolaurate emulsifier) as a surfactant. Additional solvents, not exceeding 2 ml (15% of spray volume), were used if needed to dissolve the compound.

The soil surface was sprayed inside an enclosed linear spray table with the nozzle set at 30.5 cm (12 inches) above the soil line. The spray table was calibrated to deliver 748 L/ha (80 gal/A) with the application rate being 4.0 kg/ha or 1.0 kg/ha. After treatment, the flats were placed into a greenhouse and watered as needed. The greenhouse environmental systems provided the plants with natural and artificial (via metal halide lamps) lighting to attain 14 hours of light per day. Day and night temperatures were maintained at 29° and 21° C., respectively.

The degree of weed control was evaluated and recorded 17–21 days after treatment as a percentage of weed control as compared to the growth of the same species of the same age in an untreated control flat. Percent control is the total injury to the plants due to all factors including: inhibited emergence, stunting, malformation, chlorosis and other types of plant injury. The control ratings range from 0 to 100 percent, where 0% represents no effect with growth equal to the untreated control and where 100% represents complete kill. A dash (-) indicates that no test was performed at that level of application.

POST-EMERGENCE HERBICIDAL EVALUATION

The soil was prepared and seeded with the same species and methodology described for the pre-emergence test. Post-emergence flats were placed in the greenhouse under the same environmental conditions as described for the pre-emergence flats and watered as needed. Plants were grown for 10 to 12 days (or to the appropriate growth stage) prior to compound application. Grasses were sprayed at a 3 to 4 leaf stage and broadleaves at a 1 to 2 leaf stage. Yellow nutsedge was 5 to 7 cm tall at application.

Plants were sprayed 30.5 cm (12 inches) above the foliage with the same spray solution as prepared for the pre-emergence test. The application rate was 4.0 kg/ha or 1.0 kg/ha. Treated plants were then returned to a greenhouse and watered daily without wetting the foliage. The degree of weed control was evaluated 17–21 days after application and recorded as percentage of control as compared to the growth of the same species in an untreated control flat of the same age. The percent control scale (0–100%) used to evaluate the pre-emergence treatment was also applied to the post-emergence treatment, with a dash (-) again indicating that no test was performed at that level of application.

TABLE VI

Post-Emergence Testing

| Comp. No. | Rate kg/ha | AVEFA | ECHCG | SETVI | ABUTH | IPOSS | SINAR | CYPES |
|---|---|---|---|---|---|---|---|---|
| 1 | 4.0 | 0 | 0 | 0 | 0 | — | 0 | 0 |
| 2 | 4.0 | 5 | 95 | 95 | 25 | 60 | 90 | 20 |
| 3 | 4.0 | 10 | 5 | 30 | 0 | 5 | 60 | 0 |
| 4 | 4.0 | 100 | 100 | 100 | 100 | 100 | 100 | 50 |
| 5 | 4.0 | 100 | 100 | 100 | 100 | 100 | 100 | 80 |
| 6 | 4.0 | 100 | 100 | 100 | 70 | 100 | 100 | 20 |
| 7 | 4.0 | 60 | 100 | 100 | 75 | 70 | 100 | 10 |
| 8 | 4.0 | 0 | 0 | 0 | 0 | 0 | 0 | 0 |
| 9 | 4.0 | 0 | 0 | 60 | 0 | 0 | 90 | 5 |
| 10 | 4.0 | 10 | 10 | 70 | 5 | 10 | 80 | 15 |
| 11 | 1.0 | 100 | 95 | 95 | 80 | 70 | 100 | 25 |

TABLE VI-continued

Post-Emergence Testing

| Comp. No. | Rate kg/ha | AVEFA | ECHCG | SETVI | ABUTH | IPOSS | SINAR | CYPES |
|---|---|---|---|---|---|---|---|---|
| 12 | 1.0 | 100 | 100 | 100 | 70 | 95 | 100 | 30 |
| 13 | 1.0 | 60 | 90 | 100 | 20 | 20 | 100 | 5 |
| 14 | 4.0 | 98 | 98 | 98 | 60 | 60 | 100 | 10 |
| 15 | 4.0 | 50 | 60 | 60 | 15 | 70 | 100 | 25 |
| 16 | 4.0 | 85 | 50 | 60 | 5 | 60 | 100 | 15 |
| 17 | 4.0 | 0 | 0 | 10 | 0 | 0 | 10 | 0 |
| 18 | 4.0 | 5 | 5 | 50 | 0 | 5 | 85 | 0 |
| 19 | 4.0 | 60 | 30 | 100 | 30 | 30 | 100 | 15 |
| 20 | 4.0 | 100 | 85 | 85 | 50 | 90 | 100 | 5 |
| 21 | 4.0 | 30 | 50 | 50 | 0 | 30 | 95 | 0 |
| 22 | 4.0 | 100 | 98 | 98 | 98 | 90 | 100 | 70 |
| 23 | 1.0 | 40 | 40 | 80 | 15 | 10 | 95 | 5 |
| 24 | 1.0 | 100 | 100 | 100 | 70 | 100 | 100 | 25 |
| 25 | 1.0 | 100 | 100 | 100 | 60 | 100 | 100 | 20 |
| 27 | 1.0 | 70 | 90 | 95 | 20 | 10 | 85 | 15 |
| 28 | 1.0 | 0 | 0 | 0 | 0 | 0 | 0 | 0 |
| 29 | 1.0 | 80 | 100 | 90 | 10 | 10 | 100 | 20 |
| 30 | 1.0 | 75 | 50 | 60 | 0 | 10 | 50 | 0 |
| 31 | 1.0 | 90 | 70 | 80 | 20 | 10 | 10 | 30 |
| 32 | 1.0 | 100 | 98 | 98 | 30 | 70 | 100 | 50 |
| 33 | 1.0 | 100 | 100 | 98 | 100 | 60 | 100 | 10 |
| 34 | 1.0 | 5 | 10 | 40 | 0 | 0 | 50 | 0 |
| 35 | 1.0 | 5 | 0 | 60 | 10 | 0 | 10 | 0 |
| 36 | 1.0 | 40 | 60 | 50 | 0 | 0 | 10 | 15 |
| 37 | 1.0 | 50 | 30 | 50 | 0 | 10 | 30 | 5 |
| 38 | 1.0 | 0 | 15 | 20 | 5 | 5 | 40 | 0 |
| 39 | 4.0 | 0 | 0 | 0 | 0 | 0 | 0 | 0 |
| 40 | 1.0 | 98 | 98 | 85 | 0 | 5 | 30 | 10 |
| 41 | 1.0 | 95 | 60 | 95 | 0 | 0 | 98 | 25 |
| 42 | 1.0 | 100 | 100 | 100 | 98 | 90 | 100 | 85 |
| 43 | 1.0 | 80 | 80 | 60 | 20 | 10 | 40 | 5 |
| 44 | 1.0 | 80 | 90 | 90 | 75 | 5 | 100 | 75 |
| 45 | 1.0 | 80 | 85 | 50 | 15 | 5 | 60 | 5 |
| 46 | 1.0 | 80 | 50 | 40 | 5 | 10 | 15 | 15 |
| 47 | 1.0 | 60 | 5 | 30 | 5 | 5 | 50 | 10 |
| 48 | 1.0 | 60 | 60 | 60 | 0 | 15 | 85 | 0 |
| 49 | 1.0 | 90 | 90 | 95 | 5 | 30 | 100 | 5 |
| 50 | 1.0 | 0 | 0 | 0 | 0 | 0 | 0 | 0 |
| 51 | 1.0 | 100 | 95 | 100 | 75 | 85 | 100 | 25 |
| 52 | 1.0 | 100 | 100 | 95 | 50 | 65 | 100 | 10 |
| 53 | 1.0 | 5 | 0 | 5 | 0 | 5 | 25 | 0 |
| 54 | 1.0 | 95 | 95 | 95 | 60 | 60 | 100 | 15 |
| 55 | 1.0 | 98 | 15 | 50 | 0 | 30 | 25 | 0 |
| 56 | 1.0 | 0 | 0 | 0 | 0 | 0 | 0 | 0 |
| 57 | 1.0 | 95 | 95 | 100 | 10 | 15 | 98 | 10 |
| 58 | 1.0 | 40 | 70 | 90 | 25 | 5 | 20 | 5 |
| 59 | 1.0 | 95 | 25 | 40 | 5 | 95 | 15 | 0 |
| 60 | 1.0 | 100 | 100 | 100 | 70 | 90 | 100 | 10 |
| 61 | 1.0 | 20 | 0 | 5 | 0 | 0 | 0 | 0 |
| 62 | 1.0 | 85 | 90 | 80 | 10 | 10 | 95 | 10 |
| 63 | 1.0 | 100 | 95 | 95 | 85 | 85 | 100 | 60 |
| 64 | 1.0 | 100 | 95 | 95 | 10 | 90 | 100 | 20 |
| 65 | 1.0 | 100 | 98 | 98 | 30 | 60 | 100 | 5 |
| 66 | 1.0 | 95 | 60 | 75 | 5 | 10 | 20 | 20 |
| 67 | 1.0 | 95 | 70 | 30 | 10 | 10 | 10 | 10 |
| 68 | 1.0 | 30 | 20 | 30 | 0 | 5 | 20 | 15 |
| 69 | 1.0 | 10 | 30 | 20 | 0 | 10 | 10 | 10 |
| 70 | 1.0 | 90 | 100 | 100 | 60 | 10 | 90 | 60 |
| 71 | 1.0 | 100 | 100 | 100 | 90 | 100 | 100 | 50 |
| 72 | 1.0 | 50 | 15 | 20 | 5 | 0 | 5 | 10 |
| 73 | 1.0 | 0 | 0 | 10 | 0 | 0 | 5 | 0 |
| 74 | 1.0 | 100 | 98 | 95 | 60 | 95 | 100 | 50 |
| 75 | 1.0 | 60 | 50 | 15 | 5 | 10 | 10 | 10 |
| 76 | 1.0 | 50 | 15 | 10 | 5 | 5 | 15 | 5 |
| 77 | 1.0 | 60 | 10 | 5 | 0 | 5 | 5 | 5 |
| 78 | 1.0 | 75 | 30 | 15 | 10 | 10 | 5 | 5 |
| 79 | 1.0 | 90 | 70 | 25 | 5 | 15 | 25 | 10 |
| 80 | 1.0 | 50 | 60 | 85 | 5 | 5 | 85 | 5 |
| 81 | 1.0 | 98 | 100 | 98 | 10 | 15 | 100 | 30 |
| 82 | 1.0 | 100 | 100 | 98 | 50 | 35 | 100 | 30 |
| 83 | 1.0 | 100 | 98 | 98 | 15 | 25 | 100 | 50 |
| 84 | 1.0 | 15 | 40 | 20 | 0 | 10 | 90 | 0 |
| 85 | 1.0 | 100 | 98 | 98 | 70 | 15 | 100 | 5 |
| 86 | 1.0 | 100 | 100 | 100 | 75 | 20 | 100 | 20 |

TABLE VI-continued

Post-Emergence Testing

| Comp. No. | Rate kg/ha | AVEFA | ECHCG | SETVI | ABUTH | IPOSS | SINAR | CYPES |
|---|---|---|---|---|---|---|---|---|
| 87 | 1.0 | 98 | 100 | 98 | 70 | 30 | 90 | 5 |
| 88 | 1.0 | 0 | 0 | 10 | 0 | 5 | 10 | 0 |
| 89 | 1.0 | 75 | 80 | 100 | 60 | 10 | 100 | 30 |
| 90 | 1.0 | 100 | 100 | 100 | 95 | 98 | 100 | 60 |
| 91 | 1.0 | 100 | 100 | 100 | 80 | 90 | 100 | 15 |
| 92 | 1.0 | 100 | 98 | 100 | 98 | 90 | 100 | 10 |
| 93 | 1.0 | 0 | 10 | 10 | 10 | 5 | 10 | 0 |
| 94 | 1.0 | 40 | 40 | 80 | 10 | 15 | 15 | 10 |
| 95 | 1.0 | 85 | 90 | 95 | 30 | 20 | 90 | 5 |
| 96 | 1.0 | 10 | 30 | 30 | 10 | 5 | 20 | 0 |
| 97 | 1.0 | 100 | 98 | 95 | 50 | 50 | 98 | 5 |
| 98 | 1.0 | 100 | 98 | 95 | 70 | 100 | 100 | 15 |
| 99 | 1.0 | 100 | 100 | 90 | 70 | 30 | 90 | 10 |
| 100 | 1.0 | 100 | 60 | 70 | 40 | 20 | 30 | 0 |
| 101 | 1.0 | 50 | 90 | 70 | 10 | 25 | 100 | 5 |
| 102 | 1.0 | 100 | 85 | 95 | 15 | 30 | 85 | 10 |
| 103 | 1.0 | 0 | 5 | 10 | 20 | 5 | 10 | 0 |
| 104 | 1.0 | 75 | 70 | 60 | 10 | 5 | 20 | 5 |
| 105 | 1.0 | 50 | 60 | 15 | 5 | 5 | 15 | 10 |
| 106 | 1.0 | 50 | 50 | 50 | 0 | 5 | 15 | 10 |
| 107 | 1.0 | 60 | 30 | 30 | 5 | 10 | 30 | 10 |
| 108 | 1.0 | 30 | 50 | 20 | 5 | 5 | 15 | 0 |
| 109 | 1.0 | 85 | 90 | 98 | 30 | 15 | 100 | 5 |
| 110 | 1.0 | 100 | 98 | 100 | 75 | 100 | 100 | 30 |
| 111 | 1.0 | 10 | 15 | 10 | 5 | 10 | 20 | 0 |
| 112 | 1.0 | 0 | 5 | 10 | 0 | 5 | 10 | 0 |
| 113 | 1.0 | 0 | 10 | 5 | 0 | 5 | 5 | 0 |
| 114 | 1.0 | 100 | 98 | 98 | 70 | 20 | 98 | 5 |
| 115 | 1.0 | 100 | 70 | 40 | 5 | 10 | 20 | 0 |
| 130 | 1.0 | 95 | 100 | 100 | 100 | 100 | 100 | 5 |
| 139 | 4.0 | 0 | 0 | 0 | 0 | — | 0 | 0 |
| 140 | 4.0 | 0 | 5 | 20 | 0 | — | 10 | 0 |
| 141 | 1.0 | 90 | 100 | 100 | 100 | 100 | 100 | 20 |
| 142 | 4.0 | 100 | 100 | 100 | 100 | 100 | 100 | 30 |
| 143 | 4.0 | 20 | 5 | 25 | 0 | 15 | 100 | 0 |
| 144 | 4.0 | 100 | 100 | 100 | 100 | 100 | 100 | 50 |
| 145 | 4.0 | 5 | 10 | 95 | 60 | 90 | 100 | 70 |
| 146 | 1.0 | 90 | 100 | 100 | 100 | 100 | 100 | 25 |
| 147 | 1.0 | 100 | 100 | 98 | 60 | 40 | 100 | 15 |
| 148 | 1.0 | 98 | 100 | 95 | 85 | 60 | 100 | 10 |
| 149 | 1.0 | 10 | 5 | 10 | 10 | 0 | 30 | 0 |
| 150 | 4.0 | 70 | 99 | 90 | 75 | 80 | — | 20 |
| 151 | 4.0 | 78 | 97 | 98 | 80 | 85 | — | 25 |
| 152 | 1.0 | 100 | 95 | 98 | 75 | 40 | 100 | 25 |
| 153 | 1.0 | 90 | 95 | 98 | 50 | 70 | 98 | 20 |
| 154 | 1.0 | 80 | 95 | 95 | 70 | 15 | 90 | 15 |
| 155 | 1.0 | 95 | 95 | 98 | 60 | 15 | 80 | 10 |
| 156 | 1.0 | 10 | 50 | 95 | 0 | 20 | 20 | 10 |
| 157 | 1.0 | 100 | 98 | 100 | 95 | 20 | 40 | 60 |
| 158 | 1.0 | 60 | 60 | 75 | 100 | 10 | 20 | 10 |
| 159 | 1.0 | 98 | 98 | 100 | 100 | 15 | 70 | 15 |
| 160 | 1.0 | 100 | 98 | 95 | 100 | 70 | 100 | 15 |
| 161 | 1.0 | 80 | 90 | 98 | 100 | 75 | 100 | 50 |
| 162 | 1.0 | 60 | 70 | 70 | 30 | 10 | 30 | 10 |
| 163 | 1.0 | 80 | 75 | 95 | 70 | 20 | 60 | 30 |
| 164 | 1.0 | 70 | 90 | 90 | 20 | 20 | 100 | 10 |
| 165 | 1.0 | 85 | 90 | 98 | 40 | 20 | 30 | 40 |
| 166 | 1.0 | 70 | 80 | 90 | 10 | 25 | 100 | 50 |
| 167 | 1.0 | 100 | 95 | 98 | 95 | 85 | 100 | 40 |
| 168 | 1.0 | 80 | 85 | 90 | 25 | 15 | 95 | 5 |
| 169 | 4.0 | 10 | 60 | 60 | 10 | 0 | 25 | 5 |
| 170 | 4.0 | 15 | 20 | 90 | 30 | 30 | 100 | 5 |
| 171 | 4.0 | 100 | 100 | 100 | 100 | 75 | 100 | 15 |
| 172 | 4.0 | 5 | 20 | 60 | 0 | 30 | 90 | 0 |
| 173 | 4.0 | 0 | 0 | 0 | 0 | 0 | 0 | 0 |
| 174 | 4.0 | 20 | 50 | 40 | 25 | 0 | 15 | 15 |
| 175 | 4.0 | 15 | 15 | 90 | 40 | 20 | 100 | 0 |
| 176 | 4.0 | 0 | 5 | 5 | 0 | 0 | 15 | 0 |
| 177 | 4.0 | 0 | 0 | 15 | 0 | 5 | 15 | 0 |
| 178 | 4.0 | 5 | 0 | 10 | 0 | 5 | 15 | 0 |
| 179 | 4.0 | 85 | 85 | 90 | 25 | 20 | 90 | 10 |
| 180 | 4.0 | 30 | 50 | 98 | 25 | 5 | 100 | 0 |
| 181 | 4.0 | 25 | 50 | 85 | 30 | 30 | 100 | 15 |
| 182 | 4.0 | 0 | 5 | 90 | 10 | 5 | 30 | 5 |

TABLE VI-continued

Post-Emergence Testing

| Comp. No. | Rate kg/ha | AVEFA | ECHCG | SETVI | ABUTH | IPOSS | SINAR | CYPES |
|---|---|---|---|---|---|---|---|---|
| 183 | 4.0 | 90 | 98 | 98 | 85 | 80 | 100 | 10 |
| 184 | 4.0 | 90 | 95 | 100 | 100 | 60 | 100 | 20 |
| 185 | 4.0 | 90 | 100 | 85 | 20 | 20 | 100 | 5 |
| 186 | 4.0 | 0 | 5 | 20 | 0 | 0 | 20 | 0 |
| 187 | 4.0 | 0 | 0 | 10 | 0 | 0 | 0 | 0 |
| 188 | 4.0 | 5 | 20 | 90 | 80 | 10 | 95 | 5 |
| 189 | 4.0 | 80 | 100 | 95 | 100 | 75 | 100 | 25 |
| 190 | 4.0 | 0 | 20 | 40 | 0 | 5 | 50 | 0 |
| 191 | 4.0 | 0 | 20 | 10 | 15 | 5 | 15 | 0 |
| 192 | 4.0 | 5 | 0 | 5 | 5 | 10 | 85 | 5 |
| 193 | 4.0 | 5 | 30 | 20 | 0 | 5 | 15 | 0 |
| 194 | 4.0 | 70 | 95 | 90 | 80 | 85 | 100 | 60 |
| 195 | 4.0 | 75 | 90 | 95 | 95 | 50 | 100 | 15 |
| 196 | 4.0 | 60 | 95 | 98 | 95 | 50 | 100 | 5 |
| 197 | 4.0 | 30 | 70 | 95 | 70 | 15 | 100 | 15 |
| 198 | 4.0 | 50 | 98 | 90 | 85 | 70 | 100 | 80 |
| 199 | 4.0 | 20 | 98 | 95 | 90 | 20 | 100 | 80 |
| 200 | 4.0 | 10 | 10 | 30 | 60 | 30 | 80 | 50 |
| 201 | 4.0 | 98 | 98 | 20 | 50 | 50 | 100 | 5 |
| 202 | 4.0 | 10 | 10 | 50 | 0 | 5 | 100 | 10 |
| 203 | 4.0 | 5 | 5 | 10 | 10 | 10 | 70 | 10 |
| 204 | 4.0 | 5 | 5 | 5 | 10 | 5 | 50 | 10 |
| 205 | 4.0 | 0 | 0 | 0 | 0 | 0 | 10 | 0 |
| 206 | 4.0 | 40 | 98 | 30 | 10 | 20 | 80 | 10 |
| 207 | 4.0 | 80 | 90 | 90 | 70 | 30 | 100 | 5 |
| 208 | 4.0 | 0 | 10 | 5 | 5 | 0 | 40 | 0 |
| 209 | 4.0 | 40 | 40 | 30 | 15 | 20 | 80 | 40 |
| 210 | 4.0 | 95 | 75 | 15 | 100 | 15 | 100 | 10 |
| 211 | 1.0 | 20 | 10 | 5 | 5 | 5 | 15 | 0 |
| 212 | 1.0 | 80 | 95 | 75 | 85 | 5 | 95 | 10 |
| 213 | 1.0 | 15 | 15 | 25 | 15 | 10 | 40 | 5 |
| 214 | 1.0 | 60 | 80 | 95 | 5 | 30 | 80 | 25 |
| 215 | 1.0 | 5 | 15 | 60 | 20 | 0 | 30 | 0 |
| 216 | 1.0 | 90 | 100 | 98 | 95 | 90 | 100 | 85 |
| 217 | 1.0 | 70 | 85 | 85 | 5 | 5 | 50 | 20 |
| 218 | 1.0 | 40 | 15 | 30 | 0 | 5 | 10 | 0 |
| 219 | 1.0 | 90 | 85 | 60 | 10 | 5 | 85 | 35 |
| 220 | 1.0 | 95 | 95 | 95 | 40 | 10 | 100 | 50 |
| 221 | 1.0 | 95 | 100 | 95 | 65 | 40 | 100 | 40 |
| 222 | 1.0 | 60 | 95 | 90 | 65 | 65 | 100 | 35 |
| 223 | 1.0 | 75 | 95 | 95 | 25 | 15 | 100 | 35 |
| 224 | 1.0 | 98 | 98 | 100 | 85 | 35 | 100 | 75 |
| 225 | 1.0 | 90 | 98 | 98 | 65 | 50 | 100 | 65 |
| 226 | 1.0 | 85 | 90 | 95 | 25 | 15 | 70 | 30 |
| 227 | 1.0 | 75 | 95 | 95 | 10 | 10 | 95 | 15 |
| 228 | 1.0 | 100 | 98 | 98 | 90 | 10 | 85 | 50 |
| 229 | 1.0 | 98 | 95 | 98 | 60 | 5 | 40 | 30 |
| 230 | 1.0 | 10 | 15 | 50 | 0 | 5 | 60 | 0 |
| 231 | 1.0 | 98 | 95 | 98 | 65 | 65 | 100 | 40 |
| 232 | 1.0 | 85 | 94 | 98 | 60 | 75 | 100 | 30 |
| 233 | 1.0 | 95 | 90 | 98 | 100 | 90 | 100 | 25 |
| 234 | 1.0 | 75 | 60 | 70 | 35 | 20 | 25 | 20 |
| 235 | 1.0 | 70 | 60 | 95 | 70 | 20 | 80 | 15 |
| 236 | 1.0 | 90 | 90 | 98 | 70 | 75 | 100 | 20 |
| 237 | 1.0 | 98 | 98 | 100 | 75 | 15 | 100 | 70 |
| 238 | 1.0 | 70 | 40 | 60 | 25 | 10 | 70 | 20 |
| 239 | 1.0 | 100 | 100 | 98 | 80 | 15 | 100 | 20 |
| 240 | 1.0 | 40 | 70 | 85 | 20 | 5 | 60 | 15 |
| 241 | 1.0 | 90 | 95 | 98 | 70 | 20 | 90 | 10 |
| 242 | 1.0 | 98 | 75 | 95 | 65 | 15 | 20 | 10 |
| 243 | 1.0 | 75 | 40 | 70 | 60 | 10 | 90 | 10 |
| 244 | 1.0 | 98 | 98 | 80 | 60 | 20 | 40 | 20 |
| 245 | 1.0 | 100 | 100 | 100 | 95 | 85 | 100 | 25 |
| 247 | 1.0 | 100 | 100 | 100 | 60 | 15 | 90 | 65 |
| 248 | 1.0 | 100 | 98 | 98 | 75 | 40 | 100 | 20 |
| 249 | 4.0 | 85 | 60 | 98 | 15 | 25 | 100 | 35 |
| 250 | 4.0 | 90 | 35 | 60 | 15 | 5 | 95 | 20 |
| 251 | 4.0 | 0 | 0 | 0 | 0 | 0 | 0 | 0 |
| 252 | 4.0 | 0 | 10 | 70 | 15 | 30 | 100 | 5 |
| 253 | 4.0 | 0 | 0 | 0 | 60 | 15 | 10 | 0 |
| 254 | 4.0 | 0 | 0 | 10 | 5 | 0 | 15 | 0 |
| 255 | 4.0 | 0 | 0 | 10 | 0 | 0 | 0 | 0 |
| 256 | 4.0 | 0 | 0 | 0 | 0 | 0 | 0 | 0 |
| 257 | 1.0 | 100 | 100 | 100 | 90 | 65 | 100 | 60 |

TABLE VI-continued

Post-Emergence Testing

| Comp. No. | Rate kg/ha | AVEFA | ECHCG | SETVI | ABUTH | IPOSS | SINAR | CYPES |
|---|---|---|---|---|---|---|---|---|
| 258 | 1.0 | 100 | 100 | 100 | 98 | 30 | 100 | 95 |
| 259 | 1.0 | 100 | 100 | 100 | 100 | 65 | 100 | 65 |
| 260 | 1.0 | 75 | 65 | 98 | 0 | 20 | 95 | 15 |
| 261 | 1.0 | 100 | 100 | 100 | 80 | 75 | 100 | 50 |
| 262 | 1.0 | 100 | 98 | 100 | 65 | 60 | 100 | 60 |
| 264 | 1.0 | 100 | 95 | 100 | 60 | 95 | 100 | 10 |
| 265 | 1.0 | 100 | 95 | 100 | 60 | 50 | 100 | 40 |
| 266 | 1.0 | 30 | 15 | 10 | 0 | 15 | 15 | 5 |
| 267 | 1.0 | 100 | 100 | 100 | 98 | 70 | 100 | 70 |
| 268 | 1.0 | 30 | 10 | 5 | 0 | 5 | 15 | 0 |
| 269 | 1.0 | 40 | 10 | 10 | 100 | 10 | 25 | 0 |
| 270 | 1.0 | 100 | 100 | 100 | 100 | 85 | 100 | 80 |
| 271 | 1.0 | 80 | 90 | 30 | 50 | 15 | 15 | 20 |
| 272 | 1.0 | 20 | 5 | 10 | 0 | 0 | 10 | 0 |
| 273 | 1.0 | 98 | 100 | 98 | 40 | 20 | 85 | 90 |
| 274 | 1.0 | 100 | 100 | 100 | 60 | 30 | 100 | 60 |
| 275 | 1.0 | 90 | 70 | 60 | 75 | 30 | 30 | 5 |
| 276 | 4.0 | 60 | 60 | 60 | 60 | 10 | 25 | 10 |
| 277 | 1.0 | 100 | 90 | 90 | 15 | 30 | 100 | 10 |
| 278 | 1.0 | 85 | 50 | 30 | 30 | 15 | 30 | 5 |
| 279 | 1.0 | 100 | 100 | 95 | 60 | 80 | 100 | 60 |
| 280 | 1.0 | 100 | 80 | 75 | 50 | 30 | 25 | 10 |
| 281 | 1.0 | 60 | 20 | 10 | 0 | 10 | 15 | 30 |
| 282 | 1.0 | 10 | 20 | 15 | 0 | 5 | 40 | 10 |
| 283 | 1.0 | 100 | 85 | 95 | 85 | 30 | 100 | 50 |
| 284 | 1.0 | 80 | 90 | 95 | 20 | 20 | 75 | 30 |
| 285 | 1.0 | 15 | 40 | 60 | 0 | 10 | 60 | 40 |
| 286 | 1.0 | 70 | 80 | 98 | 5 | 10 | 20 | 10 |
| 287 | 1.0 | 40 | 75 | 30 | 5 | 10 | 15 | 15 |
| 288 | 1.0 | 0 | 5 | 5 | 50 | 0 | 15 | 0 |
| 289 | 1.0 | 75 | 75 | 40 | 40 | 15 | 40 | 15 |
| 290 | 1.0 | 0 | 0 | 5 | 0 | 0 | 10 | 0 |
| 291 | 1.0 | 40 | 10 | 20 | 5 | 10 | 15 | 5 |
| 292 | 1.0 | 0 | 0 | 5 | 15 | 30 | 20 | 0 |
| 293 | 4.0 | 0 | 0 | 0 | 5 | 10 | 10 | 0 |
| 294 | 1.0 | 75 | 75 | 98 | 5 | 10 | 60 | 10 |
| 295 | 1.0 | 100 | 98 | 100 | 85 | 30 | 100 | 5 |
| 296 | 1.0 | 20 | 90 | 40 | 0 | 5 | 30 | 40 |
| 297 | 1.0 | 30 | 30 | 60 | 5 | 10 | 30 | 10 |
| 298 | 1.0 | 0 | 10 | 20 | 0 | 5 | 15 | 10 |
| 299 | 1.0 | 0 | 0 | 0 | 0 | 0 | 0 | 0 |
| 300 | 1.0 | 70 | 90 | 95 | 50 | 40 | 100 | 10 |
| 301 | 1.0 | 70 | 25 | 50 | 25 | 10 | 70 | 5 |
| 302 | 1.0 | 100 | 15 | 50 | 10 | 10 | 85 | 20 |
| 303 | 1.0 | 100 | 100 | 100 | 50 | 50 | 100 | 60 |
| 304 | 1.0 | 98 | 98 | 98 | 5 | 40 | 95 | 30 |
| 305 | 1.0 | 5 | 10 | 10 | 10 | 10 | 10 | 0 |
| 306 | 1.0 | 70 | 30 | 30 | 5 | 10 | 15 | 10 |
| 307 | 1.0 | 60 | 40 | 50 | 10 | 5 | 60 | 15 |
| 308 | 1.0 | 95 | 95 | 90 | 70 | 15 | 100 | 15 |
| 309 | 1.0 | 20 | 25 | 70 | 0 | 10 | 30 | 5 |
| 310 | 1.0 | 60 | 70 | 50 | 5 | 15 | 15 | 5 |
| 311 | 1.0 | 70 | 95 | 95 | 30 | 30 | 60 | 25 |
| 312 | 1.0 | 25 | 10 | 10 | 0 | 5 | 20 | 0 |
| 313 | 1.0 | 100 | 90 | 90 | 75 | 80 | 100 | 60 |
| 314 | 1.0 | 65 | 70 | 95 | 0 | 5 | 15 | 5 |
| 315 | 1.0 | 0 | 10 | 50 | 0 | 0 | 5 | 0 |
| 316 | 1.0 | 70 | 50 | 85 | 15 | 5 | 90 | 5 |
| 317 | 1.0 | 20 | 60 | 80 | 0 | 5 | 60 | 0 |
| 318 | 1.0 | 100 | 100 | 100 | 75 | 70 | 100 | 75 |
| 319 | 1.0 | 75 | 95 | 95 | 10 | 15 | 75 | 5 |
| 320 | 1.0 | 65 | 90 | 95 | 0 | 10 | 70 | 15 |
| 321 | 1.0 | 75 | 20 | 25 | 5 | 15 | 20 | 20 |
| 322 | 1.0. | 100 | 98 | 100 | 40 | 30 | 100 | 40 |
| 323 | 1.0 | 95 | 95 | 95 | 5 | 10 | 75 | 10 |
| 324 | 1.0 | 75 | 80 | 90 | 40 | 5 | 40 | 40 |
| 325 | 1.0 | 90 | 100 | 100 | 10 | 15 | 98 | 30 |
| 326 | 1.0 | 75 | 95 | 95 | 0 | 15 | 100 | 20 |
| 327 | 1.0 | 90 | 95 | 98 | 15 | 10 | 65 | 15 |
| 328 | 1.0 | 95 | 80 | 95 | 10 | 25 | 100 | 15 |
| 329 | 1.0 | 85 | 40 | 75 | 5 | 10 | 60 | 30 |
| 330 | 1.0 | 100 | 98 | 100 | 90 | 90 | 100 | 40 |
| 331 | 1.0 | 90 | 95 | 90 | 75 | 55 | 80 | 25 |
| 332 | 1.0 | 20 | 0 | 5 | 5 | 0 | 5 | 0 |

TABLE VI-continued

Post-Emergence Testing

| Comp. No. | Rate kg/ha | AVEFA | ECHCG | SETVI | ABUTH | IPOSS | SINAR | CYPES |
|---|---|---|---|---|---|---|---|---|
| 333 | 1.0 | 80 | 70 | 100 | 50 | 25 | 60 | 30 |
| 334 | 1.0 | 98 | 95 | 100 | 50 | 30 | 100 | 40 |
| 335 | 1.0 | 100 | 95 | 100 | 50 | 10 | 100 | 30 |
| 336 | 1.0 | 50 | 70 | 85 | 20 | 5 | 100 | 15 |
| 337 | 1.0 | 85 | 95 | 80 | 15 | 20 | 50 | 5 |
| 338 | 1.0 | 0 | 0 | 5 | 15 | 5 | 70 | 0 |
| 339 | 1.0 | 15 | 20 | 70 | 0 | 5 | 30 | 10 |
| 340 | 1.0 | 20 | 40 | 50 | 5 | 0 | 20 | 0 |
| 341 | 1.0 | 90 | 98 | 95 | 70 | 5 | 100 | 40 |
| 342 | 1.0 | 10 | 10 | 15 | 5 | 5 | 25 | 0 |
| 343 | 1.0 | 0 | 0 | 0 | 0 | 5 | 10 | 0 |
| 344 | 1.0 | 100 | 100 | 100 | 5 | 10 | 100 | 40 |
| 345 | 1.0 | 0 | 10 | 10 | 0 | 0 | 15 | 5 |
| 346 | 1.0 | 90 | 100 | 100 | 10 | 5 | 100 | 40 |
| 347 | 1.0 | 100 | 100 | 90 | 40 | 25 | 60 | 40 |
| 348 | 1.0 | 0 | 0 | 5 | 0 | 0 | 10 | 0 |
| 349 | 1.0 | 0 | 0 | 0 | 0 | 10 | 20 | 0 |
| 350 | 1.0 | 100 | 98 | 98 | 30 | 25 | 100 | 10 |
| 351 | 1.0 | 30 | 25 | 20 | 5 | 10 | 25 | 5 |
| 352 | 1.0 | 0 | 0 | 5 | 0 | 5 | 10 | 0 |
| 353 | 1.0 | 0 | 0 | 0 | 0 | 0 | 0 | 0 |
| 354 | 1.0 | 40 | 10 | 10 | 5 | 5 | 15 | 10 |
| 355 | 1.0 | 100 | 100 | 100 | 40 | 40 | 100 | 30 |
| 356 | 1.0 | 0 | 0 | 10 | 0 | 5 | 20 | 0 |
| 357 | 1.0 | 0 | 0 | 10 | 0 | 5 | 5 | 0 |
| 358 | 1.0 | 70 | 95 | 90 | 0 | 5 | 80 | 15 |
| 359 | 1.0 | 10 | 10 | 30 | 0 | 5 | 20 | 0 |
| 360 | 1.0 | 75 | 70 | 90 | 0 | 10 | 40 | 0 |
| 361 | 1.0 | 0 | 0 | 0 | 0 | 20 | 5 | 0 |
| 362 | 1.0 | 0 | 0 | 0 | 0 | 0 | 0 | 0 |
| 363 | 1.0 | 100 | 98 | 100 | 5 | 10 | 100 | 25 |
| 364 | 1.0 | 0 | 0 | 0 | 0 | 5 | 0 | 0 |
| 365 | 1.0 | 0 | 0 | 0 | 0 | 0 | 10 | 0 |
| 366 | 1.0 | 100 | 95 | 100 | 20 | 20 | 100 | 10 |
| 367 | 1.0 | 0 | 0 | 0 | 0 | 0 | 0 | 0 |
| 368 | 1.0 | 0 | 0 | 0 | 0 | 5 | 5 | 0 |
| 369 | 1.0 | 0 | 0 | 0 | 0 | 0 | 10 | 0 |
| 370 | 1.0 | 15 | 50 | 60 | 0 | 5 | 25 | 5 |
| 371 | 1.0 | 10 | 15 | 10 | 0 | 5 | 5 | 0 |
| 372 | 1.0 | 100 | 100 | 100 | 20 | 10 | 100 | 80 |
| 373 | 1.0 | 85 | 95 | 100 | 5 | 5 | 100 | 30 |
| 374 | 1.0 | 0 | 10 | 20 | 0 | 10 | 60 | 0 |
| 375 | 1.0 | 100 | 95 | 95 | 0 | 20 | 98 | 25 |
| 376 | 1.0 | 0 | 0 | 0 | 0 | 0 | 0 | 0 |
| 377 | 1.0 | 100 | 100 | 100 | 10 | 10 | 98 | 50 |
| 378 | 1.0 | 0 | 0 | 0 | 0 | 0 | 0 | 0 |
| 379 | 1.0 | 100 | 85 | 98 | 0 | 15 | 40 | 10 |
| 380 | 1.0 | 0 | 0 | 0 | 0 | 0 | 0 | 0 |
| 381 | 1.0 | 0 | 0 | 0 | 0 | 0 | 0 | 0 |
| 382 | 1.0 | 100 | 95 | 98 | 10 | 20 | 95 | 35 |
| 383 | 1.0 | 100 | 100 | 100 | 70 | 10 | 100 | 90 |
| 384 | 1.0 | 100 | 50 | 90 | 0 | 5 | 65 | 5 |
| 385 | 1.0 | 65 | 25 | 30 | 0 | 5 | 60 | 10 |
| 386 | 1.0 | 10 | 10 | 15 | 0 | 10 | 10 | 0 |
| 387 | 1.0 | 30 | 5 | 10 | 0 | 5 | 10 | 0 |
| 388 | 1.0 | 80 | 50 | 80 | 10 | 5 | 60 | 60 |
| 389 | 1.0 | 0 | 0 | 5 | 0 | 0 | 0 | 0 |
| 390 | 4.0 | 0 | 0 | 0 | 0 | 0 | 5 | 0 |
| 391 | 1.0 | 95 | 98 | 85 | 25 | 30 | 80 | 15 |
| 392 | 1.0 | 95 | 70 | 98 | 10 | 10 | 95 | 40 |
| 393 | 1.0 | 85 | 75 | 95 | 10 | 60 | 100 | 5 |
| 394 | 1.0 | 90 | 75 | 95 | 30 | 5 | 100 | 30 |
| 395 | 1.0 | 0 | 5 | 15 | 0 | 5 | 15 | 0 |
| 396 | 1.0 | 85 | 50 | 85 | 0 | 0 | 80 | 10 |
| 397 | 1.0 | 90 | 50 | 70 | 10 | 5 | 5 | 5 |
| 398 | 1.0 | 30 | 15 | 70 | 0 | 10 | 20 | 10 |
| 399 | 1.0 | 0 | 10 | 85 | 0 | 5 | 30 | 0 |
| 400 | 1.0 | 100 | 100 | 100 | 0 | 20 | 100 | 20 |
| 401 | 1.0 | 100 | 70 | 100 | 5 | 10 | 85 | 5 |
| 492 | 1.0 | 0 | 0 | 0 | 0 | 0 | 0 | 0 |
| 403 | 1.0 | 95 | 20 | 50 | 5 | 10 | 35 | 10 |
| 404 | 1.0 | 85 | 10 | 90 | 0 | 10 | 15 | 0 |
| 405 | 1.0 | 80 | 40 | 95 | 0 | 15 | 10 | 5 |
| 406 | 1.0 | 20 | 75 | 95 | 75 | 10 | 70 | 60 |

TABLE VI-continued

Post-Emergence Testing

| Comp. No. | Rate kg/ha | AVEFA | ECHCG | SETVI | ABUTH | IPOSS | SINAR | CYPES |
|---|---|---|---|---|---|---|---|---|
| 407 | 1.0 | 10 | 5 | 15 | 60 | 10 | 10 | 0 |
| 408 | 1.0 | 100 | 95 | 100 | 40 | 10 | 100 | 15 |
| 409 | 1.0 | 0 | 0 | 0 | 10 | 0 | 10 | 0 |
| 410 | 1.0 | 75 | 80 | 95 | 35 | 20 | 100 | 65 |
| 411 | 1.0 | 0 | 20 | 60 | 0 | 5 | 40 | 0 |
| 412 | 1.0 | 20 | 60 | 95 | 35 | 5 | 100 | 50 |
| 413 | 1.0 | 60 | 25 | 70 | 0 | 5 | 65 | 5 |
| 414 | 1.0 | 25 | 10 | 70 | 20 | 5 | 75 | 0 |
| 415 | 4.0 | 0 | 10 | 0 | 0 | 5 | 0 | 0 |
| 416 | 1.0 | 75 | 70 | 60 | 5 | 10 | 10 | 10 |
| 417 | 1.0 | 95 | 98 | 60 | 10 | 15 | 60 | 50 |
| 418 | 1.0 | 95 | 25 | 95 | 0 | 15 | 75 | 10 |
| 419 | 1.0 | 100 | 100 | 100 | 10 | 10 | 90 | 15 |
| 420 | 1.0 | 90 | 90 | 95 | 5 | 5 | 100 | 20 |
| 421 | 1.0 | 15 | 20 | 95 | 10 | 5 | 60 | 5 |
| 422 | 1.0 | 10 | 0 | 0 | 0 | 0 | 0 | 0 |
| 423 | 1.0 | 80 | 60 | 60 | 0 | 5 | 10 | 5 |
| 424 | 4.0 | 0 | 0 | 0 | 0 | 10 | 0 | 0 |
| 425 | 1.0 | 100 | 98 | 100 | 10 | 10 | 100 | 50 |
| 426 | 1.0 | 50 | 30 | 90 | 0 | 25 | 25 | 0 |
| 427 | 1.0 | 15 | 20 | 25 | 0 | 5 | 5 | 0 |
| 423 | 1.0 | 20 | 25 | 85 | 5 | 5 | 75 | 0 |
| 429 | 1.0 | 0 | 0 | 0 | 0 | 0 | 0 | 0 |
| 430 | 1.0 | 0 | 0 | 0 | 0 | 5 | 10 | 0 |
| 431 | 1.0 | 100 | 98 | 100 | 30 | 15 | 100 | 20 |
| 432 | 1.0 | 25 | 10 | 15 | 0 | 10 | 15 | 10 |
| 433 | 1.0 | 100 | 100 | 100 | 20 | 40 | 100 | 60 |
| 434 | 1.0 | 100 | 100 | 100 | 40 | 20 | 100 | 50 |
| 435 | 1.0 | 75 | 65 | 70 | 0 | 5 | 10 | 5 |
| 436 | 1.0 | 50 | 50 | 50 | 15 | 5 | 20 | 10 |
| 437 | 1.0 | 80 | 98 | 98 | 0 | 20 | 100 | 75 |
| 438 | 1.0 | 98 | 100 | 60 | 10 | 10 | 60 | 20 |
| 439 | 1.0 | 85 | 95 | 95 | 0 | 5 | 100 | 20 |
| 440 | 1.0 | 5 | 10 | 15 | 0 | 0 | 5 | 0 |
| 441 | 1.0 | 0 | 0 | 0 | 0 | 0 | 0 | 0 |
| 442 | 1.0 | 10 | 10 | 10 | 0 | 0 | 5 | 0 |
| 443 | 1.0 | 0 | 0 | 5 | 0 | 0 | 5 | 0 |
| 444 | 1.0 | 10 | 10 | 10 | 10 | 5 | 15 | 10 |
| 445 | 1.0 | 98 | 98 | 85 | 5 | 10 | 25 | 25 |
| 446 | 1.0 | 10 | 0 | 0 | 0 | 0 | 0 | 0 |
| 447 | 1.0 | 80 | 95 | 90 | 225 | 10 | 70 | 30 |
| 448 | 1.0 | 85 | 80 | 70 | 40 | 5 | 70 | 5 |
| 449 | 1.0 | 70 | 80 | 90 | 10 | 5 | 50 | 10 |
| 450 | 1.0 | 25 | 75 | 85 | 5 | 5 | 60 | 0 |
| 451 | 1.0 | 0 | 0 | 0 | 0 | 0 | 10 | 0 |
| 452 | 1.0 | 0 | 0 | 0 | 0 | 0 | 0 | 0 |
| 453 | 1.0 | 10 | 10 | 10 | 0 | 5 | 5 | 0 |
| 454 | 1.0 | 5 | 15 | 40 | 0 | 5 | 15 | 0 |
| 455 | 1.0 | 85 | 95 | 65 | 0 | 20 | 60 | 40 |
| 456 | 1.0 | 0 | 0 | 15 | 0 | 5 | 20 | 0 |
| 457 | 1.0 | 85 | 85 | 85 | 10 | 5 | 60 | 15 |
| 458 | 1.0 | 90 | 95 | 98 | 50 | 20 | 95 | 60 |
| 459 | 1.0 | 60 | 60 | 95 | 0 | 0 | 90 | 5 |
| 460 | 1.0 | 75 | 70 | 60 | 10 | 10 | 40 | 20 |
| 461 | 1.0 | 10 | 5 | 5 | 0 | 0 | 10 | 0 |
| 462 | 1.0 | 70 | 80 | 95 | 0 | 5 | 50 | 0 |
| 463 | 1.0 | 10 | 0 | 10 | 0 | 5 | 10 | 0 |
| 464 | 1.0 | 20 | 0 | 10 | 0 | 5 | 25 | 0 |
| 465 | 1.0 | 60 | 25 | 40 | 0 | 5 | 5 | 5 |
| 466 | 1.0 | 30 | 5 | 5 | 0 | 0 | 10 | 5 |
| 467 | 1.0 | 100 | 80 | 90 | 5 | 5 | 98 | 30 |
| 468 | 1.0 | 80 | 70 | 65 | 5 | 5 | 60 | 25 |
| 469 | 1.0 | 90 | 70 | 75 | 0 | 5 | 65 | 40 |
| 470 | 1.0 | 15 | 80 | 75 | 5 | 0 | 75 | 5 |
| 471 | 1.0 | 75 | 90 | 95 | 70 | 10 | 100 | 20 |
| 472 | 1.0 | 50 | 70 | 90 | 20 | 10 | 95 | 10 |
| 473 | 1.0 | 15 | 0 | 30 | 0 | 0 | 10 | 0 |
| 474 | 1.0 | 100 | 98 | 100 | 65 | 60 | 100 | 60 |
| 475 | 1.0 | 100 | 100 | 100 | 90 | 80 | 100 | 70 |
| 476 | 1.0 | 90 | 75 | 80 | 50 | 50 | 70 | 10 |
| 477 | 1.0 | 100 | 100 | 100 | 100 | 80 | 100 | 85 |
| 478 | 1.0 | 100 | 100 | 100 | 95 | 75 | 100 | 70 |
| 479 | 1.0 | 100 | 100 | 100 | 100 | 95 | 100 | 80 |
| 480 | 1.0 | 100 | 100 | 100 | 95 | 65 | 100 | 70 |

TABLE VI-continued

Post-Emergence Testing

| Comp. No. | Rate kg/ha | AVEFA | ECHCG | SETVI | ABUTH | IPOSS | SINAR | CYPES |
|---|---|---|---|---|---|---|---|---|
| 481 | 4.0 | 20 | 20 | 50 | 10 | 0 | 70 | 20 |
| 482 | 4.0 | 0 | 0 | 0 | 0 | 0 | 0 | 0 |

Each compound listed in Table VI was also tested at the stated application rate for pre-emergence weed control as described above. With the exception of the compounds listed in Table VII below, the tested compounds had no effect on the growth of the listed weed species, i.e., had a 0 percent control rating, when applied pre-emergently.

TABLE VII

Pre-Emergence Testing

| Comp. No. | Rate kg/ha | AVEFA | ECHCG | SETVI | ABUTH | IPOSS | SINAR | CYPES |
|---|---|---|---|---|---|---|---|---|
| 4 | 4.0 | 0 | 0 | 25 | 0 | 0 | 0 | 0 |
| 10 | 4.0 | 0 | 0 | 0 | 10 | 0 | 30 | 0 |
| 54 | 1.0 | 0 | 0 | 0 | 15 | 25 | 5 | 0 |
| 150 | 4.0 | — | — | — | — | — | — | — |
| 151 | 4.0 | — | — | — | — | — | — | — |
| 169 | 4.0 | 0 | 0 | 0 | 5 | — | 5 | 15 |
| 184 | 4.0 | 0 | 0 | 10 | 15 | 10 | 25 | 0 |
| 249 | 4.0 | 0 | 0 | 0 | 0 | 0 | 20 | 0 |
| 253 | 4.0 | 0 | 0 | 0 | 10 | 0 | 0 | 0 |
| 438 | 1.0 | 0 | 0 | 0 | 20 | 0 | 70 | 0 |
| 442 | 1.0 | 0 | 0 | 5 | 0 | 10 | 5 | 0 |
| 471 | 1.0 | 0 | 0 | 0 | 20 | 0 | 0 | 0 |

The above data shows the post-emergence efficacy of the herbicidal compounds and compositions of this invention, coupled with their safety to plants when applied pre-emergently.

Although the invention has been described with reference to preferred embodiments and examples thereof, the scope of the present invention is not limited only to those described embodiments. As will be apparent to persons skilled in the art, modifications and adaptations to the above-described invention can be made without departing from the spirit and scope of the invention, which is defined and circumscribed by the appended claims.

What is claimed is:

1. An herbicidal composition comprising:
   (A) an herbicidally effective amount of a compound of Formula (I)

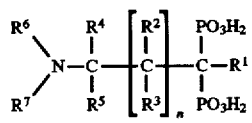

wherein n is 0, 1, 2, 3, 4, 5 or 6;

$R^1$ is hydrogen, hydroxy, $C_1$–$C_4$ alkoxy, halogen, $C_1$–$C_4$ alkyl, $C_1$–$C_4$ haloalkyl, hydroxy-$C_1$–$C_4$-alkyl, hydroxy-$C_1$–$C_4$-alkoxy or $N(R^8)(R^9)$ wherein $R^8$ and $R^9$ are each independently hydrogen or $C_1$–$C_3$ alkyl;

each $R^2$, $R^3$, $R^4$ and $R^5$ is independently hydrogen; hydrocarbyl; substituted hydrocarbyl; hydrocarbyloxy; substituted hydrocarbyloxy; hydrocarbyl-S(O)m—; or substituted hydrocarbyl-S(O)$_m$—;

$R^6$ and $R^7$ are each independently hydrogen; hydrocarbyl; substituted hydrocarbyl; hydrocarbyloxy; substituted hydrocarbyloxy; hydrocarbyl-S(O)$_m$—; substituted hydrocarbyl-S(O)$_m$—; pyridyl; substituted pyridyl; or are of the formula $N(R^{12})(R^{13})$ wherein $R^{12}$ and $R^{13}$ are independently hydrogen, hydrocarbyl or substituted hydrocarbyl; or $R^6$ and $R^7$ together with the nitrogen to which they are bound form an aziridine; piperazine; morpholine; thiomorpholine; thiomorpholine sulfinyl; thiomorpholine sulfonyl; hexamethyleneimine; piperidine, tetrahydropyridine; pyrazole; imidazole; pyrrole; triazole; tetrahydropyrimidine; dihydroimidazole; pyrroline; azetidine; perhydroindole; perhydroquinoline; perhydroisoquinoline or pyrrolidine ring; any of which may be optionally substituted with $C_1$–$C_{12}$ alkyl, halo, hydroxy, $C_1$–$C_{10}$ hydroxyalkyl, $C_1$–$C_5$ haloalkyl, $C_6$–$C_{10}$ aryl, $C_6$–$C_{10}$ aryl substituted with halo or $C_1$–$C_6$ alkyl, $C_7$–$C_{16}$ arylalkyl, $C_7$–$C_{16}$ arylalkyl substituted with halo or $C_1$–$C_6$ alkyl, nitro, halo-$C_1$–$C_{10}$ alkyl, $C_1$–$C_{10}$ alkoxy, $C_1$–$C_{10}$ alkylthio, $C_1$–$C_{10}$ alkylsulfonyl, phenoxy, phenoxy substituted with halo or $C_1$–$C_6$ alkyl, $C_2$–$C_{10}$ alkenyl or cyano; or $R^4$ and $R^6$ or $R^2$ and $R^6$ together with the nitrogen and carbon atoms to which they are bound form an aziridine; piperazine; morpholine, thiomorpholine; thiomorpholine sulfinyl; thiomorpholine sulfonyl; hexamethyleneimine; piperidine, tetrahydropyridine; pyrazole; imidazole; pyrrole; triazole, tetrahydropyrimidine; dihydroimidazole; pyrroline; azetidine; perhydroindole; perhydroquinoline; perhydroisoquinoline; or pyrrolidine ring; any of which may be optionally substituted with $C_1$–$C_{12}$ alkyl, hydroxy, $C_1$–$C_{10}$ hydroxyalkyl, $C_1$–$C_5$ haloalkyl, halo, $C_6$–$C_{10}$ aryl, $C_6$–$C_{10}$ aryl substituted with halo or $C_1$–$C_6$ alkyl, $C_7$–$C_{16}$ arylalkyl, $C_7$–$C_{16}$ arylalkyl substituted with halo or $C_1$–$C_6$ alkyl, nitro, halo-$C_1$–$C_{10}$-alkyl, $C_1$–$C_{10}$ alkoxy, $C_1$–$C_{10}$ alkylthio, $C_1$–$C_{10}$ alkylsulfonyl, phenoxy, phenoxy substituted with halo or $C_1$–$C_6$ alkyl, $C_2$–$C_{10}$ alkenyl or cyano; or

- $R^2$ and $R^4$ together with the carbon atoms to which they are bound form a $C_5$–$C_6$ cycloalkyl or cycloalkenyl ring; any of which may be optionally substituted with $C_1$–$C_{12}$ alkyl, hydroxy, $C_1$–$C_{10}$ hydroxyalkyl, $C_1$–$C_5$ haloalkyl, halo, $C_6$–$C_{10}$ aryl, $C_6$–$C_{10}$ aryl substituted with halo or $C_1$–$C_6$ alkyl, $C_7$–$C_{16}$ arylalkyl, $C_7$–$C_{16}$ arylalkyl substituted with halo or $C_1$–$C_6$ alkyl, nitro, halo-$C_1$–$C_{10}$ alkyl, $C_1$–$C_{10}$ alkoxy, $C_1$–$C_{10}$ alkylthio, $C_1$–$C_{10}$ alkylsulfonyl, phenoxy, phenoxy substituted with halo or $C_1$–$C_6$ alkyl, $C_2$–$C_{10}$ alkenyl or cyano; or
- $R^4$ and $R^5$ together form a 3–6 membered carbocyclic ring, optionally substituted with halogen, hydroxy, $C_1$–$C_6$ alkyl, $C_1$–$C_6$ alkoxy, $C_1$–$C_6$ alkylthio or $N(R^{10})(R^{11})$ wherein $R^{10}$ and $R^{11}$ are each independently hydrogen or $C_1$–$C_{12}$ alkyl; and
- m is 0, 1 or 2;
- or an agrochemically acceptable salt or hydrolyzable ester thereof;
- with the proviso that when n is 0, $R^4$ and $R^5$ are both hydrogen and $R^6$ and $R^7$ are both —$C_2H_5$, $R^1$ is not —$NH_2$; and (B) an agrochemically acceptable carrier therefor.

2. A composition according to claim 1, wherein $R^1$ is hydrogen or hydroxy.

3. A composition according to claim 1, wherein $R^2$, $R^3$, $R^4$ and $R^5$ are independently hydrogen, $C_1$–$C_8$ alkyl, $C_2$–$C_8$ alkenyl or $C_6$–$C_{10}$ aralkyl optionally substituted with halogen or hydroxy.

4. A composition according to claim 1, wherein $R^6$ and $R^7$ are each independently hydrogen, $C_1$–$C_8$ alkyl, $C_2$–$C_8$ alkenyl, or $C_6$–$C_{10}$ aralkyl optionally substituted with halogen or hydroxy.

5. A composition according to claim 1, wherein $R^4$ and $R^5$ together with the nitrogen and carbon atoms to which they are bound form a pyrrolidine or piperidine ring, either of which may be optionally substituted with halogen, hydroxy, $C_1$–$C_6$ alkoxy or $C_1$–$C_6$ alkyl.

6. A composition according to claim 1, wherein $R^6$ and $R^7$ together with the nitrogen to which they are bound form a pyrrolidine or piperidine ring, either of which may be optionally substituted with halogen, hydroxy, $C_1$–$C_6$ alkoxy or $C_1$–$C_6$ alkyl.

7. A composition according to claim 1, wherein n is 0 or 1.

8. A composition according to claim 1, wherein $R^1$ is hydrogen, hydroxy, halogen or $C_1$–$C_4$ alkyl;

$R^2$, $R^3$, $R^4$ and $R^5$ are independently hydrogen; $C_1$–$C_{12}$ alkyl; $C_2$–$C_{12}$ alkenyl; $C_2$–$C_{12}$ alkynyl; halo-$C_1$–$C_{12}$ alkyl, halo-$C_2$–$C_{12}$ alkenyl; halo-$C_2$–$C_{12}$-alkynyl; $C_6$–$C_{14}$ aralkyl; $C_1$–$C_{12}$ alkoxy; or $C_1$–$C_{12}$ alkylthio;

$R^6$ and $R^7$ are independently hydrogen; $C_1$–$C_{12}$ alkyl; $C_2$–$C_{12}$ alkenyl; $C_2$–$C_{12}$ alkynyl; halo-$C_1$–$C_{12}$ alkyl; halo-$C_2$–$C_{12}$ alkenyl; halo-$C_2$–$C_{12}$ alkynyl; pyridyl; substituted pyridyl; phenyl; substituted phenyl; $C_6$–$C_{14}$ aralkyl; substituted $C_6$–$C_{14}$ aralkyl; $C_1$–$C_{12}$ alkoxy or $C_1$–$C_{12}$ alkylthio; or $R^2$ and $R^4$ together with the carbon atoms to which they are bound form an optionally substituted $C_5$–$C_6$ cycloalkyl or cycloalkenyl ring; or $R^4$ and $R^6$ together with the nitrogen and carbon atoms to which they are bound form a 3- to 7-membered ring optionally substituted with halogen, hydroxy, $C_1$–$C_6$ alkyl, $C_1$–$C_6$ alkylthio or $C_7$–$C_{16}$ aralkyl; or $R^6$ and $R^7$ together with the nitrogen to which they are bound form a 3- to 7-membered ring, optionally substituted with halogen, hydroxy, $C_1$–$C_6$ alkoxy, nitro, $C_1$–$C_6$ alkyl, $C_7$–$C_{16}$ aralkyl or $C_1$–$C_6$ alkylthio groups; and n is 0, 1, 2 or 3.

9. A composition according to claim 1, wherein $R^1$ is hydrogen or hydroxy;

$R^2$ and $R^3$ are hydrogen;

$R^4$ and $R^5$ are each independently hydrogen, $C_1$–$C_8$ alkyl, $C_2$–$C_8$ alkenyl or $C_6$–$C_{10}$ aralkyl optionally substituted with halogen or hydroxy; and $R^6$ and $R^7$ are each independently hydrogen, $C_1$–$C_8$ alkyl, $C_2$–$C_8$ alkenyl, or $C_6$–$C_{10}$ aralkyl optionally substituted with halogen or hydroxy; or $R^4$ and $R^6$ together with the nitrogen and carbon atoms to which they are bound form a pyrrolidine or piperidine ring, either of which may be optionally substituted with halogen, hydroxy, $C_1$–$C_6$ alkoxy or $C_1$–$C_6$ alkyl; or $R^6$ and $R^7$ together with the nitrogen to which they are bound form a pyrrolidine or piperidine ring, either of which may be optionally substituted with halogen, hydroxy, $C_1$–$C_6$ alkoxy or $C_1$–$C_6$ alkyl; and n is 0 or 1.

10. A method of controlling the growth of plants comprising applying to the locus of such plants an herbicidally effective amount of a compound of the Formula (I):

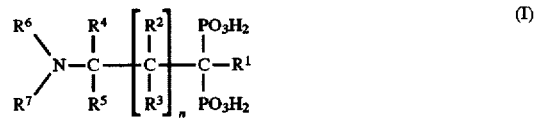

wherein n is 0, 1, 2, 3, 4, 5 or 6;

$R^1$ is hydrogen, hydroxy, $C_1$–$C_4$ alkoxy, halogen, $C_1$–$C_4$ alkyl, $C_1$–$C_4$ haloalkyl, hydroxy-$C_1$–$C_4$-alkyl, hydroxy-$C_1$–$C_4$-alkoxy or $N(R^8)(R^9)$ wherein $R^8$ and $R^9$ are each independently hydrogen or $C_1$–$C_3$ alkyl;

each $R^2$, $R^3$, $R^4$ and $R^5$ is independently hydrogen; hydrocarbyl; substituted hydrocarbyl; hydrocarbyloxy; substituted hydrocarbyloxy; hydrocarbyl-S(O)$_m$—; or substituted hydrocarbyl-S(O)$_m$—;

$R^6$ and $R^7$ are each independently hydrogen; hydrocarbyl; substituted hydrocarbyl; hydrocarbyloxy; substituted hydrocarbyloxy; hydrocarbyl-S(O)$_m$—; substituted hydrocarbyl-S(O)$_m$—; pyridyl; substituted pyridyl; or are of the formula $N(R^{12})(R^{13})$ wherein $R^{12}$ and $R^{13}$ are independently hydrogen, hydrocarbyl or substituted hydrocarbyl; or $R^6$ and $R^7$ together with the nitrogen to which they are bound form an aziridine; piperazine; morpholine; thiomorpholine; thiomorpholine sulfinyl; thiomorpholine sulfonyl; hexamethyleneimine; piperidine, tetrahydropyridine; pyrazole; imidazole; pyrrole; triazole; tetrahydropyrimidine; dihydroimidazole; pyrroline; azetidine; perhydroindole; perhydroquinoline; perhydroisoquinoline or pyrrolidine ring; any of which may be optionally substituted with $C_1$–$C_{12}$ alkyl, halo, hydroxy, $C_1$–$C_{10}$ hydroxyalkyl, $C_1$–$C_5$ haloalkyl, $C_6$–$C_{10}$ aryl, $C_6$–$C_{10}$ aryl substituted with halo or $C_1$–$C_6$ alkyl, $C_7$–$C_{16}$ arylalkyl, $C_7$–$C_{16}$ arylalkyl substituted with halo or $C_1$–$C_6$ alkyl, nitro, halo-$C_1$–$C_{10}$-alkyl, $C_1$–$C_{10}$ alkoxy, $C_1$–$C_{10}$ alkylthio, $C_1$–$C_{10}$ alkylsulfonyl, phenoxy, phenoxy substituted with halo or $C_1$–$C_6$ alkyl, $C_2$–$C_{10}$ alkenyl or cyano; or $R^4$ and $R^6$ or $R^2$ and $R^6$ together with the nitrogen and carbon atoms to which they are bound form an aziridine; piperazine; morpholine, thiomorpholine; thiomorpholine sulfinyl; thiomorpholine sulfonyl; hexamethyleneimine; piperidine, tetrahydropyridine; pyrazole; imidazole; pyrrole; triazole, tetrahydropyrimidine; dihydroimidazole; pyrroline; azetidine; perhydroindole; perhydroquinoline; perhydroisoquinoline; or pyrrolidine ring; any of which may be optionally substituted with $C_1$–$C_{12}$ alkyl, hydroxy, $C_1$–$C_{10}$ hydroxyalkyl, $C_1$–$C_5$ haloalkyl, halo, $C_6$–$C_{10}$ aryl, $C_6$–$C_{10}$ aryl substituted with halo or $C_1$–$C_6$ alkyl, $C_7$–$C_{16}$ arylalkyl, $C_7$–$C_{16}$ arylalkyl substituted with halo or $C_1$–$C_6$ alkyl, nitro, halo-$C_1$–$C_{10}$-alkyl, $C_1$–$C_{10}$ alkoxy, $C_1$–$C_{10}$ alkylthio, $C_1$–$C_{10}$ alkylsulfonyl, phenoxy, phenoxy substituted with halo or $C_1$–$C_6$ alkyl, $C_2$–$C_{10}$ alkenyl or cyano; or $R^2$ and $R^4$ together with the carbon atoms to which they are bound form a $C_5$–$C_6$ cycloalkyl or cycloalkenyl ring; any of which may be optionally substituted with $C_1$–$C_{12}$ alkyl, hydroxy, $C_1$–$C_{10}$ hydroxyalkyl, $C_1$–$C_5$ haloalkyl, halo, $C_6$–$C_{10}$ aryl, $C_6$–$C_{10}$ aryl substituted with halo or $C_1$–$C_6$ alkyl, $C_7$–$C_{16}$ arylalkyl, $C_7$–$C_{16}$ arylalkyl substituted with halo or $C_1$–$C_6$ alkyl, nitro, halo-$C_1$–$C_{10}$-alkyl, $C_1$–$C_{10}$ alkoxy, $C_1$–$C_{10}$ alkylthio, $C_1$–$C_{10}$ alkylsulfonyl, phenoxy, phenoxy substituted with halo or $C_1$–$C_6$ alkyl, $C_2$–$C_{10}$ alkenyl or cyano; or $R^4$ and $R^5$ together form a 3–6 membered carbocyclic ring, optionally substituted with halogen, hydroxy, $C_1$–$C_6$ alkyl, $C_1$–$C_6$ alkoxy, $C_1$–$C_6$ alkylthio or N($R^{10}$)($R^{11}$) wherein $R^{10}$ and $R^{11}$ are each independently hydrogen or $C_1$–$C_{12}$ alkyl; and m is 0, 1 or 2;

or an agrochemically acceptable salt or hydrolyzable ester thereof;

with the proviso that when n is 0, $R^4$ and $R^5$ are both hydrogen and $R^6$ and $R^7$ are both —$C_2H_5$, $R^1$ is not —$NH_2$.

11. A method according to claim 10, wherein $R^1$ is hydrogen or hydroxy.

12. A method according to claim 10, wherein $R^2$, $R^3$, $R^4$ and $R^5$ are independently hydrogen, $C_1$–$C_8$ alkyl, $C_2$–$C_8$ alkenyl or $C_6$–$C_{10}$ aralkyl optionally substituted with halogen or hydroxy.

13. A method according to claim 10, wherein $R^6$ and $R^7$ are each independently hydrogen, $C_1$–$C_8$ alkyl, $C_2$–$C_8$ alkenyl, or $C_6$–$C_{10}$ aralkyl optionally substituted with halogen or hydroxy.

14. A method according to claim 10, wherein $R^4$ and $R^5$ together with the nitrogen and carbon atoms to which they are bound form a pyrrolidine or piperidine ring, either of which may be optionally substituted with halogen, hydroxy, $C_1$–$C_6$ alkoxy or $C_1$–$C_6$ alkyl.

15. A method according to claim 10, wherein $R^6$ and $R^7$ together with the nitrogen to which they are bound form a pyrrolidine or piperidine ring, either of which may be optionally substituted with halogen, hydroxy, $C_1$–$C_6$ alkoxy or $C_1$–$C_6$ alkyl.

16. A method according to claim 10, wherein n is 0 or 1.

17. A method according to claim 10, wherein $R^1$ is hydrogen, hydroxy, halogen or $C_1$–$C_4$ alkyl;

$R^2$, $R^3$, $R^4$ and $R^5$ are independently hydrogen; $C_1$–$C_{12}$ alkyl; $C_2$–$C_{12}$ alkenyl; $C_2$–$C_{12}$ alkynyl; halo-$C_1$–$C_{12}$ alkyl, halo-$C_2$–$C_{12}$ alkenyl; halo-$C_2$–$C_{12}$-alkynyl; $C_6$–$C_{14}$ aralkyl; $C_1$–$C_{12}$ alkoxy; or $C_1$–$C_{12}$ alkylthio;

$R^6$ and $R^7$ are independently hydrogen; $C_1$–$C_{12}$ alkyl; $C_2$–$C_{12}$ alkenyl; $C_2$–$C_{12}$ alkynyl; halo-$C_1$–$C_{12}$ alkyl; halo-$C_2$–$C_{12}$ alkenyl; halo-$C_2$–$C_{12}$ alkynyl; pyridyl; substituted pyridyl; phenyl; substituted phenyl; $C_6$–$C_{14}$ aralkyl; substituted $C_6$–$C_{14}$ aralkyl; $C_1$–$C_{12}$ alkoxy or $C_1$–$C_{12}$ alkylthio; or $R^2$ and $R^4$ together with the carbon atoms to which they are bound form an optionally substituted $C_5$–$C_6$ cycloalkyl or cycloalkenyl ring; or $R^4$ and $R^6$ together with the nitrogen and carbon atoms to which they are bound form a 3- to 7-membered ring optionally substituted with halogen, hydroxy, $C_1$–$C_6$ alkyl, $C_1$–$C_6$ alkylthio or $C_7$–$C_{16}$ aralkyl; or $R^6$ and $R^7$ together with the nitrogen to which they are bound form a 3- to 7-membered ring, optionally substituted with halogen, hydroxy, $C_1$–$C_6$ alkoxy, nitro, $C_1$–$C_6$ alkyl, $C_7$–$C_{16}$ aralkyl or $C_1$–$C_6$ alkylthio groups; and n is 0, 1, 2 or 3.

18. A method according to claim 10, wherein $R^1$ is hydrogen or hydroxy;

$R^2$ and $R^3$ are hydrogen;

$R^4$ and $R^5$ are each independently hydrogen, $C_1$–$C_8$ alkyl, $C_2$–$C_8$ alkenyl or $C_6$–$C_{10}$ aralkyl optionally substituted with halogen or hydroxy; and $R^6$ and $R^7$ are each independently hydrogen, $C_1$–$C_8$ alkyl, $C_2$–$C_8$ alkenyl, or $C_6$–$C_{10}$ aralkyl optionally substituted with halogen or hydroxy; or $R^4$ and $R^6$ together with the nitrogen and carbon atoms to which they are bound form a pyrrolidine or piperidine ring, either of which may be optionally substituted with halogen, hydroxy, $C_1$–$C_6$ alkoxy or $C_1$–$C_6$ alkyl; or $R^6$ and $R^7$ together with the nitrogen to which they are bound form a pyrrolidine or piperidine ring, either of which may be optionally substituted with halogen, hydroxy, $C_1$–$C_6$ alkoxy or $C_1$–$C_6$ alkyl; and n is 0 or 1.

* * * * *